(12) United States Patent
Mason et al.

(10) Patent No.: US 9,062,324 B2
(45) Date of Patent: *Jun. 23, 2015

(54) HERBICIDE TOLERANT SOYBEAN PLANTS AND METHODS FOR IDENTIFYING SAME

(75) Inventors: Justin Thomas Mason, Granger, IA (US); Leslie James Lettow, Guthrie Center, IA (US); Mark Alan Eby, Adel, IA (US); William H. Eby, Panora, IA (US); Günter Welz, Wolfenbüttel (DE); Steven Verhaeghe, Grammene-Deinze (BE); Marc De Beuckeleer, Zwijnaarde (BE); Veerle Habex, Gullegem (BE); Jean-Marc Ferrulo, Comines (FR)

(73) Assignees: M.S. TECHNOLOGIES LLC, West Point, IA (US); BAYER CROPSCIENCE N.V., Diegem (BE)

( * ) Notice: Subject to any disclaimer, the term of this patent is extended or adjusted under 35 U.S.C. 154(b) by 450 days.

This patent is subject to a terminal disclaimer.

(21) Appl. No.: 12/953,251

(22) Filed: Nov. 23, 2010

(65) Prior Publication Data

US 2011/0239321 A1   Sep. 29, 2011

Related U.S. Application Data

(60) Provisional application No. 61/263,707, filed on Nov. 23, 2009, provisional application No. 61/367,251, filed on Jul. 23, 2010.

(30) Foreign Application Priority Data

Nov. 23, 2009   (EP) .................................... 09014565

(51) Int. Cl.
*C12N 15/82* (2006.01)
*A01H 5/00* (2006.01)
*A01H 1/00* (2006.01)
*A01H 5/10* (2006.01)

(52) U.S. Cl.
CPC .............. *C12N 15/8274* (2013.01); *A01H 5/10* (2013.01); *C12N 15/8275* (2013.01)

(58) Field of Classification Search
USPC ........................................................ 800/300
See application file for complete search history.

(56) References Cited

U.S. PATENT DOCUMENTS

| | | | |
|---|---|---|---|
| 5,510,471 A | 4/1996 | Lebrun et al. | |
| 5,985,557 A | 11/1999 | Prudent et al. | |
| 6,001,567 A | 12/1999 | Brow et al. | |
| 6,245,968 B1 | 6/2001 | Boudec et al. | |
| 6,376,754 B1 | 4/2002 | Schillinger et al. | |
| 6,566,587 B1 | 5/2003 | Lebrun et al. | |
| 7,250,561 B1 * | 7/2007 | Pallett et al. | 800/300 |
| 8,592,650 B2 | 11/2013 | Mason et al. | |
| 8,642,748 B2 | 2/2014 | Mason et al. | |
| 2002/0100076 A1 | 7/2002 | Garcon et al. | |
| 2002/0112260 A1 | 8/2002 | Schillinger et al. | |
| 2003/0233675 A1 | 12/2003 | Cao et al. | |
| 2004/0214272 A1 | 10/2004 | La Rosa et al. | |
| 2006/0135758 A1 | 6/2006 | Wu | |
| 2006/0282915 A1 | 12/2006 | Malven et al. | |
| 2007/0061916 A1 | 3/2007 | Kovalic et al. | |
| 2007/0083334 A1 | 4/2007 | Mintz et al. | |
| 2007/0118921 A1 | 5/2007 | Boukharov et al. | |
| 2008/0028481 A1 | 1/2008 | Pallett et al. | |
| 2008/0163392 A1 | 7/2008 | Zink et al. | |
| 2008/0196127 A1 | 8/2008 | De Beuckeleer | |
| 2008/0312082 A1 | 12/2008 | Kinney et al. | |
| 2008/0320616 A1 | 12/2008 | De Beuckeleer | |
| 2009/0013431 A1 | 1/2009 | Van Thournout et al. | |
| 2009/0036308 A1 | 2/2009 | Guida, Jr. et al. | |
| 2009/0093620 A1 | 4/2009 | Kovalic et al. | |
| 2009/0130071 A1 | 5/2009 | Gao et al. | |
| 2009/0191188 A1 | 7/2009 | Krieg et al. | |
| 2012/0304330 A1 | 11/2012 | Mason et al. | |
| 2012/0304331 A1 | 11/2012 | Mason et al. | |

FOREIGN PATENT DOCUMENTS

| | | |
|---|---|---|
| AU | 734878 | 6/2001 |
| EP | 1 186 666 | 3/2002 |
| EP | 1186666 | 3/2002 |
| FR | 2 770 854 | 5/1999 |
| WO | 97/43618 | 11/1990 |
| WO | WO 97/04103 | 2/1997 |
| WO | 98-02562 | 1/1998 |
| WO | 01/88089 | 11/2001 |
| WO | WO 2006/108674 | 10/2006 |

(Continued)

OTHER PUBLICATIONS

Hohe et al, A tool for understanding homologous recombination in plants, Plant Cell Rep. (2003) 21:1135-1142.*
Carrington and Freed, Journal of Virology, vol. 64, pp. 1590-1597 (1990).
Chaboute et al., Plant Molecular Biology, vol. 8, pp. 179-191 (1987).
Chaubet et al., Journal of Molecular Biology, vol. 225, pp. 569-574 (1992).
Depicker et al., Journal of Molecular and Applied Genetics, vol. 1, pp. 561-573 (1982).
Edwards et al., Nucleic Acid Research, vol. 19, p. 1349 (1991).
Elmore et al., Agronomy Journal, vol. 93, pp. 408-412 (2001).
Kasey, Bloomberg Web Page downloaded from the Internet on Nov. 17, 2009 at: www.bloomberg.com/apps/news?pid=newsarchive&sid=ad4L0hH9MKwE.

(Continued)

*Primary Examiner* — David H Kruse
*Assistant Examiner* — Mykola Kovalenko
(74) *Attorney, Agent, or Firm* — Hunton & Williams LLP

(57) ABSTRACT

The invention provides specific transgenic soybean plants, plant material and seeds, characterized in that these products harbor a stack of specific transformation events at specific locations in the soybean genome (elite event EE-GM3 and elite event EE-GM2, or elite event EE-GM3 and elite event EE-GM1). The invention also provides for methods of producing soybean plants and seeds having elite event EE-GM3 and elite event EE-GM2, or elite event EE-GM3 and elite event EE-GM1.

65 Claims, 6 Drawing Sheets

(56) References Cited

FOREIGN PATENT DOCUMENTS

| WO | WO 2006/108675 | 10/2006 |
|---|---|---|
| WO | WO 2006/130436 | 12/2006 |
| WO | WO 2007-017186 | 2/2007 |
| WO | WO 2007/017186 | 2/2007 |
| WO | WO 2008/002872 | 1/2008 |
| WO | WO 2008/054747 | 5/2008 |
| WO | 2008-141154 | 11/2008 |
| WO | WO 2010/080829 | 7/2010 |
| WO | WO 2011/063413 | 5/2011 |

OTHER PUBLICATIONS

Nelson et al., Agronomy Journal, vol. 94, pp. 1270-1281 (2002).
Nickell et al., Crop Sci., vol. 1365, p. 30 (1990).
Wilbur and Lipmann, Proc. Nat. Acad. Sci. USA, vol. 80, p. 726 (1983).
USDA-APHIS Petition 06-354-01p (2006).
USDA-APHIS Petition 06-271-01p (2006).
USDA-APHIS Petition 06-178-01p (2006).
USDA-APHIS Petition 98-238-01p (1998).
USDA-APHIS Petition 98-014-01p (1998).
USDA-APHIS Petition 97-008-01p (1997).
USDA-APHIS Petition 96-068-01p (1996).
USDA-APHIS Petition 93-258-01p (1993).
International Search Report for International Application No. PCT/US2010/57869, mailed Mar. 22, 2011.
Written Opinion for International Application No. PCT/US2010/57869, mailed Mar. 22, 2011.
Notification concerning transmittal of International Preliminary Report on Patentability and Written Opinion from PCT/US2010/057886 mailed Jun. 7, 2012.
International Search Report for International Application No. PCT/US2010/57886, mailed Jun. 15, 2011.
Written Opinion for International Application No. PCT/US2010/57886, mailed Jun. 15, 2011.
Onishi et al., "Development of a Multiplex Polymerase Chain Reaction Method for Simultaneous Detection of Eight Events of Genetically Modified Maize," Journal Agricultural and Food Chemistry, vol. 53, pp. 9713-9721 (2005).
Herouet-Guicheney, et al. (2009) *Regulatory Toxicology and Pharmacology* 54(2):143-153.
Green, Jerry M., "Evolution of Glyphosate-Resistant Crop Technology," Weed Science, vol. 57, pp. 108-117, 2009.
Supplemental European Search Report for International Patent Application No. PCT/US2010/057869, dated Apr. 25, 2013.
AIPO Patent Examination Report No. 1 for AU Patent Application No. 2010321584 mailed May 30, 2014.
Privalle et al, Development of an Agricultural Biotechnology Crop Product: Testing from Discovery to Commercialiation, J. of Agric. and Food Chem. (2012) 10179-10187.
Puchta et al, From centiMorgans to Base Pairs: Homologous in Plants, Trends in Plant Sci. (1996) 1:340-348.
Devine, M, Why are There Not More Herbicide-Tolerant Crops? Pest Mngmt. Sci (2005) 61:312-317.
Japanese Office Action mailed Feb. 3, 2015, Patent Application No. 2012-541173.

* cited by examiner

HERBICIDE TOLERANT SOYBEAN PLANTS AND METHODS FOR IDENTIFYING SAME

CROSS-REFERENCE TO RELATED APPLICATIONS

This patent application claims the benefit of U.S. Provisional Patent Application No. 61/367,251, filed Jul. 23, 2010; U.S. Provisional Patent Application No. 61/263,707, filed Nov. 23, 2009; and priority to European Patent Application No. EP 09014565.7, filed Nov. 23, 2009, the disclosures of each of which are hereby incorporated by reference in their entireties.

FIELD OF THE INVENTION

This invention relates to transgenic soybean plants, plant material and seeds, characterized by harboring at least two specific transformation events, particularly by the presence of at least two sets of genes encoding proteins that confer herbicide tolerance, each at a specific location in the soybean genome. The soybean plants of the invention combine the herbicide tolerance phenotype with an agronomic performance, genetic stability and functionality in different genetic backgrounds equivalent to the non-transformed soybean line in the absence of herbicide(s). This invention further provides methods and kits for identifying the presence of plant material comprising specifically transformation event EE-GM3 and EE-GM2 or EE-GM1 in biological samples.

BACKGROUND OF THE INVENTION

The phenotypic expression of a transgene in a plant is determined both by the structure of the gene or genes itself and by its or their location in the plant genome. At the same time the presence of the transgenes or "foreign DNA" at different locations in the genome will influence the overall phenotype of the plant in different ways. The agronomically or industrially successful introduction of a commercially interesting trait in a plant by genetic manipulation can be a lengthy procedure dependent on different factors. The actual transformation and regeneration of genetically transformed plants are only the first in a series of selection steps, which include extensive genetic characterization, breeding, and evaluation in field trials, eventually leading to the selection of an elite event.

The unequivocal identification of an elite event is becoming increasingly important in view of discussions on Novel Food/Feed, segregation of GMO and non-GMO products and the identification of proprietary material. Ideally, such identification method is both quick and simple, without the need for an extensive laboratory set-up. Furthermore, the method should provide results that allow unequivocal determination of the elite event without expert interpretation, but which hold up under expert scrutiny if necessary. Specific tools for use in the identification of elite event EE-GM3 and EE-GM1 or EE-GM2 in biological samples are described herein.

In this invention, EE-GM3 has been identified as an elite event from a population of transgenic soybean plants in the development of herbicide tolerant soybean (*Glycine max*) comprising a gene coding for glyphosate tolerance combined with a gene conferring tolerance to 4-hydroxy phenylpyruvate dioxygenase (HPPD) inhibitors, each under control of a plant-expressible promoter.

EE-GM1 and EE-GM2 have previously been identified as elite events from a population of transgenic soybean plants in the development of herbicide tolerant soybean (*Glycine max*) comprising a gene coding for glufosinate tolerance under control of a plant-expressible promoter and are described in WO2006/108674 and WO2006/108675 (both publications herein incorporated by reference).

Soybean plants comprising a herbicide tolerance gene have been disclosed in the art. However, none of the prior art disclosures teach or suggest the present invention.

It is known in the art that getting a commercial herbicide tolerant elite transformation event in soybean plants with acceptable agronomic performance, with no yield drag, and providing sufficient herbicide tolerance, certainly to 3 different classes of herbicides, is by no means straightforward.

Indeed, it has been reported that the first soybean event (event 40-3-2) released on the market with herbicide tolerance, had a significant yield drag compared to (near-)isogenic lines (Elmore et al. (2001) Agron. J. 93:408-412).

Also, Optimum™ GAT™ soybeans (event 356043) were developed to combine tolerance to glyphosate with tolerance to ALS herbicides, but it has been reported that these soybeans were not meeting the standards for glyphosate tolerance by itself (without combination with another glyphosate tolerance soybean event (such as event 40-3-2).

SUMMARY OF THE PREFERRED EMBODIMENTS OF THE INVENTION

The present invention relates to a transgenic soybean plant, or seed, cells or tissues thereof, comprising, stably integrated into its genome, an expression cassette which comprises a herbicide tolerance gene comprising the coding sequence of the 2mEPSPS gene and another herbicide tolerance gene comprising the coding sequence of HPPD-PF W336 (both as described in Example 1.1 herein and as represented in SEQ ID No 1) as well as a second expression cassette comprising a herbicide tolerance gene comprising the coding sequence of a phosphinothricin acetyl transferase, as described in Example 1 herein and as represented in SEQ ID No 11. The transgenic soybean plant, or seed, cells or tissues thereof are tolerant to herbicides based on glyphosate, based on glufosinate, and an HPPD inhibitor herbicide such as isoxaflutole, and, in the absence of herbicide(s), has an agronomic performance which is substantially equivalent to the non-transgenic isogenic line. After application of one or more herbicides to which tolerance is provided, the plant will have a superior agronomic phenotype compared to a non-transgenic plant.

According to the present invention the soybean plant or seed, cells or tissues thereof comprise elite event EE-GM3 and EE-GM1 or EE-GM3 and EE-GM2.

More specifically, the present invention relates to a transgenic soybean plant, seed, cells or tissues thereof, the genomic DNA of which is characterized by the fact that, when analyzed in a PCR Identification Protocol as described herein, using two primers directed to the 5' or 3' flanking region of EE-GM3 and the foreign DNA comprising herbicide tolerance genes in EE-GM-3, respectively, yields a fragment which is specific for EE-GM3 and further when analyzed in a PCR Identification Protocol as described herein, using two primers directed to the 5' or 3' flanking region of EE-GM1 or EE-GM2 and the foreign DNA comprising glufosinate tolerance genes, respectively, yields a fragment which is specific for EE-GM1 or EE-GM2. The primers for detection of EE-GM3 may be directed against the 5' flanking region within SEQ ID NO: 2 and the foreign DNA comprising herbicide tolerance genes, respectively. The primers for detection of EE-GM3 may also be directed against the 3' flanking region within SEQ ID NO: 3 and the foreign DNA comprising herbicide tolerance genes, respectively, such as the primers comprising or consisting (essentially) of the nucleotide sequence of SEQ ID NO: 5 and SEQ ID NO: 4 or SEQ ID No.: 7 respectively, and yield a DNA fragment of between 100 and 800 bp, such as a fragment of about 263 bp or about 706 bp. The primers for detection of EE-GM1 may be directed against the 5' flanking region within SEQ ID NO: 12 and the foreign DNA comprising herbicide tolerance genes, respectively. The primers for detection of EE-GM1 may also be directed against the 3' flanking region within SEQ ID NO: 13 and the foreign DNA comprising herbicide tolerance genes, respectively, such as the primers comprising or consisting (essentially) of the nucleotide sequence of SEQ ID NO: 16 and SEQ ID NO: 17 respectively, and yield a DNA fragment of between 100 and 500 bp, such as a fragment of about 183 bp. The primers for detection of EE-GM2 may be directed against the 5' flanking region within SEQ ID NO: 14 and the foreign DNA comprising herbicide tolerance genes, respectively. The primers for detection of EE-GM2 may also be directed against the 3' flanking region within SEQ ID NO: 15 and the foreign DNA comprising herbicide tolerance genes, respectively, such as the primers comprising or consisting (essentially) of the nucleotide sequence of SEQ ID NO: 18 and SEQ ID NO: 19 respectively, and yield a DNA fragment of between 100 and 500 bp, such as a fragment of about 151 bp.

Reference seed comprising the elite event EE-GM3 of the invention has been deposited at the NCIMB under accession number NCIMB 41659. Reference seed comprising the elite event EE-GM1 of the invention has been deposited at the NCIMB under accession number NCIMB 41658. Reference seed comprising the elite event EE-GM2 of the invention has been deposited at the NCIMB under accession number NCIMB 41660. Reference seed comprising elite event EE-GM3 and EE-GM1 was deposited at the ATCC under accession number PTA-11041. Reference seed comprising elite event EE-GM3 and EE-GM2 was deposited at the ATCC under accession number PTA-11042.

One embodiment of the invention is seed comprising elite event EE-GM3 (reference seed comprising said event being deposited as NCIMB accession number NCIMB 41659) and further comprising elite event EE-GM1 (reference seed comprising said event being deposited as NCIMB accession number NCIMB 41658), or seed comprising event EE-GM3 and EE-GM1 (reference seed comprising said events being deposited at the ATCC under accession number PTA-11041) which will grow into a soybean plant tolerant to at least three herbicides, particularly tolerant to glyphosate and/or HPPD inhibitors such as isoxaflutole and/or glutamine synthetase inhibitors such as glufosinate.

Another embodiment of the invention is seed comprising elite event EE-GM3 (reference seed comprising said event being deposited as NCIMB accession number NCIMB 41659) and further comprising elite event EE-GM2 (reference seed comprising said event being deposited as NCIMB accession number NCIMB 41660), or seed comprising event EE-GM3 and EE-GM2 (reference seed comprising said events being deposited at the ATCC under accession number PTA-11042), which will grow into a soybean plant tolerant to at least three herbicides, particularly tolerant to glyphosate and/or HPPD inhibitors such as isoxaflutole and/or glutamine synthetase inhibitors such as glufosinate.

The seed of NCIMB deposit number NCIMB 41659, is a seed lot consisting of at least about 95% transgenic seeds, comprising elite event EE-GM3, which will grow into herbicide tolerant plants, whereby the plants are glyphosate and/or isoxaflutole tolerant plants. The seed or progeny seed obtainable or obtained from the deposited seed (e.g., following crossing with other soybean plants with a different genetic background) can be sown and the growing plants can be treated with glyphosate or HPPD inhibitors such as isoxaflutole as described herein to obtain glyphosate or isoxaflutole-tolerant plants, comprising elite event EE-GM3. The seed of NCIMB deposit number NCIMB 41658 and NCIMB 41660 are seed lots consisting of at least about 95% transgenic seeds, comprising elite events EE-GM1 or EE-GM2, respectively, which will grow into herbicide tolerant plants, whereby the plants are glufosinate-tolerant plants. The seed can be sown and the growing plants can be treated with glufosinate as described herein to obtain glufosinate tolerant plants, comprising the elite events EE-GM1 or EE-GM2.

The seed of ATCC deposit number PTA-11041, is a seed lot consisting of at least about 95% transgenic seeds, comprising elite event EE-GM3 and elite event EE-GM1 in homozygous form, which will grow into herbicide tolerant plants, whereby the plants are glyphosate, glufosinate and/or isoxaflutole tolerant plants. The seed or progeny seed obtainable or obtained from the deposited seed (e.g., following crossing with other soybean plants with a different genetic background) can be sown and the growing plants can be treated with glyphosate, glufosinate and/or HPPD inhibitors such as isoxaflutole, as described herein to obtain glyphosate, glufosinate and/or isoxaflutole-tolerant plants, comprising elite event EE-GM3 and EE-GM1.

The seed of ATCC deposit number PTA-11042, is a seed lot consisting of at least about 95% transgenic seeds, comprising elite event EE-GM3 and elite event EE-GM2 in homozygous form, which will grow into herbicide tolerant plants, whereby the plants are glyphosate, glufosinate and/or isoxaflutole tolerant plants. The seed or progeny seed obtainable or obtained from the deposited seed (e.g., following crossing with other soybean plants with a different genetic background) can be sown and the growing plants can be treated with glyphosate, glufosinate and/or HPPD inhibitors such as isoxaflutole, as described herein to obtain glyphosate, glufosinate and/or isoxaflutole-tolerant plants, comprising elite event EE-GM3 and EE-GM2.

The invention further relates to cells, tissues, progeny, and descendants from a plant comprising the elite event EE-GM3 and further comprising elite event EE-GM1, and which may be obtained by growing a plant comprising the elite event EE-GM3 and EE-GM1 deposited at ATCC as PTA-11041, or by growing a plant comprising the elite event EE-GM3 from the seed deposited at the NCIMB having accession number NCIMB 41659 and crossing said plant with a plant comprising elite event EE-GM1 grown from the seed deposited at the NCIMB having accession number NCIMB 41658. The invention also relates to cells, tissues, progeny, and descendants from a plant comprising the elite event EE-GM3 and further comprising elite event EE-GM2, and which may be obtained by growing a plant comprising the elite event EE-GM3 and EE-GM2 deposited at ATCC as PTA-11042, or by growing a plant comprising the elite event EE-GM3 from the seed deposited at the NCIMB having accession number NCIMB 41659 and crossing said plant with a plant comprising elite event EE-GM2 grown from the seed deposited at the NCIMB having accession number NCIMB 41660. The invention further relates to plants obtainable from (such as by propagation of and/or breeding with) a soybean plant or seed as described immediately above. The invention also relates to soybean plants comprising elite event EE-GM3 and EE-GM1 or EE-GM3 and EE-GM2.

The invention further relates to a method for identifying a transgenic plant, or cells or tissues thereof, comprising elite event EE-GM3 and EE-GM1 or EE-GM3 and EE-GM2, which method is based on identifying the presence of characterizing DNA sequences or amino acids encoded by such DNA sequences in the transgenic plant, cells or tissues. According to a preferred embodiment of the invention, such characterizing DNA sequences are sequences of at least 15 bp, 15 bp, at least 20 bp, 20 bp, or 30 bp or more which comprise the insertion site of the event, i.e., both a part of the inserted foreign DNA comprising herbicide tolerance genes and a part of the soybean genome (either the 5' or 3' flanking region) contiguous therewith, allowing specific identification of the elite event.

The present invention further relates to methods for identifying elite events EE-GM3 and EE-GM1 or elite events EE-GM3 and EE-GM2 in biological samples, which methods are based on primers or probes which specifically recognize the 5' and/or 3' flanking sequence of the foreign DNA comprising the herbicide tolerance genes in EE-GM3 and EE-GM1 or EE-GM3 and EE-GM2.

More specifically, the invention relates to a method comprising amplifying two sequences of a nucleic acid present in biological samples, using two polymerase chain reactions each with at least two primers or one polymerase chain reaction with at least four primers, the first primer recognizing the 5' or 3' flanking region of foreign DNA comprising herbicide tolerance genes comprising the herbicide tolerance genes in EE-GM3, the second primer recognizing a sequence within the foreign DNA comprising herbicide tolerance genes of EE-GM3, the third primer recognizing the 5' or 3' flanking region of foreign DNA comprising the herbicide tolerance genes in EE-GM1 or EE-GM2, and the fourth primer recognizing a sequence within the foreign DNA comprising the herbicide tolerance genes of EE-GM1 or EE-GM2, preferably to obtain two DNA fragments of between 100 and 800 bp. The primers for identifying EE-GM3 may recognize a sequence within the 5' flanking region of EE-GM3 (SEQ ID No. 2, from position 1 to position 1451) or within the 3' flanking region of EE-GM3 (complement of SEQ ID No 3 from position 241 to position 1408) and a sequence within the foreign DNA comprising the herbicide tolerance genes (complement of SEQ ID No 2 from position 1452 to 1843 or SEQ ID No 3 from position 1 to position 240, or SEQ ID No 20 from nucleotide position 1452 to nucleotide position 16638 or its complement), respectively. The primer recognizing the 3' flanking region may comprise the nucleotide sequence of SEQ ID No. 5 and the primer recognizing a sequence within the foreign DNA comprising herbicide tolerance genes may comprise the nucleotide sequence of SEQ ID No. 4 or SEQ ID No.: 7 described herein. The primers for identifying EE-GM1 may recognize a sequence within the 5' flanking region of EE-GM1 (SEQ ID No. 12, from position 1 to position 209) or within the 3' flanking region of EE-GM1 (complement of SEQ ID No 13 from position 569 to position 1000) and a sequence within the foreign DNA comprising herbicide tolerance gene of EE-GM1 (complement of SEQ ID No 12 from position 210 to 720, or SEQ ID No 13 from position 1 to position 568), respectively. The primer recognizing the 5' flanking region of EE-GM1 may comprise the nucleotide sequence of SEQ ID No. 16 and the primer recognizing a sequence within the foreign DNA of EE-GM1 may comprise the nucleotide sequence of SEQ ID No. 17 described herein. The primers for identifying EE-GM2 may recognize a sequence within the 5' flanking region of EE-GM2 (SEQ ID No. 14, from position 1 to position 311) or within the 3' flanking region of EE-GM2 (complement of SEQ ID No 15 from position 508 to position 1880) and a sequence within the foreign DNA comprising herbicide tolerance gene of EE-GM1 (complement of SEQ ID No 14 from position 312 to 810, or SEQ ID No 15 from position 1 to position 507), respectively. The primer recognizing the 3' flanking region of EE-GM2 may comprise the nucleotide sequence of SEQ ID No. 18 and the primer recognizing a sequence within the foreign DNA of EE-GM2 may comprise the nucleotide sequence of SEQ ID No. 19 described herein. The PCR amplification may be done simultaneously or sequentially.

The present invention more specifically relates to a method for identifying elite event EE-GM3 and EE-GM1 in biological samples, which method comprises amplifying at least two sequences of nucleic acids present in a biological sample, using a polymerase chain reaction with two primers comprising or consisting (essentially) of the nucleotide sequence of SEQ ID No. 4 and SEQ ID No. 5, respectively, to obtain a DNA fragment of about 263 bp, or with two primers comprising or consisting (essentially) of the nucleotide sequence of SEQ ID No. 5 and SEQ ID No. 7 respectively, to obtain a DNA fragment of about 706 bp, and a polymerase chain reaction with two primers comprising or consisting (essentially) of the nucleotide sequence of SEQ ID No. 16 and SEQ ID No. 17 respectively, to obtain a DNA fragment of about 183 bp. The two polymerase chain reactions may be performed simultaneously or sequentially.

The present invention more specifically relates to a method for identifying elite event EE-GM3 and EE-GM2 in biological samples, which method comprises amplifying at least two sequences of nucleic acids present in a biological sample, using a polymerase chain reaction with two primers comprising or consisting (essentially) of the nucleotide sequence of SEQ ID No. 4 and SEQ ID No. 5 respectively, to obtain a DNA fragment of about 263 bp, or with two primers comprising or consisting (essentially) of the nucleotide sequence of SEQ ID No. 5 and SEQ ID No. 7 respectively, to obtain a DNA fragment of about 706 bp, and a polymerase chain reaction with two primers comprising or consisting (essentially) of the nucleotide sequence of SEQ ID No. 18 and SEQ ID No. 19 respectively, to obtain a DNA fragment of about 151 bp. The two polymerase chain reactions may be performed simultaneously or sequentially.

The present invention further relates to the specific flanking sequences of EE-GM3 described herein in combination with the specific flanking sequences of EE-GM1, which can be used to develop specific identification methods for simultaneous presence of EE-GM3 and EE-GM1 in biological samples. Such combined specific flanking sequences may also be used as reference control material in identification assays. More particularly, the invention relates to the 5' and/or 3' flanking regions of EE-GM3 in combination with the 5' and/or 3' flanking regions of EE-GM1 which can be used for the development of specific primers and probes as further described herein. Also suitable as reference material are nucleic acid molecules, preferably of about 150-850 bp, comprising the sequence which can be amplified by primers comprising or consisting (essentially) of the nucleotide sequence of SEQ ID No. 7 and SEQ ID No. 5 or of SEQ ID No. 4 and SEQ ID No. 5 in combination with nucleic acid molecules comprising the sequence which can be amplified by primers comprising or consisting (essentially) of the nucleotide sequence of SEQ ID No. 16 and SEQ ID No. 17, particularly such nucleic acid molecules are obtained using such primers in material comprising EE-GM3 and EE-GM1.

The present invention further also relates to the specific flanking sequences of EE-GM3 described herein in combination with the specific flanking sequence of EE-GM2, which can be used to develop specific identification methods for simultaneous presence of EE-GM3 and EE-GM2 in biological samples. Such combined specific flanking sequences may also be used as reference control material in identification assays. More particularly, the invention relates to the 5' and/or 3' flanking regions of EE-GM3 in combination with the 5' and/or 3' flanking regions of EE-GM2 which can be used for the development of specific primers and probes as further described herein. Also suitable as reference material are nucleic acid molecules, preferably of about 150-850 bp, comprising the sequence which can be amplified by primers comprising or consisting (essentially) of the nucleotide sequence of SEQ ID No. 7 and SEQ ID No. 5 or of SEQ ID No. 4 and SEQ ID No. 5 in combination with nucleic acid molecules comprising the sequence which can be amplified by primers comprising or consisting (essentially) of the nucleotide sequence of SEQ ID No. 18 and SEQ ID No. 19, particularly such nucleic acid molecules are obtained using such primers in material comprising EE-GM3 and EE-GM2.

The invention further relates to identification methods for the simultaneous presence of EE-GM3 and EE-GM1 in biological samples based on the use of such specific primers or probes. Primers for EE-GM3 detection may comprise, consist or consist essentially of a nucleotide sequence of 17 to about 200 consecutive nucleotides selected from the nucleotide sequence of SEQ ID No 2 from nucleotide 1 to nucleotide 1451 or the complement of the nucleotide sequence of SEQ ID 3 from nucleotide 241 to nucleotide 1408, combined with primers comprising, consisting, or consisting essentially of a nucleotide sequence of 17 to about 200 consecutive nucleotides selected from the nucleotide sequence of SEQ ID No 1, such as a nucleotide sequence of 17 to about 200 consecutive nucleotides selected from the complement of the nucleotide sequence of SEQ ID No 2 from nucleotide 1452 to nucleotide 1843 or the nucleotide sequence of SEQ ID No 3 from nucleotide 1 to nucleotide 240. Primers for EE-GM1 detection may comprise, consist or consist essentially of a nucleotide sequence of 17 to about 200 consecutive nucleotides selected from the nucleotide sequence of SEQ ID No 12 from nucleotide 1 to nucleotide 209 or the complement of the nucleotide sequence of SEQ ID 13 from nucleotide 569 to nucleotide 1000, combined with primers comprising, consisting, or consisting essentially of a nucleotide sequence of 17 to about 200 consecutive nucleotides selected from the nucleotide sequence of SEQ ID No 11, such as a nucleotide sequence of 17 to about 200 consecutive nucleotides selected from the complement of the nucleotide sequence of SEQ ID No 12 from nucleotide 219 to nucleotide 720 or the nucleotide sequence of SEQ ID No 13 from nucleotide 1 to nucleotide 568. Primers may also comprise these nucleotide sequences located at their extreme 3' end, and further comprise unrelated sequences or sequences derived from the mentioned nucleotide sequences, but comprising mismatches.

The invention further relates to identification methods for the simultaneous presence of EE-GM3 and EE-GM2 in biological samples based on the use of such specific primers or probes. Primers for EE-GM3 detection may comprise, consist or consist essentially of a nucleotide sequence of 17 to about 200 consecutive nucleotides as described in the previous paragraph. Primers for EE-GM2 detection may comprise, consist or consist essentially of a nucleotide sequence of 17 to about 200 consecutive nucleotides selected from the nucleotide sequence of SEQ ID No 14 from nucleotide 1 to nucleotide 311 or the complement of the nucleotide sequence of SEQ ID 15 from nucleotide 508 to nucleotide 1880, combined with primers comprising, consisting or consisting essentially of a nucleotide sequence of 17 to about 200 consecutive nucleotides selected from the nucleotide sequence of SEQ ID No 11, such as a nucleotide sequence of 17 to about 200 consecutive nucleotides selected from the complement of the nucleotide sequence of SEQ ID No 14 from nucleotide 312 to nucleotide 810 or the nucleotide sequence of SEQ ID No 15 from nucleotide 1 to nucleotide 507. Primers may also comprise these nucleotide sequences located at their extreme 3' end, and further comprise unrelated sequences or sequences derived from the mentioned nucleotide sequences, but comprising mismatches.

The invention further relates to kits for identifying elite events EE-GM3 and EE-GM1 in biological samples, said kits comprising at least one primer or probe which specifically recognizes the 5' or 3' flanking region of the foreign DNA comprising herbicide tolerance genes in EE-GM3 and at least one primer or probe which specifically recognizes the 5' or 3' flanking region of the foreign DNA comprising herbicide tolerance genes in EE-GM1.

The invention further relates to kits for identifying elite events EE-GM3 and EE-GM2 in biological samples, said kits comprising at least one primer or probe which specifically recognizes the 5' or 3' flanking region of the foreign DNA comprising herbicide tolerance genes in EE-GM3 and at least one primer or probe which specifically recognizes the 5' or 3' flanking region of the foreign DNA comprising a herbicide tolerance gene in EE-GM2.

The kits of the invention may comprise, in addition to a primer which specifically recognizes the 5' or 3' flanking region of EE-GM3 and the 5' or 3' flanking region of EE-GM1, a further primer which specifically recognizes a sequence within the foreign DNA comprising herbicide tolerance genes of EE-GM3 and a further primer which specifically recognizes a sequence within the foreign DNA comprising herbicide tolerance genes of EE-GM1, for use in a PCR Identification Protocol.

The kits of the invention may also comprise, in addition to a primer which specifically recognizes the 5' or 3' flanking region of EE-GM3 and the 5' or 3' flanking region of EE-GM2, a further primer which specifically recognizes a sequence within the foreign DNA comprising herbicide tolerance genes of EE-GM3 and a further primer which specifically recognizes a sequence within the foreign DNA comprising herbicide tolerance genes of EE-GM2, for use in a PCR Identification Protocol.

The primer recognizing the 3' flanking region of EE-GM3 may comprise the nucleotide sequence of SEQ ID No. 5 and the primer recognizing the transgenes or foreign DNA comprising herbicide tolerance genes of EE-GM3 may comprises the nucleotide sequence of SEQ ID No. 4 or 7, or any other primer or primer combination for EE-GM3 detection as described herein, in combination with a primer recognizing the 5' flanking region of EE-GM1 which may comprise the nucleotide sequence of SEQ ID No. 16 and a primer recognizing the transgenes of foreign DNA comprising the herbicide tolerance gene of EE-GM1 may comprise the nucleotide sequence of SEQ ID No 17.

The primer recognizing the 3' flanking region of EE-GM3 may comprise the nucleotide sequence of SEQ ID No. 5 and the primer recognizing the transgenes or foreign DNA comprising herbicide tolerance genes of EE-GM3 may comprises the nucleotide sequence of SEQ ID No. 4 or 7, or any other primer or primer combination for EE-GM3 detection as described herein, in combination with a primer recognizing the 5' flanking region of EE-GM2 which may comprise the nucleotide sequence of SEQ ID No. 18 and a primer recognizing the transgenes of foreign DNA comprising the herbicide tolerance gene of EE-GM2 may comprise the nucleotide sequence of SEQ ID No 19.

The invention further relates to a kit for identifying elite event EE-GM3 and EE-GM1 in biological samples, said kit comprising PCR primers comprising or consisting (essentially) of the nucleotide sequence of SEQ ID No. 5 and SEQ ID No. 4 and PCR primers comprising or consisting (essentially) of the nucleotide sequence of SEQ ID 16 and SEQ ID 17 for use in the EE-GM3/EE-GM1 PCR based identification.

The invention further relates to a kit for identifying elite event EE-GM3 and EE-GM2 in biological samples, said kit comprising PCR primers comprising or consisting (essentially) of the nucleotide sequence of SEQ ID No. 5 and SEQ ID No. 4 and PCR primers comprising or consisting (essentially) of the nucleotide sequence of SEQ ID 18 and SEQ ID 19 for use in the EE-GM3/EE-GM2 PCR based identification.

The invention also relates to a kit for identifying elite event EE-GM3 and EE-GM1 in biological samples, which kit comprises two specific probes, a first probe comprising or consisting (essentially) of a sequence which corresponds (or is complementary to) a sequence having between 80% and 100% sequence identity with a specific region of EE-GM3 and a second probe comprising or consisting (essentially) of a sequence which corresponds (or is complementary to) a sequence having between 80% and 100% sequence identity with a specific region of EE-GM1. Preferably, the sequence of the first probe corresponds to a specific region comprising part of the 5' or 3' flanking region of EE-GM3 and the second probe corresponds to a specific region comprising part of the 5' or 3' flanking region of EE-GM1. Most preferably the EE-GM3 specific probe comprises or consists (essentially) of (or is complementary to) a sequence having between 80% and 100% sequence identity to the sequence between nucleotide 1441 to 1462 of SEQ ID No 2 or a sequence having between 80% and 100% sequence identity to the sequence between nucleotide 220 to 260 of ID No. 3 and the EE-GM1 specific probe comprises, consists (essentially) of (or is complementary to) a sequence having between 80% and 100% sequence identity to the sequence between nucleotide 199 to 220 of SEQ ID No 12 or a sequence having between 80% and 100% sequence identity to the sequence between nucleotide 558 to 579 of ID No. 13.

The invention also relates to a kit for identifying elite event EE-GM3 and EE-GM2 in biological samples, which kit comprises two specific probes, a first probe comprising or consisting (essentially) of a sequence which corresponds (or is complementary to) a sequence having between 80% and 100% sequence identity with a specific region of EE-GM3 and a second probe comprising or consisting (essentially) of a sequence which corresponds (or is complementary to) a sequence having between 80% and 100% sequence identity with a specific region of EE-GM2. Preferably, the sequence of the first probe corresponds to a specific region comprising part of the 5' or 3' flanking region of EE-GM3 and the second probe corresponds to a specific region comprising part of the 5' or 3' flanking region of EE-GM2. Most preferably the EE-GM3 specific probe comprises or consists (essentially) of (or is complementary to) a sequence having between 80% and 100% sequence identity to the sequence between nucleotide 1441 to 1462 of SEQ ID No 2 or a sequence having between 80% and 100% sequence identity to the sequence between nucleotide 220 to 260 of ID No. 3 and the EE-GM2 specific probe comprises or consists (essentially) of (or is complementary to) a sequence having between 80% and 100% sequence identity to the sequence between nucleotide 301 to 322 of SEQ ID No 14 or a sequence having between 80% and 100% sequence identity to the sequence between nucleotide 497 to 518 of ID No. 15.

According to another aspect of the invention, DNA sequences are disclosed comprising a junction site of the event and sufficient length of polynucleotides of both the soybean genomic DNA and the foreign DNA comprising herbicide tolerance genes (transgene) of each event, so as to be useful as primer or probe for the detection of EE-GM3 and EE-GM1. Such sequences may comprise at least 9 nucleotides of the soybean genomic DNA and a similar number of nucleotides of the foreign DNA comprising herbicide tolerance genes (transgene) of EE-GM3 or EE-GM1, at each side of the junction site respectively. Most preferably, such DNA sequences comprise at least 9 nucleotides of the soybean genomic DNA and a similar number of nucleotides of the foreign DNA comprising herbicide tolerance genes contiguous with the junction site in SEQ ID NO: 2 or SEQ ID NO: 3 and at least 9 nucleotides of the soybean genomic DNA and a similar number of nucleotides of the foreign DNA comprising herbicide tolerance genes contiguous with the junction site in SEQ ID NO: 12 or SEQ ID NO: 13.

According to yet another aspect of the invention, DNA sequences are disclosed comprising a junction site of the event and sufficient length of polynucleotides of both the soybean genomic DNA and the foreign DNA comprising herbicide tolerance genes (transgene) of each event, so as to be useful as primer or probe for the detection of EE-GM3 and EE-GM2. Such sequences may comprise at least 9 nucleotides of the soybean genomic DNA and a similar number of nucleotides of the foreign DNA comprising herbicide tolerance genes (transgene) of EE-GM3 or EE-GM2, at each side of the insertion site respectively. Most preferably, such DNA sequences comprise at least 9 nucleotides of the soybean genomic DNA and a similar number of nucleotides of the foreign DNA comprising herbicide tolerance genes contiguous with the junction site in SEQ ID NO: 2 or SEQ ID NO: 3 and at least 9 nucleotides of the soybean genomic DNA and a similar number of nucleotides of the foreign DNA comprising herbicide tolerance genes contiguous with the junction site in SEQ ID NO: 14 or SEQ ID NO: 15.

The methods and kits encompassed by the present invention can be used for different purposes such as, but not limited to the following: to identify the presence or determine the (lower) threshold of EE-GM3 and EE-GM1 or of EE-GM3 and EE-GM2 in plants, plant material or in products such as, but not limited to food or feed products (fresh or processed) comprising or derived from plant material; additionally or alternatively, the methods and kits of the present invention can be used to identify transgenic plant material for purposes of segregation between transgenic and non-transgenic material; additionally or alternatively, the methods and kits of the present invention can be used to determine the quality (i.e., percentage pure material) of plant material comprising EE-GM3 and EE-GM1 or EE-GM3 and EE-GM1.

The invention further relates to the 5' and/or 3' flanking regions of EE-GM3 GM3 in combination with specific primers and probes developed from the 5' and/or 3' flanking sequences of EE-GM1 or EE-GM2, as well as to the specific primers and probes developed from the 5' and/or 3' flanking sequences of EE-GM3 in combination with specific primers and probes developed from the 5' and/or 3' flanking sequences of EE-GM1 or EE-GM2.

The invention also relates to genomic DNA obtained from plants comprising elite events EE-GM3 and EE-GM1 or plants comprising elite events EE-GM3 and EE-GM2. Such genomic DNA may be used as reference control material in the identification assays herein described.

Also provided herein is a transgenic herbicide tolerant soybean plant, or cells, parts, seeds or progeny thereof, each comprising at least two elite events, said first elite event comprising a foreign DNA comprising:
   i) a first chimeric gene which comprises a modified epsps gene from *Zea mays* encoding a glyphosate tolerant EPSPS enzyme under the control of a plant-expressible promoter, and
   ii) a second chimeric gene which comprises a modified hppd gene from *Pseudomonas fluorescens* encoding an HPPD inhibitor herbicide tolerant enzyme under the control of a plant-expressible promoter, and said second elite event comprises a (third) chimeric gene which comprises a modified glufosinate tolerance gene derived from *Streptomyces viridochromogenes* encoding a glufosinate (or phosphinothricin) acetyltransferase enzyme under the control of a plant-expressible promoter.

In one embodiment, said first elite event comprises nucleotides 1 to 1451 of SEQ ID No 2 immediately upstream of and contiguous with said foreign DNA and nucleotides 241 to 1408 of SEQ ID No 3 immediately downstream of and contiguous with said foreign DNA, and said second event comprises nucleotides 1 to 209 of SEQ ID No 12 immediately upstream of and contiguous with said foreign DNA and nucleotides 569 to 1000 of SEQ ID No 13 immediately downstream of and contiguous with said foreign DNA, or said second event comprises nucleotides 1 to 311 of SEQ ID No 14 immediately upstream of and contiguous with said foreign DNA and nucleotides 508 to 1880 of SEQ ID No 15 immediately downstream of and contiguous with said foreign DNA.

In a further embodiment, said elite event is obtainable by breeding with a soybean plant grown from reference seed comprising said events having been deposited at the ATCC under deposit number PTA-11041 or PTA-11042, or obtainable from reference seed comprising said first event having been deposited at NCIMB under accession number NCIMB 41659, and obtainable from reference seed comprising said second event having been deposited at NCIMB under accession number NCIMB 41658 or NCIMB accession number NCIMB 41660.

In another embodiment, the genomic DNA of said soybean plant, or cells, parts, seeds or progeny thereof when analyzed using the elite event identification protocol for said first elite event with two primers comprising the nucleotide sequence of SEQ ID No 4 and SEQ ID No 5 respectively, yields a DNA fragment of about 263 by or 263 bp, and when analyzed using the elite event identification protocol for said second elite event with two primers comprising the nucleotide sequence of SEQ ID No 16 and SEQ ID No 17 respectively, yields a DNA fragment of about 183 bp or 183 bp, or with two primers comprising the nucleotide sequence of SEQ ID No 18 and SEQ ID No 19 respectively, yields a DNA fragment of about 151 bp or 151 bp.

Also provided herein is a method for identifying a transgenic soybean plant, or cells, parts, seed or progeny thereof comprising 2 elite events, wherein said plant, cells, seed, or progeny are tolerant to glyphosate, glufosinate and an HPPD inhibitor herbicide (such as isoxaflutole), in biological samples, said method comprising amplifying a DNA fragment of between 100 and 500 bp from a nucleic acid of said first event present in biological samples using a polymerase chain reaction with at least two primers, one of said primers recognizing the 5' flanking region of the first elite event specified above, said 5' flanking region comprising the nucleotide sequence of SEQ ID No 2 from nucleotide 1 to nucleotide 1451, or the 3' flanking region of said first elite event, said 3' flanking region comprising the nucleotide sequence of the complement of SEQ ID No 3 from nucleotide 241 to nucleotide 1408, the other primer of said primers recognizing a sequence within the foreign DNA of said first event comprising the nucleotide sequence of the complement of SEQ ID No 2 from nucleotide 1452 to nucleotide 1843 or the nucleotide sequence of SEQ ID No 3 from nucleotide 1 to nucleotide 240, and comprising amplifying a DNA fragment of between 50 and 1000 bp, or between 100 and 500 bp from a nucleic acid of said second event present in biological samples using a polymerase chain reaction with at least two primers, one of said primers recognizing the 5' flanking region of the second elite event specified above, said 5' flanking region comprising the nucleotide sequence of nucleotides 1 to 209 of SEQ ID No 12, or the 3' flanking region of said second elite event, said 3' flanking region comprising the nucleotide sequence of the complement of nucleotides 569 to 1000 of SEQ ID No 13, the other primer of said primers recognizing a sequence within the foreign DNA of said second event comprising the nucleotide sequence of the complement of SEQ ID No 12 from nucleotide 210 to nucleotide 720 or the nucleotide sequence of SEQ ID No 13 from nucleotide 1 to nucleotide 568.

Also provided herein is a method for identifying a transgenic soybean plant, or cells, parts, seed or progeny thereof comprising 2 elite events, wherein said plant, cells, seed, or progeny are tolerant to glyphosate, glufosinate and/or an HPPD inhibitor herbicide (such as isoxaflutole), in biological samples, said method comprising amplifying a DNA fragment of between 50 and 1000 or between 100 and 500 bp from a nucleic acid of said first event present in biological samples using a polymerase chain reaction with at least two primers, one of said primers recognizing the 5' flanking region of the first elite event specified above, said 5' flanking region comprising the nucleotide sequence of SEQ ID No 2 from nucleotide 1 to nucleotide 1451, or the 3' flanking region of said first elite event, said 3' flanking region comprising the nucleotide sequence of the complement of SEQ ID No 3 from nucleotide 241 to nucleotide 1408, the other primer of said primers recognizing a sequence within the foreign DNA of said first event comprising the nucleotide sequence of the complement of SEQ ID No 2 from nucleotide 1452 to nucleotide 1843 or the nucleotide sequence of SEQ ID No 3 from nucleotide 1 to nucleotide 240, and comprising amplifying a DNA fragment of between 50 and 1000 bp or between 100 and 500 bp from a nucleic acid of said second event present in biological samples using a polymerase chain reaction with at least two primers, one of said primers recognizing the 5' flanking region of the second elite event specified above, said 5' flanking region comprising the nucleotide sequence of nucleotides 1 to 311 of SEQ ID No 14, or the 3' flanking region of said second elite event, said 3' flanking region comprising the nucleotide sequence of the complement of nucleotides 508 to 1880 of SEQ ID No 15, the other primer of said primers recognizing a sequence within the foreign DNA of said second event comprising the nucleotide sequence of the complement of SEQ ID No 14 from nucleotide 312 to nucleotide 810 or the nucleotide sequence of SEQ ID No 15 from nucleotide 1 to nucleotide 507.

Also provided herein is a kit for identifying a transgenic soybean plant, or cells, parts, seed or progeny thereof comprising 2 elite events and being tolerant to glyphosate, glufosinate and an HPPD inhibitor herbicide (such as isoxaflutole), in biological samples, said kit comprising one primer recognizing the 5' flanking region of the first elite event specified above, said 5' flanking region comprising the nucleotide sequence of SEQ ID No 2 from nucleotide 1 to nucleotide 1451, or one primer recognizing the 3' flanking region of said first elite event, said 3' flanking region comprising the nucleotide sequence of the complement of SEQ ID No 3 from nucleotide 241 to nucleotide 1408, and one primer recognizing a sequence within the foreign DNA of said first event, said foreign DNA comprising the nucleotide sequence of the complement of SEQ ID No. 2 from nucleotide 1452 to nucleotide 1843 or the nucleotide sequence of SEQ ID No 3 from nucleotide 1 to nucleotide 240, and said kit comprising one primer recognizing the 5' flanking region of the second elite event specified above, said 5' flanking region comprising the nucleotide sequence of nucleotides 1 to 209 of SEQ ID No 12, or one primer recognizing the 3' flanking region of said second elite event, said 3' flanking region comprising the nucleotide sequence of the complement of nucleotides 569 to 1000 of SEQ ID No 13, the other primer of said primers recognizing a sequence within the foreign DNA of said second event comprising the nucleotide sequence of the complement of SEQ ID No 12 from nucleotide 210 to nucleotide 720 or the nucleotide sequence of SEQ ID No 13 from nucleotide 1 to nucleotide 568.

Also provided herein is a kit for identifying a transgenic soybean plant, or cells, parts, seed or progeny thereof comprising 2 elite events and being tolerant to glyphosate, glufosinate and an HPPD inhibitor herbicide (such as isoxaflutole), in biological samples, said kit comprising one primer recognizing the 5' flanking region of the first elite event specified above, said 5' flanking region comprising the nucleotide sequence of SEQ ID No 2 from nucleotide 1 to nucleotide 1451, or one primer recognizing the 3' flanking region of said first elite event, said 3' flanking region comprising the nucleotide sequence of the complement of SEQ ID No 3 from nucleotide 241 to nucleotide 1408, and one primer recognizing a sequence within the foreign DNA of said first event, said foreign DNA comprising the nucleotide sequence of the complement of SEQ ID No. 2 from nucleotide 1452 to nucleotide 1843 or the nucleotide sequence of SEQ ID No 3 from nucleotide 1 to nucleotide 240, and said kit comprising one primer recognizing the 5' flanking region of the second elite event specified above, said 5' flanking region comprising the nucleotide sequence of nucleotides 1 to 311 of SEQ ID No 14, or the 3' flanking region of said second elite event, said 3' flanking region comprising the nucleotide sequence of the complement of nucleotides 508 to 1880 of SEQ ID No 15, the other primer of said primers recognizing a sequence within the foreign DNA of said second event comprising the nucleotide sequence of the complement of SEQ ID No 14 from nucleotide 312 to nucleotide 810 or the nucleotide sequence of SEQ ID No 15 from nucleotide 1 to nucleotide 507.

Also provided herein is a soybean plant, plant cell, tissue, or seed, comprising in their genome a nucleic acid molecule comprising a nucleotide sequence with at least 97, 98, or at least 99% or 99.5% sequence identity to the nucleotide sequence of SEQ ID No. 20 from nucleotide position 1452 to nucleotide position 16638, the nucleotide sequence of SEQ ID No. 20 from nucleotide position 2257 to nucleotide position 16601 or their complement, or a nucleotide sequence with at least 97, 98, or at least 99% or 99.5% sequence identity to SEQ ID No. 20 or the complement thereof, and comprising in their genome a nucleic acid molecule comprising a nucleotide sequence with at least 97, 98, or at least 99% or 99.5% sequence identity to the nucleotide sequence of EE-GM1 or EE-GM2 or the complement thereof, reference seed comprising EE-GM1 having been deposited under deposit number NCIMB 41658, and reference seed comprising EE-GM2 having been deposited under deposit number NCIMB 41660. In one embodiment of this invention, the nucleotide sequence of EE-GM1 or EE-GM2 in said plant, plant cell, tissue, or seed, is the DNA sequence (such as the foreign DNA sequence) in SEQ ID No 12 or 13, or the DNA sequence (such as the foreign DNA sequence) in SEQ ID No 14 or 15, or the DNA sequence in the plant genome (such as in the deposited seeds comprising EE-GM1 or EE-GM2 of the invention) comprising SEQ ID No 12 and 13 between the first nucleotide of the sequence of SEQ ID No 12 and the last nucleotide of the sequence of SEQ ID No 13, or the DNA sequence in the plant genome comprising SEQ ID No 14 and 15 between the first nucleotide of the sequence of SEQ ID No 14 and the last nucleotide of the sequence of SEQ ID No 15.

One embodiment of this invention provides a soybean plant, plant cell, tissue, or seed, comprising in their genome a nucleic acid molecule hybridizing to the nucleotide sequence of SEQ ID No 1 or the complement thereof, or hybridizing to the nucleotide sequence of SEQ ID No. 20 from nucleotide position 1452 to nucleotide position 16638 or the complement thereof, or hybridizing to the nucleotide sequence of SEQ ID No. 20 or the complement thereof, and comprising in their genome a nucleic acid molecule hybridizing to the nucleotide sequence of EE-GM1 or EE-GM2 or the complement thereof, reference seed comprising EE-GM1 having been deposited under deposit number NCIMB 41658, and reference seed comprising EE-GM2 having been deposited under deposit number NCIMB 41660. In one embodiment of this invention, the nucleotide sequence of EE-GM1 or EE-GM2 in said plant, plant cell, tissue, or seed, is the foreign DNA in SEQ ID No 12 or 13, or the foreign DNA in SEQ ID No 14 or 15, or the foreign DNA sequence in the plant genome (such as in the deposited seeds comprising EE-GM1 or EE-GM2 of the invention) comprising SEQ ID No 12 and 13 between the first nucleotide of the sequence of SEQ ID No 12 and the last nucleotide of the sequence of SEQ ID No 13, or the foreign DNA sequence in the plant genome comprising SEQ ID No 14 and 15 between the first nucleotide of the sequence of SEQ ID No 14 and the last nucleotide of the sequence of SEQ ID No 15.

BRIEF DESCRIPTION OF THE DRAWINGS

The following Examples, not intended to limit the invention to specific embodiments described, may be understood in conjunction with the accompanying Figures, incorporated herein by reference, in which.

DETAILED DESCRIPTION OF THE PREFERRED EMBODIMENTS OF THE INVENTION

Figure 1:
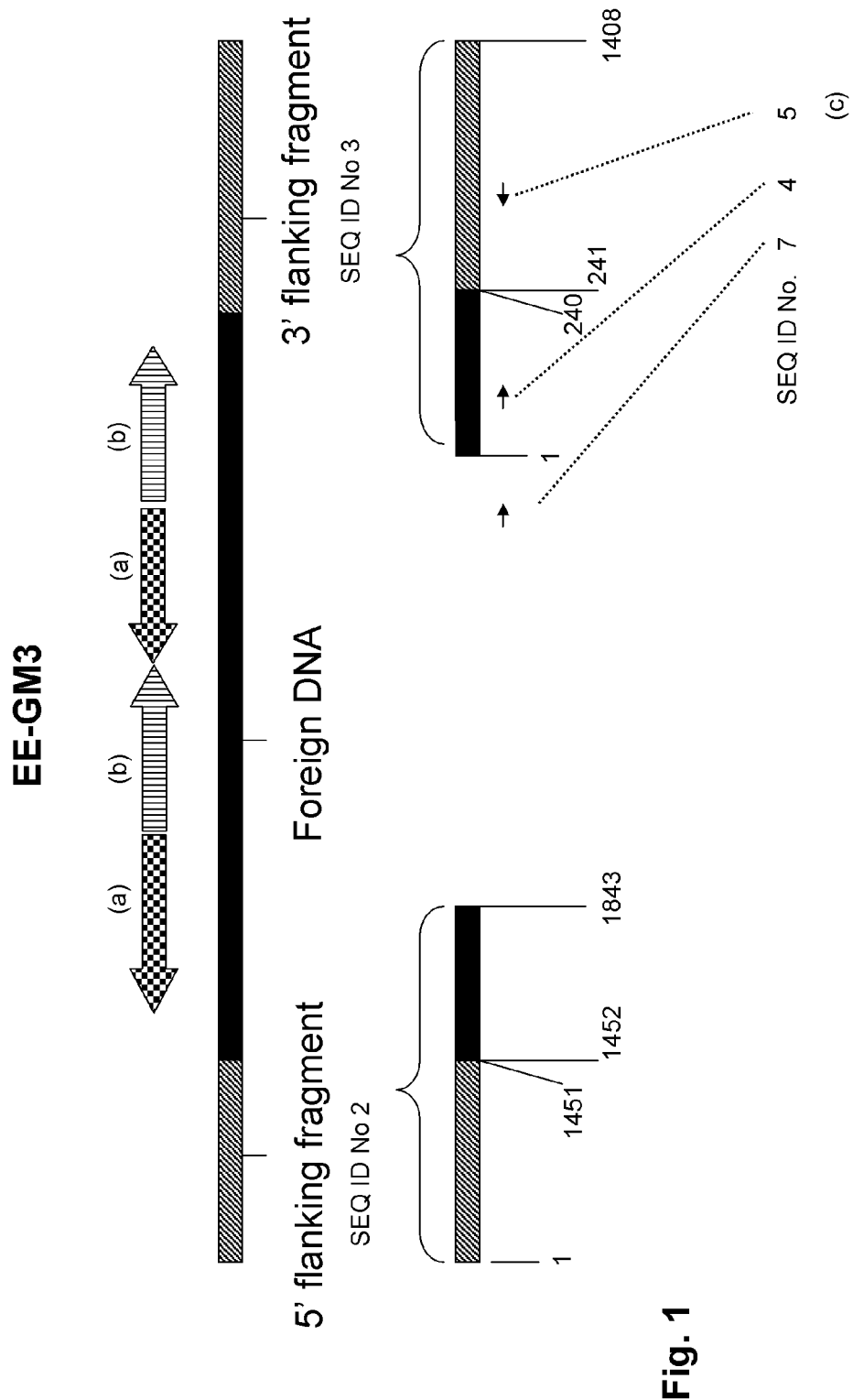
FIG. 1: Schematic representation of the relationship between the cited nucleotide sequences and primers for elite event EE-GM3. black bar: foreign DNA; hatched bar: DNA of plant origin; checkered arrow (a): chimeric HPPD PF W366 encoding gene (see Table 1 for composition of the chimeric gene); hatched arrow (b): chimeric 2mEPSPS encoding gene (see Table 1 for composition of the chimeric gene); black arrows: oligonucleotide primers, the figures under the bars represent nucleotide positions; (c) refers to complement of the indicated nucleotide sequence; Note: the scheme is not drawn to scale.

The incorporation of a recombinant DNA molecule in the plant genome typically results from transformation of a cell or tissue. The particular site of incorporation is usually due to random integration.

The DNA introduced into the plant genome as a result of transformation of a plant cell or tissue with a recombinant DNA or "transforming DNA", and originating from such transforming DNA is hereinafter referred to as "foreign DNA" comprising one or more "transgenes". The transgenes of EE-GM3 are the glyphosate and HPPD inhibitor herbicide tolerance genes. "Plant DNA" in the context of the present invention will refer to DNA originating from the plant which is transformed. Plant DNA will usually be found in the same genetic locus in the corresponding wild-type plant. The foreign DNA can be characterized by the location and the configuration at the site of incorporation of the recombinant DNA molecule in the plant genome. The site in the plant genome where a recombinant DNA has been inserted is also referred to as the "insertion site" or "target site". Insertion of the recombinant DNA into the region of the plant genome referred to as "pre-insertion plant DNA" can be associated with a deletion of plant DNA, referred to as "target site deletion". A "flanking region" or "flanking sequence" as used herein refers to a sequence of at least 20 bp, preferably at least 50 bp, and up to 5000 bp of DNA different from the introduced DNA, preferably DNA from the plant genome which is located either immediately upstream of and contiguous with or immediately downstream of and contiguous with the foreign DNA. Transformation procedures leading to random integration of the foreign DNA will result in transformants with different flanking regions, which are characteristic and unique for each transformant. When the recombinant DNA is introduced into a plant through traditional crossing, its insertion site in the plant genome, or its flanking regions will generally not be changed.

An "isolated nucleic acid (sequence)" or "isolated DNA (sequence)", as used herein, refers to a nucleic acid or DNA (sequence) which is no longer in the natural environment it was isolated from, e.g., the nucleic acid sequence in another bacterial host or in a plant genome, or a nucleic acid or DNA fused to DNA or nucleic acid from another origin, such as when contained in a chimeric gene under the control of a plant-expressible promoter.

An event is defined as a (artificial) genetic locus that, as a result of genetic engineering, carries a foreign DNA or transgene comprising at least one copy of a gene of interest or of the genes of interest. The typical allelic states of an event are the presence or absence of the foreign DNA.

An event is characterized phenotypically by the expression of the transgene. At the genetic level, an event is part of the genetic make-up of a plant. At the molecular level, an event can be characterized by the restriction map (e.g., as determined by Southern blotting), by the upstream and/or downstream flanking sequences of the transgene, the location of molecular markers and/or the molecular configuration of the transgene. Usually transformation of a plant with a transforming DNA comprising at least one gene of interest leads to a population of transformants comprising a multitude of separate events, each of which is unique. An event is characterized by the foreign DNA and at least one of the flanking sequences.

An elite event, as used herein, is an event which is selected from a group of events, obtained by transformation with the same transforming DNA, based on the expression and stability of the transgene(s) and its compatibility with optimal agronomic characteristics of the plant comprising it. Thus the criteria for elite event selection are one or more, preferably two or more, advantageously all of the following:

a) that the presence of the foreign DNA does not compromise other desired characteristics of the plant, such as those relating to agronomic performance or commercial value;

b) that the event is characterized by a well defined molecular configuration which is stably inherited and for which appropriate tools for identity control can be developed;

c) that the gene(s) of interest show(s) a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use.

It is preferred that the foreign DNA is associated with a position in the plant genome that allows easy introgression into desired commercial genetic backgrounds.

The status of an event as an elite event is confirmed by introgression of the elite event in different relevant genetic backgrounds and observing compliance with one, two or all of the criteria e.g. a), b) and c) above.

An "elite event" thus refers to a genetic locus comprising a foreign DNA, which meets the above-described criteria. A plant, plant material or progeny such as seeds can comprise one or more elite events in its genome.

The tools developed to identify an elite event or the plant or plant material comprising an elite event, or products which comprise plant material comprising the elite event, are based on the specific genomic characteristics of the elite event, such as, a specific restriction map of the genomic region comprising the foreign DNA, molecular markers or the sequence of the flanking region(s) of the foreign DNA.

Once one or both of the flanking regions of the foreign DNA have been sequenced, primers and probes can be developed which specifically recognize this (these) sequence(s) in the nucleic acid (DNA or RNA) of a sample by way of a molecular biological technique. For instance a PCR method can be developed to identify the elite event in biological samples (such as samples of plants, plant material or products comprising plant material). Such a PCR is based on at least two specific "primers", one recognizing a sequence within the 5' or 3' flanking region of the elite event and the other recognizing a sequence within the foreign DNA. The primers preferably have a sequence of between 15 and 35 nucleotides which under optimized PCR conditions "specifically recognize" a sequence within the 5' or 3' flanking region of the elite event and the foreign DNA of the elite event respectively, so that a specific fragment ("integration fragment" or discriminating amplicon) is amplified from a nucleic acid sample comprising the elite event. This means that only the targeted integration fragment, and no other sequence in the plant genome or foreign DNA, is amplified under optimized PCR conditions.

PCR primers suitable for identification of EE-GM3 may be the following:
 oligonucleotides ranging in length from 17 nt to about 200 nt, comprising a nucleotide sequence of at least 17 consecutive nucleotides, preferably 20 consecutive nucleotides, selected from the plant DNA in the 5' flanking sequence (SEQ ID No 2 from nucleotide 1 to nucleotide 1451) at their 3' end (primers recognizing 5' flanking sequences); or
 oligonucleotides ranging in length from 17 nt to about 200 nt, comprising a nucleotide sequence of at least 17 consecutive nucleotides, preferably 20 consecutive nucleotides, selected from the plant DNA in the 3' flanking sequence (complement of SEQ ID No 3 from nucleotide 241 to nucleotide 1408) at their 3' end (primers recognizing 3' flanking sequences); or
 oligonucleotides ranging in length from 17 nt to about 200 nt, comprising a nucleotide sequence of at least 17 consecutive nucleotides, preferably 20 consecutive nucleotides, selected from the inserted DNA sequences (complement of SEQ ID No 2 from nucleotide 1452 to nucleotide 1843) at their 3' end (primers recognizing foreign DNA); or
 oligonucleotides ranging in length from 17 nt to about 200 nt, comprising a nucleotide sequence of at least 17 consecutive nucleotides, preferably 20 consecutive nucleotides, selected from the inserted DNA sequences (SEQ ID No 3 from nucleotide 1 to nucleotide 240); or
 suitable oligonucleotides ranging in length from 17 nt to about 200 nt, comprising a nucleotide sequence of at least 17 consecutive nucleotides, preferably 20 consecutive nucleotides, selected from the nucleotide sequence of the inserted DNA fragment or its complement (SEQ ID No 1 or SEQ ID No 20 from nucleotide position 1452 to 16638).

The primers may of course be longer than the mentioned 17 consecutive nucleotides, and may, e.g., be 20, 21, 30, 35, 50, 75, 100, 150, 200 nt long or even longer. The primers may entirely consist of nucleotide sequence selected from the mentioned nucleotide sequences of flanking sequences and foreign DNA sequences. However, the nucleotide sequence of the primers at their 5' end (i.e. outside of the 3'-located 17 consecutive nucleotides) is less critical. Thus, the 5' sequence of the primers may comprise or consist of a nucleotide sequence selected from the flanking sequences or foreign DNA, as appropriate, but may contain several (e.g., 1, 2, 5, or 10) mismatches. The 5' sequence of the primers may even entirely be a nucleotide sequence unrelated to the flanking sequences or foreign DNA, such as, e.g., a nucleotide sequence representing one or more restriction enzyme recognition sites. Such unrelated sequences or flanking DNA sequences with mismatches should preferably be not longer than 100, more preferably not longer than 50 or even 25 nucleotides.

Moreover, suitable primers may comprise, consist or consist essentially of a nucleotide sequence at their 3' end spanning the joining region between the plant DNA derived sequences and the foreign DNA sequences (located at nucleotides 1451-1452 in SEQ ID No 2 and nucleotides 240-241 in SEQ ID No 3 for EE-GM3) provided the mentioned 3'-located 17 consecutive nucleotides are not derived exclusively from either the foreign DNA or plant-derived sequences in SEQ ID No 2 or 3.

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides with their complementary nucleotide according to Chargaff's rules (A⇔T; G⇔C) and reading the sequence in the 5' to 3' direction, i.e., in opposite direction of the represented nucleotide sequence.

Examples of suitable primers for EE-GM3 are the oligonucleotide sequences of SEQ ID No 5 (3' flanking sequence recognizing primer), SEQ ID No 4 (foreign DNA recognizing primer for use with a 3' flanking sequence recognizing primers), or SEQ ID No 7 (foreign DNA recognizing primer for use with a 3' flanking sequence recognizing primers).

Other examples of suitable oligonucleotide primers for EE-GM3 comprise at their 3' end the following sequences or consist (essentially) of such sequences:

a. 5' flanking sequence recognizing primers:
 the nucleotide sequence of SEQ ID No 2 from nucleotide 264 to nucleotide 283
 the nucleotide sequence of SEQ ID No 2 from nucleotide 266 to nucleotide 285
 the nucleotide sequence of SEQ ID No 2 from nucleotide 1240 to nucleotide 1259
 the nucleotide sequence of SEQ ID No 2 from nucleotide 265 to nucleotide 285
 the nucleotide sequence of SEQ ID No 2 from nucleotide 265 to nucleotide 283
 the nucleotide sequence of SEQ ID No 2 from nucleotide 1239 to nucleotide 1259
 the nucleotide sequence of SEQ ID No 2 from nucleotide 1241 to nucleotide 1259
 the nucleotide sequence of SEQ ID No 2 from nucleotide 1244 to nucleotide 1263
 the nucleotide sequence of SEQ ID No 2 from nucleotide 1248 to nucleotide 1267
 the nucleotide sequence of SEQ ID No 2 from nucleotide 1250 to nucleotide 1269
 the nucleotide sequence of SEQ ID No 2 from nucleotide 262 to nucleotide 279
 the nucleotide sequence of SEQ ID No 2 from nucleotide 263 to nucleotide 279
 the nucleotide sequence of SEQ ID No 2 from nucleotide 264 to nucleotide 285
 the nucleotide sequence of SEQ ID No 2 from nucleotide 266 to nucleotide 283 the nucleotide sequence of SEQ ID No 2 from nucleotide 1238 to nucleotide 1259
the nucleotide sequence of SEQ ID No 2 from nucleotide 1242 to nucleotide 1259
the nucleotide sequence of SEQ ID No 2 from nucleotide 1243 to nucleotide 1263
the nucleotide sequence of SEQ ID No 2 from nucleotide 1245 to nucleotide 1263
the nucleotide sequence of SEQ ID No 2 from nucleotide 1247 to nucleotide 1267
the nucleotide sequence of SEQ ID No 2 from nucleotide 1249 to nucleotide 1269
the nucleotide sequence of SEQ ID No 2 from nucleotide 1249 to nucleotide 1267
the nucleotide sequence of SEQ ID No 2 from nucleotide 263 to nucleotide 285
the nucleotide sequence of SEQ ID No 2 from nucleotide 267 to nucleotide 283
the nucleotide sequence of SEQ ID No 2 from nucleotide 1242 to nucleotide 1263
the nucleotide sequence of SEQ ID No 2 from nucleotide 1243 to nucleotide 1259
the nucleotide sequence of SEQ ID No 2 from nucleotide 1246 to nucleotide 1267
the nucleotide sequence of SEQ ID No 2 from nucleotide 1246 to nucleotide 1263
the nucleotide sequence of SEQ ID No 2 from nucleotide 1248 to nucleotide 1269
the nucleotide sequence of SEQ ID No 2 from nucleotide 1250 to nucleotide 1271
the nucleotide sequence of SEQ ID No 2 from nucleotide 1250 to nucleotide 1267
the nucleotide sequence of SEQ ID No 2 from nucleotide 1241 to nucleotide 1263
the nucleotide sequence of SEQ ID No 2 from nucleotide 1245 to nucleotide 1267
the nucleotide sequence of SEQ ID No 2 from nucleotide 1247 to nucleotide 1269
the nucleotide sequence of SEQ ID No 2 from nucleotide 1247 to nucleotide 1263
the nucleotide sequence of SEQ ID No 2 from nucleotide 1249 to nucleotide 1271
the nucleotide sequence of SEQ ID No 2 from nucleotide 1242 to nucleotide 1261
the nucleotide sequence of SEQ ID No 2 from nucleotide 1241 to nucleotide 1261
the nucleotide sequence of SEQ ID No 2 from nucleotide 1243 to nucleotide 1261
the nucleotide sequence of SEQ ID No 2 from nucleotide 1240 to nucleotide 1261
the nucleotide sequence of SEQ ID No 2 from nucleotide 1244 to nucleotide 1261
the nucleotide sequence of SEQ ID No 2 from nucleotide 1239 to nucleotide 1261
the nucleotide sequence of SEQ ID No 2 from nucleotide 1245 to nucleotide 1261 b. foreign DNA sequence recognizing primers for use with 5' flanking sequence recognizing primers:
the complement of the nucleotide sequence of SEQ ID No 2 from nucleotide 1732 to nucleotide 1751
the complement of the nucleotide sequence of SEQ ID No 2 from nucleotide 1735 to nucleotide 1754
the complement of the nucleotide sequence of SEQ ID No 2 from nucleotide 1731 to nucleotide 1750
the complement of the nucleotide sequence of SEQ ID No 2 from nucleotide 1732 to nucleotide 1750
the complement of the nucleotide sequence of SEQ ID No 2 from nucleotide 1732 to nucleotide 1752
the complement of the nucleotide sequence of SEQ ID No 2 from nucleotide 1731 to nucleotide 1749
the complement of the nucleotide sequence of SEQ ID No 2 from nucleotide 1732 to nucleotide 1749
the complement of the nucleotide sequence of SEQ ID No 2 from nucleotide 1731 to nucleotide 1751
the complement of the nucleotide sequence of SEQ ID No 2 from nucleotide 1732 to nucleotide 1753
the complement of the nucleotide sequence of SEQ ID No 2 from nucleotide 1731 to nucleotide 1748
the complement of the nucleotide sequence of SEQ ID No 2 from nucleotide 1732 to nucleotide 1748
the complement of the nucleotide sequence of SEQ ID No 2 from nucleotide 1735 to nucleotide 1751
the complement of the nucleotide sequence of SEQ ID No 2 from nucleotide 1731 to nucleotide 1752
the complement of the nucleotide sequence of SEQ ID No 2 from nucleotide 1732 to nucleotide 1754
the complement of the nucleotide sequence of SEQ ID No 2 from nucleotide 1731 to nucleotide 1747
the complement of the nucleotide sequence of SEQ ID No 2 from nucleotide 1731 to nucleotide 1753
the complement of the nucleotide sequence of SEQ ID No 2 from nucleotide 1727 to nucleotide 1746
the complement of the nucleotide sequence of SEQ ID No 2 from nucleotide 1727 to nucleotide 1745
the complement of the nucleotide sequence of SEQ ID No 2 from nucleotide 1727 to nucleotide 1747
the complement of the nucleotide sequence of SEQ ID No 2 from nucleotide 1727 to nucleotide 1744
the complement of the nucleotide sequence of SEQ ID No 2 from nucleotide 1727 to nucleotide 1748
the complement of the nucleotide sequence of SEQ ID No 2 from nucleotide 1727 to nucleotide 1749
the complement of the nucleotide sequence of SEQ ID No 2 from nucleotide 1726 to nucleotide 1745
the complement of the nucleotide sequence of SEQ ID No 2 from nucleotide 1726 to nucleotide 1744
the complement of the nucleotide sequence of SEQ ID No 2 from nucleotide 1726 to nucleotide 1746
the complement of the nucleotide sequence of SEQ ID No 2 from nucleotide 1726 to nucleotide 1747
the complement of the nucleotide sequence of SEQ ID No 2 from nucleotide 1726 to nucleotide 1748
the complement of the nucleotide sequence of SEQ ID No 2 from nucleotide 1724 to nucleotide 1744
the complement of the nucleotide sequence of SEQ ID No 2 from nucleotide 1724 to nucleotide 1745
the complement of the nucleotide sequence of SEQ ID No 2 from nucleotide 1724 to nucleotide 1746
the complement of the nucleotide sequence of SEQ ID No 2 from nucleotide 1461 to nucleotide 1478
the complement of the nucleotide sequence of SEQ ID No 2 from nucleotide 1670 to nucleotide 1686
the complement of the nucleotide sequence of SEQ ID No 2 from nucleotide 1469 to nucleotide 1486
the complement of the nucleotide sequence of SEQ ID No 2 from nucleotide 1508 to nucleotide 1527
the complement of the nucleotide sequence of SEQ ID No 2 from nucleotide 1667 to nucleotide 1686
the complement of the nucleotide sequence of SEQ ID No 2 from nucleotide 1670 to nucleotide 1687
the complement of the nucleotide sequence of SEQ ID No 2 from nucleotide 1673 to nucleotide 1689 the complement of the nucleotide sequence of SEQ ID No 2 from nucleotide 1688 to nucleotide 1704
the complement of the nucleotide sequence of SEQ ID No 2 from nucleotide 1688 to nucleotide 1705
the complement of the nucleotide sequence of SEQ ID No 2 from nucleotide 1692 to nucleotide 1709
the complement of the nucleotide sequence of SEQ ID No 2 from nucleotide 1467 to nucleotide 1486
the complement of the nucleotide sequence of SEQ ID No 2 from nucleotide 1481 to nucleotide 1497
the complement of the nucleotide sequence of SEQ ID No 2 from nucleotide 1481 to nucleotide 1498
the complement of the nucleotide sequence of SEQ ID No 2 from nucleotide 1491 to nucleotide 1507
the complement of the nucleotide sequence of SEQ ID No 2 from nucleotide 1491 to nucleotide 1508
the complement of the nucleotide sequence of SEQ ID No 2 from nucleotide 1672 to nucleotide 1688
the complement of the nucleotide sequence of SEQ ID No 2 from nucleotide 1673 to nucleotide 1690
the complement of the nucleotide sequence of SEQ ID No 2 from nucleotide 1673 to nucleotide 1691
the complement of the nucleotide sequence of SEQ ID No 2 from nucleotide 1688 to nucleotide 1706
the complement of the nucleotide sequence of SEQ ID No 2 from nucleotide 1691 to nucleotide 1707
the complement of the nucleotide sequence of SEQ ID No 2 from nucleotide 1691 to nucleotide 1708
the complement of the nucleotide sequence of SEQ ID No 2 from nucleotide 1469 to nucleotide 1487
the complement of the nucleotide sequence of SEQ ID No 2 from nucleotide 1481 to nucleotide 1499
the complement of the nucleotide sequence of SEQ ID No 2 from nucleotide 1489 to nucleotide 1505
the complement of the nucleotide sequence of SEQ ID No 2 from nucleotide 1489 to nucleotide 1506
the complement of the nucleotide sequence of SEQ ID No 2 from nucleotide 1489 to nucleotide 1507
the complement of the nucleotide sequence of SEQ ID No 2 from nucleotide 1489 to nucleotide 1508
the complement of the nucleotide sequence of SEQ ID No 2 from nucleotide 1666 to nucleotide 1686
the complement of the nucleotide sequence of SEQ ID No 2 from nucleotide 1667 to nucleotide 1687
the complement of the nucleotide sequence of SEQ ID No 2 from nucleotide 1670 to nucleotide 1688
the complement of the nucleotide sequence of SEQ ID No 2 from nucleotide 1672 to nucleotide 1689
the complement of the nucleotide sequence of SEQ ID No 2 from nucleotide 1688 to nucleotide 1707
the complement of the nucleotide sequence of SEQ ID No 2 from nucleotide 1691 to nucleotide 1709
the complement of the nucleotide sequence of SEQ ID No 2 from nucleotide 1692 to nucleotide 1710
the complement of the nucleotide sequence of SEQ ID No 2 from nucleotide 1481 to nucleotide 1500
the complement of the nucleotide sequence of SEQ ID No 2 from nucleotide 1491 to nucleotide 1509
the complement of the nucleotide sequence of SEQ ID No 2 from nucleotide 1670 to nucleotide 1689
the complement of the nucleotide sequence of SEQ ID No 2 from nucleotide 1672 to nucleotide 1690
the complement of the nucleotide sequence of SEQ ID No 2 from nucleotide 1672 to nucleotide 1691
the complement of the nucleotide sequence of SEQ ID No 2 from nucleotide 1687 to nucleotide 1705
the complement of the nucleotide sequence of SEQ ID No 2 from nucleotide 1687 to nucleotide 1706
the complement of the nucleotide sequence of SEQ ID No 2 from nucleotide 1691 to nucleotide 1710
the complement of the nucleotide sequence of SEQ ID No 2 from nucleotide 1472 to nucleotide 1488
the complement of the nucleotide sequence of SEQ ID No 2 from nucleotide 1488 to nucleotide 1507
the complement of the nucleotide sequence of SEQ ID No 2 from nucleotide 1491 to nucleotide 1510
the complement of the nucleotide sequence of SEQ ID No 2 from nucleotide 1495 to nucleotide 1512
the complement of the nucleotide sequence of SEQ ID No 2 from nucleotide 1495 to nucleotide 1513
the complement of the nucleotide sequence of SEQ ID No 2 from nucleotide 1495 to nucleotide 1514
the complement of the nucleotide sequence of SEQ ID No 2 from nucleotide 1673 to nucleotide 1692
the complement of the nucleotide sequence of SEQ ID No 2 from nucleotide 1678 to nucleotide 1694
the complement of the nucleotide sequence of SEQ ID No 2 from nucleotide 1678 to nucleotide 1695
the complement of the nucleotide sequence of SEQ ID No 2 from nucleotide 1678 to nucleotide 1696
the complement of the nucleotide sequence of SEQ ID No 2 from nucleotide 1687 to nucleotide 1703
the complement of the nucleotide sequence of SEQ ID No 2 from nucleotide 1687 to nucleotide 1704
the complement of the nucleotide sequence of SEQ ID No 2 from nucleotide 1692 to nucleotide 1711
the complement of the nucleotide sequence of SEQ ID No 2 from nucleotide 1469 to nucleotide 1488
the complement of the nucleotide sequence of SEQ ID No 2 from nucleotide 1488 to nucleotide 1506
the complement of the nucleotide sequence of SEQ ID No 2 from nucleotide 1491 to nucleotide 1511
the complement of the nucleotide sequence of SEQ ID No 2 from nucleotide 1670 to nucleotide 1690
the complement of the nucleotide sequence of SEQ ID No 2 from nucleotide 1678 to nucleotide 1697
the complement of the nucleotide sequence of SEQ ID No 2 from nucleotide 1688 to nucleotide 1709
the complement of the nucleotide sequence of SEQ ID No 2 from nucleotide 1467 to nucleotide 1487
the complement of the nucleotide sequence of SEQ ID No 2 from nucleotide 1488 to nucleotide 1508
the complement of the nucleotide sequence of SEQ ID No 2 from nucleotide 1495 to nucleotide 1511
the complement of the nucleotide sequence of SEQ ID No 2 from nucleotide 1491 to nucleotide 1512
the complement of the nucleotide sequence of SEQ ID No 2 from nucleotide 1666 to nucleotide 1687
the complement of the nucleotide sequence of SEQ ID No 2 from nucleotide 1667 to nucleotide 1688
the complement of the nucleotide sequence of SEQ ID No 2 from nucleotide 1672 to nucleotide 1692
the complement of the nucleotide sequence of SEQ ID No 2 from nucleotide 1673 to nucleotide 1693
the complement of the nucleotide sequence of SEQ ID No 2 from nucleotide 1687 to nucleotide 1707
the complement of the nucleotide sequence of SEQ ID No 2 from nucleotide 1472 to nucleotide 1490
the complement of the nucleotide sequence of SEQ ID No 2 from nucleotide 1472 to nucleotide 1491
the complement of the nucleotide sequence of SEQ ID No 2 from nucleotide 1481 to nucleotide 1501 the complement of the nucleotide sequence of SEQ ID No 2 from nucleotide 1489 to nucleotide 1509
the complement of the nucleotide sequence of SEQ ID No 2 from nucleotide 1495 to nucleotide 1515
the complement of the nucleotide sequence of SEQ ID No 2 from nucleotide 1670 to nucleotide 1691
the complement of the nucleotide sequence of SEQ ID No 2 from nucleotide 1673 to nucleotide 1694
the complement of the nucleotide sequence of SEQ ID No 2 from nucleotide 1678 to nucleotide 1698
the complement of the nucleotide sequence of SEQ ID No 2 from nucleotide 1469 to nucleotide 1489
the complement of the nucleotide sequence of SEQ ID No 2 from nucleotide 1667 to nucleotide 1689
the complement of the nucleotide sequence of SEQ ID No 2 from nucleotide 1687 to nucleotide 1708
the complement of the nucleotide sequence of SEQ ID No 2 from nucleotide 1688 to nucleotide 1710
the complement of the nucleotide sequence of SEQ ID No 2 from nucleotide 1691 to nucleotide 1711
the complement of the nucleotide sequence of SEQ ID No 2 from nucleotide 1472 to nucleotide 1492
the complement of the nucleotide sequence of SEQ ID No 2 from nucleotide 1489 to nucleotide 1510
the complement of the nucleotide sequence of SEQ ID No 2 from nucleotide 1666 to nucleotide 1688
the complement of the nucleotide sequence of SEQ ID No 2 from nucleotide 1687 to nucleotide 1709
the complement of the nucleotide sequence of SEQ ID No 2 from nucleotide 1692 to nucleotide 1712
the complement of the nucleotide sequence of SEQ ID No 2 from nucleotide 1467 to nucleotide 1488
the complement of the nucleotide sequence of SEQ ID No 2 from nucleotide 1469 to nucleotide 1490
the complement of the nucleotide sequence of SEQ ID No 2 from nucleotide 1488 to nucleotide 1509
the complement of the nucleotide sequence of SEQ ID No 2 from nucleotide 1489 to nucleotide 1511
the complement of the nucleotide sequence of SEQ ID No 2 from nucleotide 1678 to nucleotide 1699
the complement of the nucleotide sequence of SEQ ID No 2 from nucleotide 1472 to nucleotide 1493
the complement of the nucleotide sequence of SEQ ID No 2 from nucleotide 1472 to nucleotide 1494
the complement of the nucleotide sequence of SEQ ID No 2 from nucleotide 1481 to nucleotide 1502
the complement of the nucleotide sequence of SEQ ID No 2 from nucleotide 1670 to nucleotide 1692
the complement of the nucleotide sequence of SEQ ID No 2 from nucleotide 1469 to nucleotide 1491
the complement of the nucleotide sequence of SEQ ID No 2 from nucleotide 1488 to nucleotide 1510
the complement of the nucleotide sequence of SEQ ID No 2 from nucleotide 1691 to nucleotide 1712
the complement of the nucleotide sequence of SEQ ID No 2 from nucleotide 1692 to nucleotide 1713
the complement of the nucleotide sequence of SEQ ID No 2 from nucleotide 1692 to nucleotide 1714
the complement of the nucleotide sequence of SEQ ID No 2 from nucleotide 1467 to nucleotide 1489
the complement of the nucleotide sequence of SEQ ID No 2 from nucleotide 1678 to nucleotide 1700
the complement of the nucleotide sequence of SEQ ID No 2 from nucleotide 1481 to nucleotide 1503
the complement of the nucleotide sequence of SEQ ID No 2 from nucleotide 1691 to nucleotide 1713 c. 3' flanking sequence recognizing primers:
the complement of the nucleotide sequence of SEQ ID No 3 from nucleotide 828 to nucleotide 847
the complement of the nucleotide sequence of SEQ ID No 3 from nucleotide 830 to nucleotide 849
the complement of the nucleotide sequence of SEQ ID No 3 from nucleotide 828 to nucleotide 846
the complement of the nucleotide sequence of SEQ ID No 3 from nucleotide 828 to nucleotide 848
the complement of the nucleotide sequence of SEQ ID No 3 from nucleotide 830 to nucleotide 848
the complement of the nucleotide sequence of SEQ ID No 3 from nucleotide 830 to nucleotide 850
the complement of the nucleotide sequence of SEQ ID No 3 from nucleotide 828 to nucleotide 845
the complement of the nucleotide sequence of SEQ ID No 3 from nucleotide 830 to nucleotide 847
the complement of the nucleotide sequence of SEQ ID No 3 from nucleotide 828 to nucleotide 849
the complement of the nucleotide sequence of SEQ ID No 3 from nucleotide 830 to nucleotide 851
the complement of the nucleotide sequence of SEQ ID No 3 from nucleotide 828 to nucleotide 844
the complement of the nucleotide sequence of SEQ ID No 3 from nucleotide 830 to nucleotide 846
the complement of the nucleotide sequence of SEQ ID No 3 from nucleotide 828 to nucleotide 850
the complement of the nucleotide sequence of SEQ ID No 3 from nucleotide 830 to nucleotide 852
the complement of the nucleotide sequence of SEQ ID No 3 from nucleotide 992 to nucleotide 1009
the complement of the nucleotide sequence of SEQ ID No 3 from nucleotide 731 to nucleotide 752
the complement of the nucleotide sequence of SEQ ID No 3 from nucleotide 776 to nucleotide 795
the complement of the nucleotide sequence of SEQ ID No 3 from nucleotide 731 to nucleotide 753
the complement of the nucleotide sequence of SEQ ID No 3 from nucleotide 776 to nucleotide 794
the complement of the nucleotide sequence of SEQ ID No 3 from nucleotide 776 to nucleotide 796
the complement of the nucleotide sequence of SEQ ID No 3 from nucleotide 776 to nucleotide 793
the complement of the nucleotide sequence of SEQ ID No 3 from nucleotide 776 to nucleotide 797
the complement of the nucleotide sequence of SEQ ID No 3 from nucleotide 776 to nucleotide 792
the complement of the nucleotide sequence of SEQ ID No 3 from nucleotide 776 to nucleotide 798
the complement of the nucleotide sequence of SEQ ID No 3 from nucleotide 733 to nucleotide 752
the complement of the nucleotide sequence of SEQ ID No 3 from nucleotide 733 to nucleotide 753
the complement of the nucleotide sequence of SEQ ID No 3 from nucleotide 733 to nucleotide 754
the complement of the nucleotide sequence of SEQ ID No 3 from nucleotide 733 to nucleotide 755
the complement of the nucleotide sequence of SEQ ID No 3 from nucleotide 838 to nucleotide 854
the complement of the nucleotide sequence of SEQ ID No 3 from nucleotide 246 to nucleotide 263
the complement of the nucleotide sequence of SEQ ID No 3 from nucleotide 838 to nucleotide 855
the complement of the nucleotide sequence of SEQ ID No 3 from nucleotide 245 to nucleotide 264 d. foreign DNA sequence recognizing primers for use with 3' flanking sequence recognizing primers:
  the nucleotide sequence of SEQ ID No 3 from nucleotide 173 to nucleotide 192
  the nucleotide sequence of SEQ ID No 3 from nucleotide 22 to nucleotide 41
  the nucleotide sequence of SEQ ID No 3 from nucleotide 172 to nucleotide 192
  the nucleotide sequence of SEQ ID No 3 from nucleotide 174 to nucleotide 192
  the nucleotide sequence of SEQ ID No 3 from nucleotide 191 to nucleotide 210
  the nucleotide sequence of SEQ ID No 3 from nucleotide 171 to nucleotide 192
  the nucleotide sequence of SEQ ID No 3 from nucleotide 175 to nucleotide 192
  the nucleotide sequence of SEQ ID No 3 from nucleotide 190 to nucleotide 210
  the nucleotide sequence of SEQ ID No 3 from nucleotide 192 to nucleotide 210
  the nucleotide sequence of SEQ ID No 3 from nucleotide 176 to nucleotide 192
  the nucleotide sequence of SEQ ID No 3 from nucleotide 189 to nucleotide 210
  the nucleotide sequence of SEQ ID No 3 from nucleotide 193 to nucleotide 210
  the nucleotide sequence of SEQ ID No 3 from nucleotide 188 to nucleotide 210
  the nucleotide sequence of SEQ ID No 3 from nucleotide 194 to nucleotide 210
  the nucleotide sequence of SEQ ID No 3 from nucleotide 199 to nucleotide 218
  the nucleotide sequence of SEQ ID No 3 from nucleotide 200 to nucleotide 218
  the nucleotide sequence of SEQ ID No 3 from nucleotide 197 to nucleotide 218
  the nucleotide sequence of SEQ ID No 3 from nucleotide 201 to nucleotide 218
  the nucleotide sequence of SEQ ID No 3 from nucleotide 201 to nucleotide 220
  the nucleotide sequence of SEQ ID No 3 from nucleotide 200 to nucleotide 220
  the nucleotide sequence of SEQ ID No 3 from nucleotide 199 to nucleotide 220
  the nucleotide sequence of SEQ ID No 3 from nucleotide 200 to nucleotide 221
  the nucleotide sequence of SEQ ID No 3 from nucleotide 199 to nucleotide 221
  the nucleotide sequence of SEQ ID No 3 from nucleotide 150 to nucleotide 172

PCR primers suitable for the identification of EE-GM1 have been described in WO2006/108674, particularly on page 8, line 4 to page 26, line 7 (herein incorporated by reference).

PCR primers suitable for the identification of EE-GM2 have been described in WO2006/108675, particularly on pages 8, line 4 to page 33, line 4 (herein incorporated by reference).

As used herein, "the nucleotide sequence of SEQ ID No. Z from position X to position Y" indicates the nucleotide sequence including both nucleotide endpoints.

Preferably, the amplified fragment has a length of between 50 and 500 nucleotides, such as a length between 100 and 350 nucleotides. The specific primers may have a sequence which is between 80 and 100% identical to a sequence within the 5' or 3' flanking region of the elite event and the foreign DNA of the elite event, respectively, provided the mismatches still allow specific identification of the elite event with these primers under optimized PCR conditions. The range of allowable mismatches however, can easily be determined experimentally and are known to a person skilled in the art.

Detection of integration fragments can occur in various ways, e.g., via size estimation after gel analysis. The integration fragments may also be directly sequenced. Other sequence specific methods for detection of amplified DNA fragments are also known in the art.

As the sequence of the primers and their relative location in the genome are unique for the elite event, amplification of the integration fragment will occur only in biological samples comprising (the nucleic acid of) the elite event. Preferably when performing a PCR to identify the presence of elite events EE-GM3 and EE-GM1 or elite events EE-GM3 and EE-GM2 in unknown samples, a control is included of a set of primers with which a fragment within a "housekeeping gene" of the plant species of the event can be amplified. Housekeeping genes are genes that are expressed in most cell types and which are concerned with basic metabolic activities common to all cells. Preferably, the fragment amplified from the housekeeping gene is a fragment which is larger than the amplified integration fragment. Depending on the samples to be analyzed, other controls can be included.

Standard PCR protocols are described in the art, such as in 'PCR Applications Manual (Roche Molecular Biochemicals, 2nd Edition, 1999) and other references. The optimal conditions for the PCR, including the sequence of the specific primers, are specified in a "PCR (or Polymerase Chain Reaction) Identification Protocol" for each elite event. It is however understood that a number of parameters in the PCR Identification Protocol may need to be adjusted to specific laboratory conditions, and may be modified slightly to obtain similar results. For instance, use of a different method for preparation of DNA may require adjustment of, for instance, the amount of primers, polymerase and annealing conditions used. Similarly, the selection of other primers may dictate other optimal conditions for the PCR Identification Protocol. These adjustments will however be apparent to a person skilled in the art, and are furthermore detailed in current PCR application manuals such as the one cited above.

Alternatively, specific primers can be used to amplify integration fragments that can be used as "specific probes" for identifying EE-GM3 and EE-GM1 or EE-GM3 and EE-GM2 in biological samples. Contacting nucleic acid of a biological sample, with the probes, under conditions which allow hybridization of the probes with their corresponding fragments in the sample nucleic acid, results in the formation of nucleic acid/probe hybrids. The formation of these hybrids can be detected (e.g. via labeling of the nucleic acid or probe), whereby the formation of these hybrids indicates the presence of EE-GM3 and EE-GM1 or EE-GM3 and EE-GM2. Such identification methods based on hybridization with a specific probe (either on a solid phase carrier or in solution) have been described in the art. The specific probe is preferably a sequence which, under optimized conditions, hybridizes specifically to a region within the 5' or 3' flanking region of the elite event and preferably also comprising part of the foreign DNA contiguous therewith (hereinafter referred to as "specific region"). Preferably, the specific probe comprises a sequence of between 50 and 500 bp, preferably of 100 to 350 bp which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 15 to about 100 contiguous nucleotides identical (or complementary) to a specific region of the elite event.

Furthermore, detection methods specific for elite events EE-GM3 and EE-GM1 or for elite events EE-GM3 and EE-GM2 which differ from PCR based amplification methods can also be developed using the elite event specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", 6,001,567 Detection of Nucleic Acid sequences by Invader Directed Cleavage, incorporated herein by reference). For EE-GM3 detection by this method, the target sequence may hybridized with a labeled first nucleic acid oligonucleotide comprising the nucleotide sequence of SEQ ID No 2 from nucleotide 1452 to nucleotide 1469 or its complement or said labeled nucleic acid probe comprising the nucleotide sequence of SEQ ID No 3 from nucleotide 223 to nucleotide 240 or its complement and is further hybridized with a second nucleic acid oligonucleotide comprising the nucleotide sequence of SEQ ID No 2 from nucleotide 1434 to nucleotide 1451 or its complement or said labeled nucleic acid probe comprising the nucleotide sequence of SEQ ID No 3 from nucleotide 241 to nucleotide 258 or its complement, wherein the first and second oligonucleotide overlap by at least one nucleotide. The duplex or triplex structure which is produced by this hybridization allows selective probe cleavage with an enzyme (Cleavase®) leaving the target sequence intact. The cleaved labeled probe is subsequently detected, potentially via an intermediate step resulting in further signal amplification. For EE-GM1 detection by this method, the target sequence may hybridized with a labeled first nucleic acid oligonucleotide comprising the nucleotide sequence of SEQ ID No 12 from nucleotide 210 to nucleotide 227 or its complement or said labeled nucleic acid probe comprising the nucleotide sequence of SEQ ID No 13 from nucleotide 561 to nucleotide 568 or its complement and is further hybridized with a second nucleic acid oligonucleotide comprising the nucleotide sequence of SEQ ID No 12 from nucleotide 192 to nucleotide 209 or its complement or said labeled nucleic acid probe comprising the nucleotide sequence of SEQ ID No 13 from nucleotide 569 to nucleotide 586 or its complement, wherein the first and second oligonucleotide overlap by at least one nucleotide. The duplex or triplex structure which is produced by this hybridization allows selective probe cleavage with an enzyme (Cleavase®) leaving the target sequence intact. The cleaved labeled probe is subsequently detected, potentially via an intermediate step resulting in further signal amplification. For EE-GM2 detection by this method, the target sequence may hybridized with a labeled first nucleic acid oligonucleotide comprising the nucleotide sequence of SEQ ID No 14 from nucleotide 312 to nucleotide 329 or its complement or said labeled nucleic acid probe comprising the nucleotide sequence of SEQ ID No 15 from nucleotide 490 to nucleotide 507 or its complement and is further hybridized with a second nucleic acid oligonucleotide comprising the nucleotide sequence of SEQ ID No 14 from nucleotide 294 to nucleotide 311 or its complement or said labeled nucleic acid probe comprising the nucleotide sequence of SEQ ID No 15 from nucleotide 508 to nucleotide 525 or its complement, wherein the first and second oligonucleotide overlap by at least one nucleotide. The duplex or triplex structure which is produced by this hybridization allows selective probe cleavage with an enzyme (Cleavase®) leaving the target sequence intact. The cleaved labeled probe is subsequently detected, potentially via an intermediate step resulting in further signal amplification.

A "kit" as used herein refers to a set of reagents for the purpose of performing the method of the invention, more particularly, the identification of the elite event EE-GM3 in biological samples or the determination of the zygosity status of EE-GM3 containing plant material. More particularly, a preferred embodiment of the kit of the invention comprises at least one or two specific primers, as described above for identification of the elite event, or three specific primers for the determination of the zygosity status. Optionally, the kit can further comprise any other reagent described herein in the PCR Identification Protocol. Alternatively, according to another embodiment of this invention, the kit can comprise a specific probe, as described above, which specifically hybridizes with nucleic acid of biological samples to identify the presence of EE-GM3 therein. Optionally, the kit can further comprise any other reagent (such as but not limited to hybridizing buffer, label) for identification of EE-GM3 in biological samples, using the specific probe.

The kit of the invention can be used, and its components can be specifically adjusted, for purposes of quality control (e.g., purity of seed lots), detection of the presence or absence of the elite event in plant material or material comprising or derived from plant material, such as but not limited to food or feed products.

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983, Proc. Nat. Acad. Sci. USA 80:726) using a window-size of 20 nucleotides, a word length of 4 nucleotides, and a gap penalty of 4. Computer-assisted analysis and interpretation of sequence data, including sequence alignment as described above, can, e.g., be conveniently performed using the sequence analysis software package of the Genetics Computer Group (GCG, University of Wisconsin Biotechnology Center). Sequences are indicated as "essentially similar" when such sequences have a sequence identity of at least about 75%, particularly at least about 80%, more particularly at least about 85%, quite particularly at least about 90%, especially at least about 95%, more especially at least about 98%, or at least about 99%. It is clear that when RNA sequences are said to be essentially similar or have a certain degree of sequence identity with DNA sequences, thymidine (T) in the DNA sequence is considered equal to uracil (U) in the RNA sequence. Also, it is clear that small differences or mutations may appear in DNA sequences over time and that some mismatches can be allowed for the event-specific primers or probes of the invention, so any DNA sequence indicated herein in any embodiment of this invention for any 3' or 5' flanking DNA or for any insert or foreign DNA or any primer or probe of this invention, also includes sequences essentially similar to the sequences provided herein, such as sequences hybridizing to or with at least 90%, 95%, 96%, 97%, 98%, or at least 99% sequence identity to the sequence given for any 3' or 5' flanking DNA, for any primer or probe or for any insert or foreign DNA of this invention.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in the elite event under the conditions set forth in the method (such as the conditions of the PCR Identification Protocol), whereby the specificity is determined by the presence of positive and negative controls.

The term "hybridizing" as used herein when referring to specific probes, refers to the fact that the probe binds to a specific region in the nucleic acid sequence of the elite event under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbor Laboratory Press, NY) which for instance can comprise the following steps: 1) immobilizing plant genomic DNA fragments on a filter, 2) prehybridizing the filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS, 3) adding the hybridization probe which has been labeled, 4) incubating for 16 to 24 hours, 5) washing the filter for 20 min. at room temperature in 1×SSC, 0.1% SDS, 6) washing the filter three times for 20 min. each at 68° C. in 0.2×SSC, 0.1% SDS, and 7) exposing the filter for 24 to 48 hours to X-ray film at −70° C. with an intensifying screen.

As used in herein, a biological sample is a sample of a plant, plant material or products comprising plant material. The term "plant" is intended to encompass soybean (*Glycine max*) plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material which is obtained or derived from a plant. Products comprising plant material relate to food, feed or other products which are produced using plant material or can be contaminated by plant material. It is understood that, in the context of the present invention, such biological samples are tested for the presence of nucleic acids specific for EE-GM3, EE-GM1 and EE-GM2 implying the presence of nucleic acids in the samples. Thus the methods referred to herein for identifying elite event EE-GM3 and EE-GM2 or EE-GM3 and EE-GM1 in biological samples, relate to the identification in biological samples of nucleic acids which comprise the elite event.

As used herein "comprising" is to be interpreted as specifying the presence of the stated features, integers, steps, reagents or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence which is functionally or structurally defined, may comprise additional DNA sequences, such as promoter and transcript termination sequences.

The present invention also relates to the development of a stack of elite event EE-GM3 and elite event EE-GM1 or a stack of elite event EE-GM3 and elite event EE-GM2 in soybean, to the plants comprising a stack of these events, the progeny obtained from these plants and to the plant cells, or plant material derived from plants comprising these stacks. Plants comprising elite event EE-GM3 and EE-GM1 or EE-GM3 and EE-GM2 can be obtained as described in example 1. Stacks are obtained by crossing plants comprising single events using conventional breeding methods and identification of progeny thereof comprising two different events.

Soybean plants or plant material comprising EE-GM3 and EE-GM1 can be identified according to the PCR Identification Protocol described for EE-GM3 and EE-GM1 in Example 2. Briefly, soybean genomic DNA present in the biological sample is amplified by PCR using a primer which specifically recognizes a sequence within the 5' or 3' flanking sequence of EE-GM3 such as the primer with the sequence of SEQ ID NO: 5, and a primer which recognizes a sequence in the foreign DNA, such as the primer with the sequence of SEQ ID NO: 4 and further using a primer which specifically recognizes a sequence within the 5' or 3' flanking sequence of EE-GM1 such as the primer with the sequence of SEQ ID NO: 16, and a primer which recognizes a sequence in the foreign DNA, such as the primer with the sequence of SEQ ID NO: 17.

Soybean plants or plant material comprising EE-GM3 and EE-GM2 can be identified according to the PCR Identification Protocol described for EE-GM3 and EE-GM2 in Example 2. Briefly, soybean genomic DNA present in the biological sample is amplified by PCR using a primer which specifically recognizes a sequence within the 5' or 3' flanking sequence of EE-GM3 such as the primer with the sequence of SEQ ID NO: 5, and a primer which recognizes a sequence in the foreign DNA, such as the primer with the sequence of SEQ ID NO: 4 and further using a primer which specifically recognizes a sequence within the 5' or 3' flanking sequence of EE-GM2 such as the primer with the sequence of SEQ ID NO: 18, and a primer which recognizes a sequence in the foreign DNA, such as the primer with the sequence of SEQ ID NO: 19.

DNA primers which amplify part of an endogenous soybean sequence are used as positive control for the PCR amplification. If upon PCR amplification, the material yields the fragments of the expected sizes, the material contains plant material from a soybean plant harboring elite event EE-GM3 and EE-GM1 or from a soybean plant harboring elite event EE-GM3 and EE-GM2.

Plants harboring EE-GM3 and EE-GM1 or EE-GM3 and EE-GM2 are characterized by their glyphosate tolerance, as well as by their tolerance to HPPD inhibitors such as isoxaflutol and further by their tolerance to glufosinate. Plants harboring the event stacks are also characterized by having agronomical characteristics that are comparable to commercially available varieties of soybean, in the absence of herbicide application. It has been observed that the presence of foreign DNA in the insertion regions of the soybean plant genome described herein, confers particularly interesting phenotypic and molecular characteristics to the plants comprising this event.

One embodiment of this invention provides a combination or elite events EE-GM3 and EE-GM1 and/or EE-GM2 in soybean plants, obtainable by insertion of transgenes at specific locations in the soybean genome, which elite events confers tolerance to glyphosate, glufosinate and an HPPD inhibitor herbicide such as isoxaflutole on such soybean plants, and wherein such elite events do not cause any effect on the agronomic performance of such soybeans negatively affecting the yield of such soybean plants, compared to isogenic lines (as used herein, "isogenic lines" or "near-isogenic lines" are soybean lines of the same genetic background but lacking the transgenes, such as plants of the same genetic background as the plant used for transformation, or segregating sister lines having lost the transgenes). Particularly, the current invention provides a combination of elite events EE-GM3 and EE-GM1 and/or EE-GM2 in soybean plants, wherein the insertion or presence of said elite event in the genome of such soybean plants does not cause an increased susceptibility to disease, does not cause a yield drag, or does not cause increased lodging, in such soybean plants, as compared to isogenic lines. Hence, the current invention provides a combination of elite events in soybean plants, designated as EE-GM3 and EE-GM1 and/or EE-GM2, which results in soybean plants that can tolerate the application of glyphosate, glufosinate and an HPPD inhibitor herbicide (either simultaneously or separately) without negatively affecting the yield of said soybean plants compared to isogenic lines, which soybean plants have no statistically significant difference in their disease susceptibility, or lodging, compared to isogenic soybean plants. These characteristics make the current combination of elite events very interesting to control glyphosate-resistant weeds in soybean fields, and can also be used in approaches to prevent or delay further glyphosate resistance development in soybean fields (e.g., by application of glyphosate and isoxaflutole and/or glufosinate, or by application of isoxaflutole and glyphosate and/or glufosinate, or by application of glufosinate and glyphosate and/or isoxafulote, securing at least 2 or even 3 different modes of actions of herbicides applied on a soybean field).

Provided herein is also a soybean plant or part thereof comprising event EE-GM3 and elite event EE-GM1 or EE-GM2, wherein representative soybean seed comprising event EE-GM3 has been deposited under NCIMB accession number 41659, representative soybean seed comprising elite event EE-GM1 has been deposited at the NCIMB under accession number NCIMB 41658, representative seed comprising elite event EE-GM2 has been deposited at the NCIMB under accession number NCIMB 41660, representative soybean seed comprising event EE-GM3 and EE-GM1 has been deposited at the ATCC under accession number PTA-11041, and representative soybean seed comprising event EE-GM3 and EE-GM2 has been deposited at the ATCC under accession number PTA-11042.

Soybean plants or parts thereof comprising EE-GM3 and EE-GM1 or EE-GM3 and EE-GM2 may be obtained by combining the respective elite events as can be found in the respective deposited seeds through any means available in the art, including by crossing plants from the deposited seeds, collecting the progeny thereof, and identifying those progeny plants comprising the appropriate combination of elite events. Further provided herein are seeds of such plants, comprising such events, as well as a soybean product produced from such seeds, wherein said soybean product comprises event EE-GM3 and EE-GM1 or EE-GM2. Such soybean product can be or can comprise meal, ground seeds, flour, flakes, etc. Particularly, such soybean product comprises a nucleic acid that produces amplicons diagnostic for event EE-GM3 and elite event EE-GM1 or EE-GM2, such amplicons comprising SEQ ID No. 2 or 3, SEQ ID No. 14 or 15 and/or SEQ ID No. 12 or 13. Also provided herein is a method for producing a soybean product, comprising obtaining soybean seed comprising event EE-GM3 and elite event EE-GM1 or EE-GM2, and producing such soybean product therefrom.

Also provided herein is a soybean plant, which is progeny of any of the above soybean plants, and which comprises event EE-GM3 and EE-GM1 or EE-GM2.

Further provided herein is a method for producing a soybean plant tolerant to glyphosate and/or glufosinate and/or isoxaflutole herbicides, comprising introducing into the genome of such plant event EE-GM3 and event EE-GM1 or EE-GM2, particularly by crossing a first soybean plant containing event EE-GM3 with a soybean plant comprising EE-GM1 and/or EE-GM2, and selecting a progeny plant tolerant to glyphosate and/or glufosinate and/or isoxaflutole.

Also provided herein is a glyphosate and glufosinate and/or isoxaflutole tolerant plant, particularly without yield drag, and with acceptable agronomical characteristics, comprising a 2mEPSPS, HPPD and PAT protein, and capable of producing an amplicon diagnostic for events EE-GM3 and EE-GM1 or EE-GM3 and EE-GM2.

Further provided herein is a method for controlling weeds in a field of soybean plants comprising events EE-GM3 and EE-GM1 or EE-GM3 and EE-GM2, or a field to be planted with such soybean plants, comprising treating the field with an effective amount of an isoxaflutole-based, glyphosate-based and/or glufosinate-based herbicide, wherein such plants are tolerant to such herbicide(s).

Further provided herein is a soybean plant, cell, tissue or seed, comprising EE-GM3 and EE-GM1, characterized by comprising in the genome of its cells a nucleic acid sequence with at least 80%, 90%, 95% or 100% sequence identity to SEQ ID No. 2 from nucleotide 1431 to 1472 and a nucleic acid sequence with at least 80%, 90%, 95% or 100% sequence identity to SEQ ID No. 3 from nucleotide 220 to 261, or the complement of said sequences, and also a nucleic acid sequence with at least 80%, 90%, 95% or 100% sequence identity to SEQ ID No. 12 from nucleotide 199 to 220 and a nucleic acid sequence with at least 80%, 90%, 95% or 100% sequence identity to SEQ ID No. 13 from nucleotide 558 to 579, or the complement of said sequences.

Also provided herein is a soybean plant, cell, tissue or seed, comprising EE-GM3 and EE-GM2, characterized by comprising in the genome of its cells a nucleic acid sequence with at least 80%, 90%, 95% or 100% sequence identity to SEQ ID No. 2 from nucleotide 1431 to 1472 and a nucleic acid sequence with at least 80%, 90%, 95% or 100% sequence identity to SEQ ID No. 3 from nucleotide 220 to 261, or the complement of said sequences, and also a nucleic acid sequence with at least 80%, 90%, 95% or 100% sequence identity to SEQ ID No. 14 from nucleotide 301 to 322 and a nucleic acid sequence with at least 80%, 90%, 95% or 100% sequence identity to SEQ ID No. 15 from nucleotide 497 to 518, or the complement of said sequences.

The term "isoxaflutole", as used herein, refers to the herbicide isoxaflutole [i.e.(5-cyclopropyl-4-isoxazolyl)[2-(methylsulfonyl)-4-(trifluoromethyl)phenyl]methanone], the active metabolite thereof, diketonitrile, and any mixtures or solutions comprising said compounds. HPPD inhibiting herbicides useful for application on the plants comprising the events of this invention are the diketonitriles, e.g. 2-cyano-3-cyclopropyl-1-(2-methylsulphonyl-4-trifluoromethylphenyl)-propane-1,3-dione and 2-cyano-1-[4-(methylsulphonyl)-2-trifluoromethylphenyl]-3-(1-methylcyclopropyl)propane-1,3-fione; other isoxazoles; and the pyrazolinates, e.g. topramezone [i.e. [3-(4,5-dihydro-3-isoxazolyl)-2-methyl-4-(methylsulfonyl)phenyl](5-hydroxy-1-methyl-1H-pyrazol-4-yl)methanone], and pyrasulfotole [(5-hydroxy-1, 3-dimethylpyrazol-4-yl(2-mesyl-4-trifluaromethylphenyl) methanone]; or pyrazofen [2-[4-(2,4-dichlorobenzoyl)-1,3-dimethylpyrazol-5-yloxy]acetophenone].

In one embodiment of this invention, a field to be planted with soybean plants containing the EE-GM3 event, can be treated with an HPPD inhibitor herbicide, such as isoxaflutole ('IFT'), before the soybean plants are planted or the seeds are sown, which cleans the field of weeds that are killed by the HPPD inhibitor, allowing for no-till practices, followed by planting or sowing of the soybeans in that same pre-treated field later on (burndown application using an HPPD inhibitor herbicide). The residual activity of IFT will also protect the emerging and growing soybean plants from competition by weeds in the early growth stages. Once the soybean plants have a certain size, and weeds tend to re-appear, glyphosate, or an HPPD inhibitor-glyphosate mixture, can be applied as post-emergent herbicide over the top of the plants.

In another embodiment of this invention, a field in which seeds containing the EE-GM3 event were sown, can be treated with an HPPD inhibitor herbicide, such as IFT, before the soybean plants emerge but after the seeds are sown (the field can be made weed-free before sowing using other means, typically conventional tillage practices such as ploughing, chissel ploughing, or seed bed preparation), where residual activity will keep the field free of weeds killed by the herbicide so that the emerging and growing soybean plants have no competition by weeds (pre-emergence application of an HPPD inhibitor herbicide). Once the soybean plants have a certain size, and weeds tend to re-appear, glyphosate—or an HPPD inhibitor-glyphosate mixture—can be applied as post-emergent herbicide over the top of the plants.

In another embodiment of this invention, plants containing the EE-GM3 event, can be treated with an HPPD inhibitor herbicide, such as IFT, over the top of the soybean plants (that have emerged from the seeds that were sown), which cleans the field of weeds killed by the HPPD inhibitor, which application can be together with (e.g., in a spray tank mix), followed by or preceded by a treatment with glyphosate as post-emergent herbicide over the top of the plants (post-emergence application of an HPPD inhibitor herbicide (with or without glyphosate)).

Also, in accordance with the current invention, soybean plants harboring EE-GM3 and EE-GM1 or EE-GM2 may be treated with the following insectides, herbicides or fungicides or soybean seeds harboring EE-GM3 and EE-GM1 or EE-GM2 may be coated with a seed coating comprising the following insectides, herbicides or fungicides:

Soybean Herbicides:
Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Isoxaflutole, Glufosinate.

Soybean Insecticides:
Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin.

Soybean Fungicides:
Azoxystrobin, Cyproconazole, Epoxiconazole, Flutriafol, Pyraclostrobin, Tebuconazole, Trifloxystrobin, Prothioconazole, Tetraconazole.

The following examples describe the identification of elite events EE-GM3, EE-GM1 and EE-GM2 and of plants containing a stack of event EE-GM3 with EE-GM1 or EE-GM3 with EE-GM2 and the development of tools for the specific identification of elite event EE-GM3, EE-GM1 or EE-GM2 and stacks thereof in biological samples.

Unless stated otherwise in the Examples, all recombinant techniques are carried out according to standard protocols as described in "Sambrook J and Russell D W (eds.) (2001) Molecular Cloning: A Laboratory Manual, 3rd Edition, Cold Spring Harbor Laboratory Press, New York" and in "Ausubel FA, Brent R, Kingston RE, Moore DD, Seidman JG, Smith JA and Struhl K (eds.) (2006) Current Protocols in Molecular Biology. John Wiley & Sons, New York".

Standard materials and references are described in "Croy RDD (ed.) (1993) Plant Molecular Biology LabFax, BIOS Scientific Publishers Ltd., Oxford and Blackwell Scientific Publications, Oxford" and in "Brown TA, (1998) Molecular Biology LabFax, 2nd Edition, Academic Press, San Diego". Standard materials and methods for polymerase chain reactions (PCR) can be found in "McPherson MJ and Møller SG (2000) PCR (The Basics), BIOS Scientific Publishers Ltd., Oxford" and in "PCR Applications Manual," 3rd Edition (2006), Roche Diagnostics GmbH, Mannheim or the roche-applied-science website.

It should be understood that a number of parameters in any lab protocol such as the PCR protocols in the below Examples may need to be adjusted to specific laboratory conditions, and may be modified slightly to obtain similar results. For instance, use of a different method for preparation of DNA or the selection of other primers in a PCR method may dictate other optimal conditions for the PCR protocol. These adjustments will however be apparent to a person skilled in the art, and are furthermore detailed in current PCR application manuals.

In the description and examples, reference is made to the following sequences:
SEQ ID No. 1: SalI fragment nucleotide sequence of vector pSF10.
SEQ ID No. 2: nucleotide sequence comprising the 5' region flanking the foreign DNA comprising the herbicide tolerance genes in EE-GM3.
SEQ ID No. 3: nucleotide sequence comprising the 3' region flanking the foreign DNA comprising the herbicide tolerance genes in EE-GM3.
SEQ ID No. 4: primer SOY028
SEQ ID No. 5: primer SOY029
SEQ ID No. 6: primer SMP 187
SEQ ID No. 7: primer STV019
SEQ ID No. 8: nucleotide sequence of the amplicon
SEQ ID No. 9: primer 1 for amplification of control fragment (SOY01)
SEQ ID No. 10: primer 2 for amplification of control fragment (SOY02)
SEQ ID No. 11: nucleotide sequence of pB2/P35SAcK
SEQ ID No. 12: nucleotide sequence comprising the 5' region flanking the foreign DNA in EE-GM1
SEQ ID No. 13: nucleotide sequence comprising the 3' region flanking the foreign DNA in EE-GM1
SEQ ID No. 14: nucleotide sequence comprising the 5' region flanking the foreign DNA in EE-GM2
SEQ ID No. 15: nucleotide sequence comprising the 3' region flanking the foreign DNA in EE-GM2
SEQ ID No. 16: primer SOY06
SEQ ID No. 17: primer SOY07
SEQ ID No. 18: primer SOY09
SEQ ID No. 19: primer SOY010
SEQ ID No. 20: nucleotide sequence of a foreign DNA and plant flanking sequences in EE-GM3
SEQ ID No. 21: primer SHA130
SEQ ID No. 22: primer SHA178

EXAMPLES

1. Transformation of *Glycine max* with Herbicide Tolerance Genes.

1.1. Description of the Foreign DNA Comprising the 2mEPSPS and HPPD-Pf-W336 Chimeric Genes Plasmid pSF10 is a pUC19 derived cloning vector which contains a chimeric 2mepsps gene and a chimeric hppd-Pf-W336 gene located on a SalI fragment of about 7.3 kb. A full description of the DNA comprised between the two SalI restriction sites is given in Table 1 below. The nucleotide sequence is represented in SEQ ID No. 1.

TABLE 1

Nucleotide positions of the DNA comprised between the SalI restriction sites of pSF10 (SEQ ID No 1)

| Nucleotide positions | Orientation | Description and references |
|---|---|---|
| 188-479 | complement | 3'nos: sequence including the 3' untranslated region of the nopaline synthase gene from the T-DNA of pTiT37 of *Agrobacterium tumefaciens* (Depicker et al., 1982, Journal of Molecular and Applied Genetics, 1, 561-573) |
| 480-1556 | complement | hppdPfW336: the coding sequence of the 4-hydroxyphenylpyruvate dioxygenase of *Pseudomonas fluorescens* strain A32 modified by the replacement of the amino acid Glycine 336 with a Tryptophane, as described by Boudec et al. (2001) U.S. Pat. No. 6,245,968B1 |
| 1557-1928 | complement | TPotp Y: coding sequence of an optimized transit peptide derivative (position 55 changed into Tyrosine), containing sequence of the RuBisCO small subunit genes of *Zea mays* (corn) and *Helianthus annuus* (sunflower), as described by Lebrun et al. (1996) U.S. Pat. No. 5,510,471 |
| 1929-2069 | complement | 5'tev: sequence including the leader sequence of the tobacco etch virus as described by Carrington and Freed (1990) Journal of Virology, 64, 1590-1597 |
| 2070-3359 | complement | Ph4a748 ABBC: sequence including the promoter region of the histone H4 gene of *Arabidopsis thaliana*, containing an internal duplication (Chabouté et al., 1987) Plant Molecular Biology, 8, 179-191. |
| 3360-4374 | | Ph4a748: sequence including the promoter region of the histone H4 gene of *Arabidopsis thaliana* (Chabouté et al., 1987) Plant Molecular Biology, 8, 179-191. |
| 4375-4855 | | intron1 h3At: first intron of gene II of the histone H3.III variant of *Arabidopsis thaliana* (Chaubet et al., 1992) Journal of Molecular Biology, 225, 569-574. |
| 4856-5227 | | TPotp C: coding sequence of the optimized transit peptide, containing sequence of the RuBisCO small subunit genes of *Zea mays* (corn) and *Helianthus annuus* (sunflower), as described by Lebrun et al. (1996) U.S. Pat. No. 5,510,471 |
| 5228-6565 | | 2mepsps: the coding sequence of the double-mutant 5-enol-pyruvylshikimate-3-phosphate synthase gene of *Zea mays* (corn) (Lebrun et al., 1997) WO9704103-A 1 |
| 6566-7252 | | 3'histonAt: sequence including the 3' untranslated region of the histone H4 gene of *Arabidopsis thaliana* (Chabouté et al., 1987) Plant Molecular Biology, 8, 179-191. |

1.2. Event EE-GM3

The HPLC purified SalI-linearized pSF10 fragment of about 7.3 kb (containing the 2mEPSPS glyphosate-tolerance gene and the HPPD inhibitor tolerance gene HPPD-Pf-W336) was used to obtain transformed soybean plants by means of direct gene transfer into cells of soybean type Jack (Nickell, C. D., G. R. Noel, D. J. Thomas, and R. Waller. Registration of 'Jack' soybean. *Crop Sci* 1365. 30.1990), followed by regeneration of transformed plant cells into transgenic fertile soybean plants.

1.2.1 Identification of Elite Event EE-GM3

Elite event EE-GM3 was selected based on an extensive selection procedure based on good expression and stability of the herbicide tolerance genes, and its compatibility with optimal agronomic characteristics such as plant height, height to node, stand, vigor, seed yield, were evaluated. Soybean plants containing this event were selected from a wide range of different transformation events obtained using the same chimeric genes. Parameters used in the selection of this event were: a) acceptable tolerance to isoxaflutole herbicide application in field trials, b) acceptable tolerance to glyphosate herbicide application in field trials, c) acceptable tolerance to combined application of isoxaflutole and glyphosate herbicides in field trials, d) an insertion of the herbicide tolerance transgenes at a single locus in the soybean plant genome, with absence of vector backbone, e) overall agronomy similar to the parent plants used for transformation (maturity, lodging, disease susceptibility, etc.), and f) no significant yield drag caused by the insertion of the transforming DNA (as compared to an isogenic line without the event, such as the plant line used for transformation, grown under the same conditions).

At the T3 generation, a homozygous line of the soybean transformation event EE-GM3 was selected for seed production. Multi-location replicated agronomic field studies were conducted in the regions of adaptation of the parent variety, Jack. Field evaluations included herbicide tolerance and agronomic performance. The agronomic performance of plants containing EE-GM3 was found comparable to Jack (when no herbicides were applied).

The field evaluations also showed that plants carrying the EE-GM3 event have:
- similar plant morphology and seed characteristics compared to Jack,
- no change in response to soybean diseases compared to Jack, and
- no changes in seed germination or dormancy compared to Jack.

Seed (T1 or S1 generation) harvested from the initial transformant (T0) plant (the plant transformed with the construct so as to produce event EE-GM3) in the greenhouse were planted in the field. Three blocks were planted and sprayed with 0, 2, or 4 kg/ha glyphosate. Seed was harvested from plants demonstrating the desired level of tolerance to the herbicide, glyphosate.

Seeds (T2 generation) harvested from self-pollinated T1 plants grown in the field were sown "plant to row". Chi square analysis of segregation data for rows (fully or partially tolerant) and of individual plants within rows (tolerant or sensitive) demonstrates the expected Mendelian inheritance of a single insertion for EE-GM3.

Selection and seed increase continued until a line was determined to be homozygous for transformation event EE-GM3 and selected for core seed production in the fourth generation. Then, T5 generation seed served as a candidate for the development of different varieties. Plants in the sixth generation (T6 generation) were crossed with conventional soybean breeding lines in an introgression program designed to move the event into a broader base of commercial soybean germplasm. F1 hybrid plants (EE-GM3 lines×conventional lines) were grown to maturity and the F2 seed was planted. Leaf samples of 901 F2 plants were analyzed by PCR primers designed to identify the zygosity of the EE-GM3 insert. The expected ratio of 1:2:1 for a single insertion segregation by the rules of Mendel was observed.

The selected event EE-GM3 was introduced in different commercial genetic backgrounds, and results of field trials on different locations were compared. Plants were challenged with glyphosate herbicide and/or isoxaflutole herbicide using different treatments. The plants exhibited good herbicide tolerance. Hundreds of different soybean cultivars containing event EE-GM3 were used in an inheritance study, and herbicides were applied. Selected lines from this trial were later increased in the field and also treated with herbicide. From that trial, 50 selected lines were increased, and these were also herbicide treated. The phytotoxicity scores for the latter lines sprayed with isoxaflutole and glyphosate showed some variability in response, but the range of responses among the lines reflected similar variability as was observed across 4 replications of the EE-GM3 event in the original Jack background, grown under the same treatment and environmental conditions. Hence, tolerance to the relevant herbicides across a broad range of germplasm was observed for plants comprising EE-GM3.

Furthermore, plants containing the event EE-GM3 had normal leaf, flower and pod morphology, excellent fertility, and showed no disease or abnormal insect susceptibility in multiple genetic backgrounds. During introgression into multiple genetic backgrounds no aberrant problems or abnormalities were observed.

In one season, a 10 location study was designed to compare the agronomic performance of double herbicide tolerant soybean comprising transformation event EE-GM3 to the transformation parent variety, Jack and some non-transgenic soybean varieties. Using a randomized complete block design, EE-GM3 plants were grown in replicated plots with either conventional weed control or with the intended herbicides, glyphosate and isoxaflutole. Plots with soybean plants containing transformation event EE-GM3 were sprayed with isoxaflutole herbicide at a target rate of 70 grams ai/Ha and with glyphosate herbicide at a target rate of 1060 grams ai/Ha. Herbicide application was made to these plants as a foliar spray at about the V4-V5 plant growth stage. Agronomic observations were made in the early, mid and late season. The plant density (parameter; stand count) was higher for the Jack and the non-transgenic variety plots than in the event EE-GM3 plots by one standard deviation. The early stand count difference may have been the result of seed lot quality, as the EE-GM3 planting seed was produced in counter season nursery, while the seed of the non-transgenic varieties was produced in the contiguous US, normal production season. However, the number of days to achieve 50% emergence and the plant vigor ratings were the same, indicating that the seed lots were comparable for these performance parameters. In the late season stand counts, Jack and the non-transgenic varieties remained different by one standard deviation from EE-GM3 plants. Plot yields of EE-GM3 event plants were also lower than those of Jack by one standard deviation, perhaps a result of the lower plant density of the EE-GM3 event plots. The yield of the non-transgenic varieties was more than Jack as could be expected because of the advancement in yield potential found in more recent varieties.

In one trial, plant health ratings were made at three growth stages: V4-5, R1 and full maturity. The first evaluation was shortly after the intended herbicide application. At the time of the final plant health evaluation, the EE-GM3-containing plants sprayed with both herbicides had the same score as the unsprayed Jack plants, or the unsprayed plants comprising EE-GM3. In ratings by the agronomic staff, the herbicide-sprayed plants received a health rating of 3-4 (moderate injury) at the V4-5 and R1 plant growth stages. The unsprayed plants (untransformed Jack or soybean plants containing EE-GM3) were rated as 4.6-4.8 (rating of 5 indicates no injury). At the final plant health rating, all the plots received the same rating of 5 (no injury).

One trial season was one of exceptional rainfall and crop injury in the EE-GM3 plants following the intended herbicide was more obvious than observed in other seasons. The field evaluations also included monitoring of the fitness characters (reproduction, disease resistance, fecundity, seed dispersal, dormancy, persistence). For the reproductive characteristics; days to emergence, days to 50% flowering and days to 90% pods maturing, the EE-GM3 and Jack plants were not different. No difference was noted in the reaction to natural infestations of plant diseases and insect pests. Although EE-GM3 produced less ultimate yield than Jack, no difference in fecundity (100 seed weight) was found. The assessment of seed dispersal parameters (pod shattering and plant lodging) found EE-GM3 and Jack to have the same pod shattering score, but found EE-GM3 plants to be less prone to lodging. Evaluation of seed harvested from the 10 locations found no concerns raised by germination or dormancy testing.

In these trials during the season with exceptional rainfall, the final yield of EE-GM3 plants, regardless of the weed control treatment, was less than the yield of Jack by one standard deviation (perhaps a result of the lower plant density of the EE-GM3 event plots). In the exceptionally wet season, crop injury (bleaching in 10-30% of the crop area) was reported for EE-GM3 plots up to six weeks following foliar application of the glyphosate and isoxaflutole herbicides. However, by maturity, "no injury" plant health ratings were assigned to all the plots. Replicated multi-location field trials with EE-GM3 introgressed in elite soybean cultivar background, when compared to near-isogenic sister lines not containing the transgene, are expected to show no yield difference between plants containing event EE-GM3 and the near-isogenic lines (in the absence of herbicide treatment).

Further, in a replicated field trial significant crop tolerance (bleaching of less than 10%) was found in soybean plants comprising EE-GM3 when treated either pre- or post-emergence with IFT (70 gr ai/ha with 0.5% NIS, Agridex), but also significant crop tolerance (bleaching of less than 10%) was found in soybean plants comprising EE-GM3 when treated with a post-emergence application of pyrasulfotole (35 gr ai/ha with 0.5% NIS, Agridex), another HPPD inhibitor herbicide.

1.2.2 Identification of the Flanking Regions and Foreign DNA of Elite Event EE-GM3

The sequence of the regions flanking the foreign DNA comprising the herbicide tolerance genes in the EE-GM3 elite event was determined to be as follows:

1.2.2.1. Right (5') Flanking Region

The fragment identified as comprising the 5' flanking region was sequenced and its nucleotide sequence is represented in SEQ ID No. 2. The sequence between nucleotide 1 and 1451 corresponds to plant DNA, while the sequence between nucleotide 1452 and 1843 corresponds to foreign DNA.

1.2.2.2. Left (3') Flanking Region

The fragment identified as comprising the 3' flanking region was sequenced and its nucleotide sequence is represented in SEQ ID No. 3. The sequence between nucleotide 1 and 240 corresponds to foreign DNA, while the sequence between nucleotide 241 and 1408 corresponds to plant DNA.

1.2.2.3. Foreign DNA Comprising the Herbicide Tolerance Genes of EE-GM3

Using different molecular techniques, it has been determined that the foreign DNA of elite event EE-GM3 comprising the herbicide tolerance genes contains two partial 3' histonAt sequences in a head-to-head orientation, followed by 2 almost complete copies of the SalI fragment of pSF10 arranged in head-to-tail orientation (see FIG. 1).

The foreign DNA comprising the herbicide tolerance genes of EE-GM3 thus contains in order the following sequences:

from nucleotide 1 to nucleotide 199: the nucleotide sequence corresponding to complement of the nucleotide sequence of SEQ ID 1 from nt 6760 to nt 6958;

from nucleotide 200 to nucleotide 624: the nucleotide sequence corresponding to the nucleotide sequence of SEQ ID 1 from nt 6874 to nt 7298;

from nucleotide 625 to nucleotide 7909: the nucleotide sequence corresponding to the nucleotide sequence of SEQ ID 1 from nt 7 to nt 7291;

from nucleotide 7910 to nucleotide 15163: the nucleotide sequence corresponding to the nucleotide sequence of SEQ ID 1 from nt 12 to nt 7265; and from nucleotide 15164 to nucleotide 15187: the nucleotide sequence corresponding to the nucleotide sequence of SEQ ID 3 from nt 217 to nt 240 (this sequence does not correspond to either pSF10 plasmid DNA or wt plant DNA and therefore is designated filler DNA).

This foreign DNA is preceded immediately upstream and contiguous with the foreign DNA by the 5' flanking sequence of SEQ ID No 2 from nucleotide 1 to 1451 and is followed immediately downstream and contiguous with the foreign DNA by the 3' flanking sequence of SEQ ID No 3 from nucleotide 241 to nucleotide 1408.

Confirmed full DNA sequencing of the foreign DNA and flanking DNA sequences in EE-GM3 resulted in the sequence reported in SEQ ID No. 20. In this sequence, the inserted DNA is from nucleotide position 1452 to nucleotide position 16638, and the 2 almost complete copies from pSF10 arranged in head-to-tail orientation are from nucleotide position 2257 to nucleotide position 16601. The 5' flanking DNA sequence in SEQ ID No. 20 is the sequence from nucleotide position 1 to nucleotide position 1451 in SEQ ID No. 20, and the 3' flanking DNA sequence in SEQ ID No. 20 is the sequence from nucleotide position 16639 to nucleotide position 17806 in SEQ ID No. 20.

1.3. Description of the Foreign DNA Comprising the Phosphinothricinacetyltransferase Chimeric Genes Plasmid pB2/P35SAcK is a pUC19 derived cloning vector which contains a chimeric pat gene. A description of the vector is given in Table 2 below. The nucleotide sequence thereof is represented in SEQ ID No. 11.

TABLE 2

Nucleotide positions of constituents of pB2/P35SAcK (SEQ ID No 11)

| Nucleotide positions | Description and references |
|---|---|
| 461-1003 | 35S promotor from Cauliflower Mosaic Virus |
| 1004-1011 | Synthetic polylinker derived sequences |
| 1012-1563 | Synthetic pat gene (amino acid sequence from *Streptomyces viridochromogenes*) |
| 1564-1581 | Synthetic polylinker derived sequences |
| 1582-1784 | 35S terminator from Cauliflower Mosaic Virus |

1.4. Event EE-GM1

1.4.1 Identification of EE-GM1

Herbicide-resistant soybean was developed by transformation of soybean with vector pB2/P35SAcK using direct gene transfer.

Elite event EE-GM1 was selected based on an extensive selection procedure based on good expression and stability of the herbicide resistance gene and its compatibility with optimal agronomic characteristics.

1.4.2 Identification of the Flanking Regions and Foreign DNA of Elite Event EE-GM1

1.4.2.1. Right (5') Flanking Region

The fragment identified as comprising the 5' flanking region was sequenced and its nucleotide sequence is represented in SEQ ID No. 12. The sequence between nucleotide 1 and 209 corresponds to plant DNA, while the sequence between nucleotide 210 and 720 corresponds to foreign DNA.

1.4.2.2. Left (3') Flanking Region

The fragment identified as comprising the 3' flanking region was sequenced and its nucleotide sequence is represented in SEQ ID No. 13. The sequence between nucleotide 1 and 568 corresponds to foreign DNA, while the sequence between nucleotide 569 and 1000 corresponds to plant DNA.

1.4.2.3. Foreign DNA Comprising the Herbicide Tolerance Genes of EE-GM1

Figure 3:
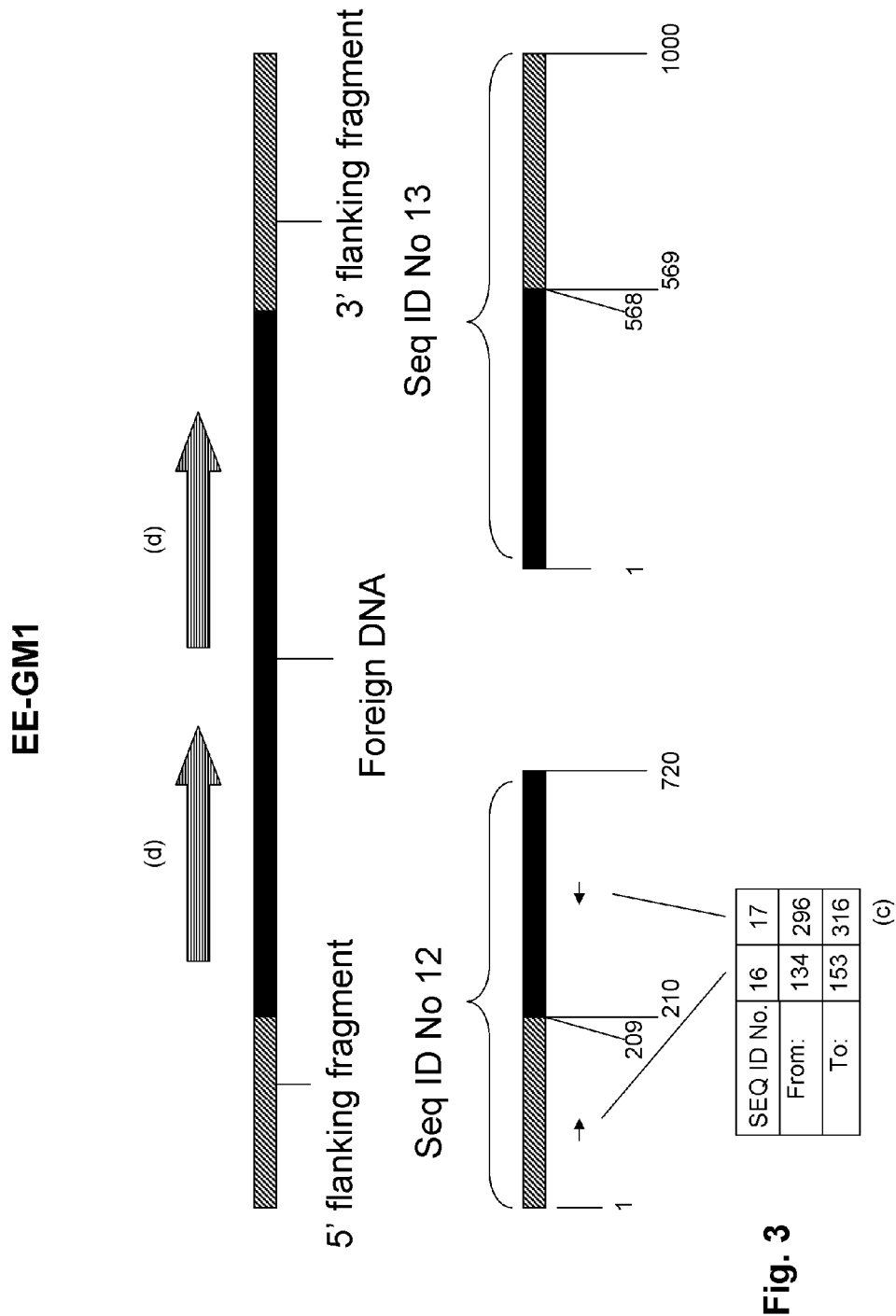
FIG. 3: Schematic representation of the relationship between the cited nucleotide sequences and primers for elite event EE-GM1. black bar: foreign DNA; hatched bar: DNA of plant origin; horizontally striped arrow (d): chimeric phosphinothricin acetyltransferase encoding gene (see SEQ ID No. 11 for composition of the chimeric gene; black arrows: oligonucleotide primers, the figures under the bars represent nucleotide positions; (c) refers to complement of the indicated nucleotide sequence; Note: the scheme is not drawn to scale.

Using different molecular techniques, it has been determined that the foreign DNA of elite event EE-GM1 comprising the herbicide tolerance gene comprises two copies of the chimeric pat gene in a direct repeat structure (see FIG. 3).

The foreign DNA comprising the herbicide tolerance genes of EE-GM1 thus contains in order the following sequences:

from nucleotide 1 to nucleotide 3122: the nucleotide sequence corresponding to the nucleotide sequence of SEQ ID 11 from nt 340 to nt 3461;

from nucleotide 3123 to nucleotide 3458: the nucleotide sequence corresponding to the complement of the nucleotide sequence of SEQ ID 11 from nt 1 to nt 336;

from nucleotide 3459 to nucleotide 4073: the nucleotide sequence corresponding to the complement of the nucleotide sequence of SEQ ID 11 from nt 3462 to nt 4076; and from nucleotide 4074 to nucleotide 6780: the nucleotide sequence corresponding to the nucleotide sequence of SEQ ID 11 from nt 337 to nt 3043; and from nucleotide 6781 to nucleotide 6790: the nucleotide sequence corresponding to the nucleotide sequence of SEQ ID 13 from nt 559 to nt 568 (this sequence does not correspond to either plasmid DNA or wt plant DNA and therefore is designated filler DNA).

This foreign DNA of EE-GM1 is preceded immediately upstream and contiguous with the foreign DNA at the 5' flanking sequence of SEQ ID No 12 from nucleotide 1 to 209 and is followed immediately downstream and contiguous with the foreign DNA at the 3' flanking sequence of SEQ ID No 13 from nucleotide 569 to nucleotide 1000.

1.5. Event EE-GM2

Herbicide-resistant soybean was developed by transformation of soybean with vector pB2/P35SAcK using direct gene transfer.

Elite event EE-GM2 was selected based on an extensive selection procedure based on good expression and stability of the herbicide resistance gene and its compatibility with optimal agronomic characteristics.

1.5.1. Identification of the Flanking Regions and Foreign DNA of Elite Event EE-GM2

1.5.1.1. Right (5') Flanking Region

The fragment identified as comprising the 5' flanking region was sequenced and its nucleotide sequence is represented in SEQ ID No. 14. The sequence between nucleotide 1 and 311 corresponds to plant DNA, while the sequence between nucleotide 312 and 810 corresponds to foreign DNA.

1.5.1.2. Left (3') Flanking Region

The fragment identified as comprising the 3' flanking region was sequenced and its nucleotide sequence is represented in SEQ ID No. 15. The sequence between nucleotide 1 and 507 corresponds to foreign DNA, while the sequence between nucleotide 569 and 1880 corresponds to plant DNA.

1.5.1.3. Foreign DNA Comprising the Herbicide Tolerance Genes of EE-GM2

Figure 4:
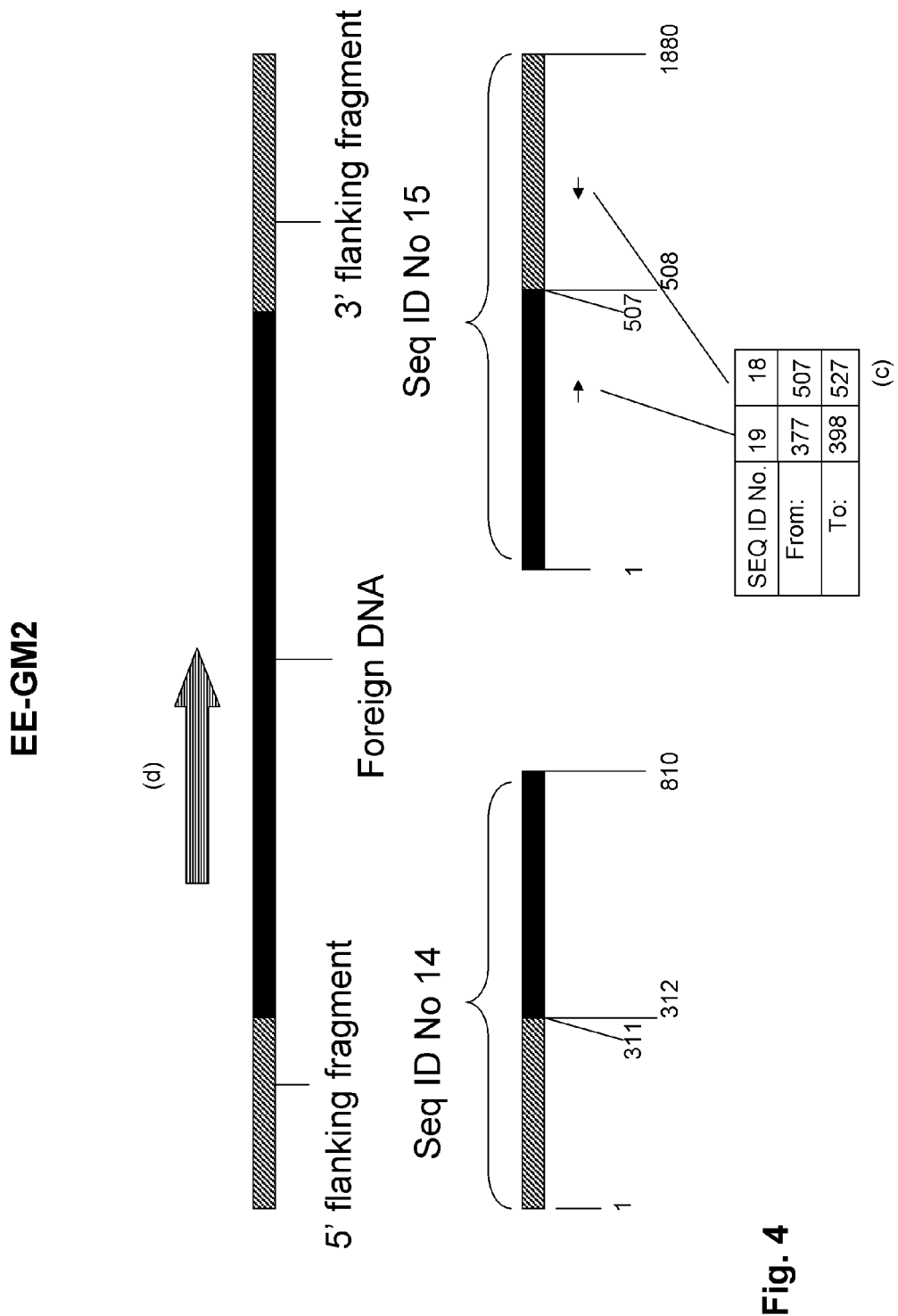
FIG. 4: Schematic representation of the relationship between the cited nucleotide sequences and primers for elite event EE-GM2. black bar: foreign DNA; hatched bar: DNA of plant origin; horizontally striped arrow (d): chimeric phosphinothricin acetyltransferase encoding gene (see SEQ ID No. 11 for composition of the chimeric gene; black arrows: oligonucleotide primers, the figures under the bars represent nucleotide positions; (c) refers to complement of the indicated nucleotide sequence; NA: not applicable. Note: the scheme is not drawn to scale.

Using different molecular techniques, it has been determined that the foreign DNA of elite event EE-GM2 comprising the herbicide tolerance gene comprises one copy of the chimeric pat gene (see FIG. 4).

The foreign DNA comprising the herbicide tolerance genes of EE-GM2 thus contains in order the following sequences:
- from nucleotide 1 to nucleotide 391: the nucleotide sequence corresponding to the nucleotide sequence of SEQ ID 11 from nt 3458 to nt 3848; and
- from nucleotide 392 to nucleotide 3436: the nucleotide sequence corresponding to the nucleotide sequence of SEQ ID 11 from nt 413 to nt 3457.

This foreign DNA of EE-GM2 is preceded immediately upstream and contiguous with the foreign DNA at the 5' flanking sequence of SEQ ID No 14 from nucleotide 1 to 311 and is followed immediately downstream and contiguous with the foreign DNA at the 3' flanking sequence of SEQ ID No 15 from nucleotide 508 to nucleotide 1880.

2. Development of Polymerase Chain Reaction Identification Protocols for EE-GM3.

2.1. Primers

Specific primers were developed which recognize sequences within the elite event.

A primer was developed which recognizes a sequence within the 3' flanking region of EE-GM3. A second primer was then selected within the sequence of the foreign DNA so that the primers span a sequence of about 263 nucleotides. The following primers were found to give particularly clear and reproducible results in a PCR reaction on EE-GM3 DNA:

```
                                          (SEQ ID No.: 4)
SOY028:    5'-ATC.gCT.TTA.ACg.TCC.CTC.Ag -3
           (target: insert DNA)

(SEQ ID No.: 5)
SOY029:    5'-CAA.ggC.CTC.gAg.ATT.ATC -3'
           (target: plant DNA)
```

Primers targeting an endogenous sequence are preferably included in the PCR cocktail. These primers serve as an internal control in unknown samples and in the DNA positive control. A positive result with the endogenous primer-pair (presence of an PCR amplified fragment of 413 bp) demonstrates that there is ample DNA of adequate quality in the genomic DNA preparation for a PCR product to be generated. The endogenous primers were selected to recognize the endogenous actin soybean gene:

```
                                          (SEQ ID No.: 9)
SOY01     5'-gTC.AgC.CAC.ACA.gTg.CCT.AT -3'

(SEQ ID No.: 10)
SOY02     5'-gTT.ACC.gTA.CAg.gTC.TTT.CC -3'
```

2.2. Amplified Fragments

The expected amplified fragments in the PCR reaction are:
For primer pair SOY01-SOY02: 413 bp (endogenous control)
For primer pair SOY028-SOY029: 263 bp (EE-GM3 elite event)

2.3. Template DNA

Template DNA was prepared from a leaf punch according to Edwards et al. (Nucleic Acid Research, 19, p 1349, 1991). When using DNA prepared with other methods, a test run utilizing different amounts of template should be done. Usually 50 ng of genomic template DNA yields the best results.

2.4. Assigned Positive and Negative Controls

To avoid false positives or negatives, it was determined that the following positive and negative controls should be included in a PCR run:
- Master Mix control (DNA negative control). This is a PCR in which no DNA is added to the reaction. When the expected result, no PCR products, is observed this indicates that the PCR cocktail was not contaminated with target DNA.
- A DNA positive control (genomic DNA sample known to contain the transgenic sequences). Successful amplification of this positive control demonstrates that the PCR was run under conditions which allow for the amplification of target sequences.
- A wild-type DNA control. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

2.5. PCR Conditions

Optimal results were obtained under the following conditions (In describing the various conditions for optimal results is meant to provide examples of such conditions. Clearly one skilled in the art could vary conditions, reagents and parameters such as using other Taq polymerases, and achieve desirable results):
- the PCR mix for 25 µl reactions contains:
  - 20 ng template DNA
  - 2.5 µl 10× Amplification Buffer (supplied by the manufacturer with the Taq polymerase)
  - 0.5 µl 10 mM dNTP's
  - 0.4 µl SOY01 (10 pmoles/µl)
  - 0.4 µA SOY02 (10 pmoles/µl)
  - 0.7 µA SOY028 (10 pmoles/µl)
  - 0.7 µA SOY029 (10 pmoles/µl)
  - 0.1 µA Taq DNA polymerase (5 units/µl)
  - water up to 25 µl
- the thermocycling profile to be followed for optimal results is the following:
  - 4 min. at 95° C.
  - Followed by: 1 min. at 95° C.
  - 1 min. at 57° C.
  - 2 min. at 72° C.
  - For 5 cycles
  - Followed by: 30 sec. at 92° C.
  - 30 sec. at 57° C.
  - 1 min. at 72° C.
  - For 25 cycles
  - Followed by: 10 minutes at 72° C.

2.6. Agarose Gel Analysis

To optimally visualize the results of the PCR it was determined that between 10 and 20 µl of the PCR samples should be applied on a 1.5% agarose gel (Tris-borate buffer) with an appropriate molecular weight marker (e.g. 100 bp ladder Pharmacia).

2.7. Validation of the Results

It was determined that data from transgenic plant DNA samples within a single PCR run and a single PCR cocktail should not be acceptable unless 1) the DNA positive control shows the expected PCR products (transgenic and endogenous fragments), 2) the DNA negative control is negative for PCR amplification (no fragments) and 3) the wild-type DNA control shows the expected result (endogenous fragment amplification).

When following the PCR Identification Protocol for EE-GM3 as described above, lanes showing visible amounts of the transgenic and endogenous PCR products of the expected sizes, indicate that the corresponding plant from which the genomic template DNA was prepared, has inherited the EE-GM3 elite event. Lanes not showing visible amounts of either of the transgenic PCR products and showing visible amounts of the endogenous PCR product, indicate that the corresponding plant from which the genomic template DNA was prepared, does not comprise the elite event. Lanes not showing visible amounts of the endogenous and transgenic PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

2.8. Use of Discriminating PCR Protocol to Identify EE-GM3

Before attempting to screen unknowns, a test run, with all appropriate controls, is performed. The developed protocol might require optimization for components that may differ between labs (template DNA preparation, Taq DNA polymerase, quality of the primers, dNTP's, thermocyler, etc.).

Amplification of the endogenous sequence plays a key role in the protocol. One has to attain PCR and thermocycling conditions that amplify equimolar quantities of both the endogenous and the transgenic sequence in a known transgenic genomic DNA template. Whenever the targeted endogenous fragment is not amplified or whenever the targeted sequences are not amplified with the same ethidium bromide staining intensities, as judged by agarose gel electrophoresis, optimization of the PCR conditions may be required.

Leaf material from a number of soybean plants, some of which comprising EE-GM3 were tested according to the above-described protocol. Samples from elite event EE-GM3 and from soybean wild-type were taken as positive and negative controls, respectively.

Figure 2:
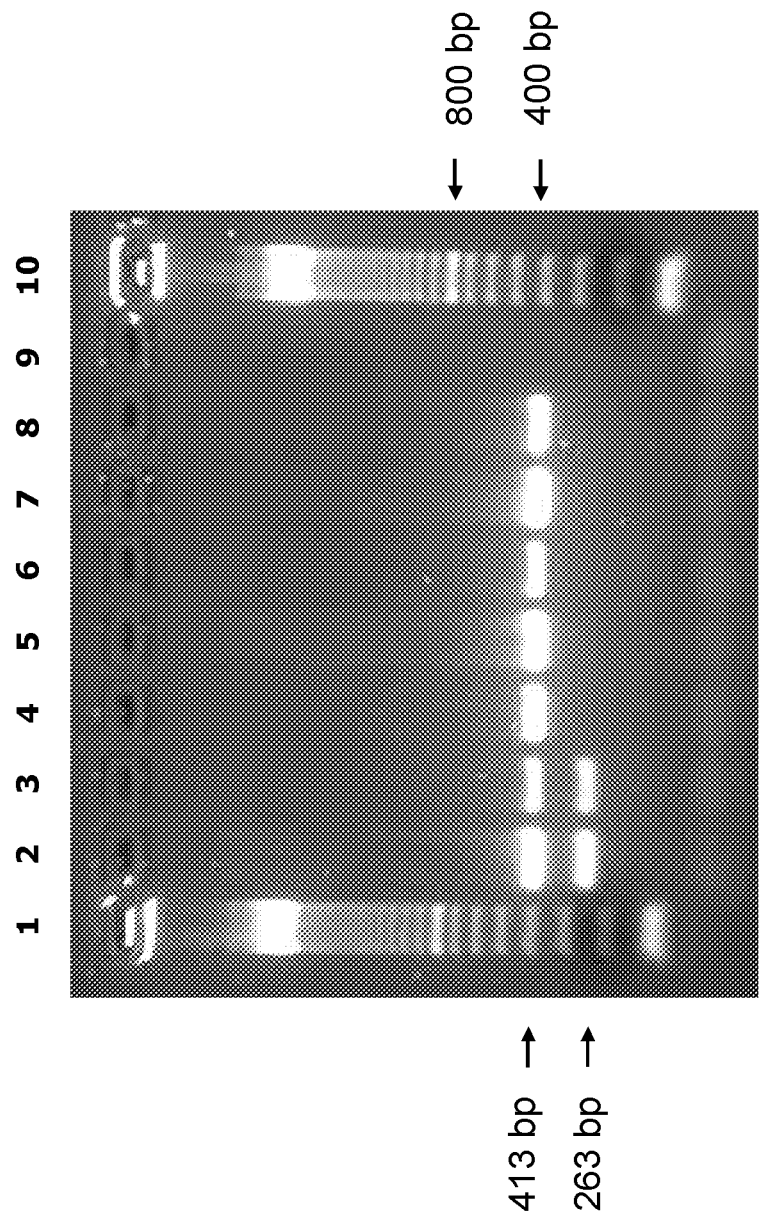
FIG. 2: Results obtained by the PCR Identification Protocol developed for EE-GM3. Loading sequence of the gel: Lane 1: Molecular weight marker (100 bp ladder); lanes 2 and 3: DNA samples from soybean plants comprising the transgenic event EE-GM3; lanes 4-7: DNA samples from transgenic soybean plants not comprising elite event EE-GM3, but comprising the same herbicide tolerance genes (other transformation events); lane 8: DNA sample from wt soybean; lane 9: no template DNA control; lane 10: molecular weight marker.

FIG. 2 illustrates the result obtained with the elite event PCR Identification Protocol for EE-GM3 on a number of soybean plant samples. The samples in lanes 2 and 3 were found to contain elite event EE-GM3 as the 263 bp band is detected, while the samples in lanes 4 to 8 do not comprise EE-GM3. Lanes 6 and 7 comprise samples from other soybean transformation events obtained using the same herbicide tolerance chimeric genes; lane 8 contains DNA from wild type soybean plants and lane 9 represents the negative control (water) sample, lanes 1 and 10 represent the Molecular Weight Marker (100 bp ladder).

2.9. dPCR Assay for EE-GM3 Detection in Bulked Seed

A discriminating PCR (dPCR) assay is set up to detect low level presence of EE-GM3 in bulked seeds. A minimum level of 0.4% (w/w) of transgenic seeds in a bulk of non transgenic seeds was successfully detected under repeatable conditions. Therefore the Limit of Detection is determined to be 0.4% (w/w).

The following primers are applied in this target PCR reaction:

Forward Primer Targeted to the T-DNA Sequence:

(SED ID No. 12)
SHA130   5'-CTA.TAT.TCT.ggT.TCC.AAT.TTA.TC-3'

Reverse Primer Targeted to the 3' Flanking Sequence:

(SEQ ID No. 13)
SMP178   5'-TgA.ggC.ACg.TAT.TgA.TgA.CC-3'

The expected amplified fragment in the PCR reaction from these primers is 115 bp.

The target PCR reaction is performed on approximately 200 ng of template DNA prepared from ground bulked seed according to a modified Gentra Puregene DNA purification extraction kit (Qiagen). When using DNA prepared with other methods, a test run using samples with known relative levels of EE-GM3 should be performed.

A validated reference system PCR reaction, targeting an endogenous sequence, should ideally be performed in a separate PCR run to verify the suitability of the DNA sample for PCR analysis to avoid false negative results.

For unknown test samples the PCR experiment should ideally include the appropriate positive and negative control samples, i.e.:

Master Mix control (DNA negative control). This is a PCR in which no DNA is added to the reaction. When the expected result (no PCR product) is observed for both the target and the reference system reaction this indicates that the PCR cocktail was not contaminated with target DNA.

A DNA positive control (genomic DNA sample known to contain the transgenic sequences). Successful amplification of this positive control demonstrates that the PCR was run under conditions which allow for the amplification of target sequences.

Also a wild-type DNA control can be added in this PCR. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

Optimal results are obtained under the following conditions:

the PCR mix for 25 μl reactions contains:
200 ng template DNA
5 μl 5× Reaction Buffer
0.25 μl 20 mM dNTP's
0.7 μl SHA130 (10 pmoles/l)
0.4 μl SMP178 (10 pmoles/l)
0.1 μl GO-Taq DNA polymerase (5 units/l)
Add water up to 25 μl
the thermocycling profile to be followed for optimal results is the following:
4 min. at 95° C.
Followed by: 1 min. at 95° C.
1 min. at 57° C.
2 min. at 72° C.
For 5 cycles
Followed by: 30 sec. at 92° C.
30 sec. at 57° C.
1 min. at 72° C.
For 30 cycles
Followed by: 10 minutes at 72° C.

To optimally visualize the results of the PCR it was determined that 25 μl of the PCR product should be applied on a 1.5% agarose gel (Tris-borate buffer) with an appropriate molecular weight marker (e.g. 50 bp ladder).

When following the PCR method as described above, lanes showing visible amounts of the target and reference system PCR products of the expected sizes, indicate that the test sample from which the genomic template DNA was prepared, contained levels of EE-GM3 elite event above the detection limit of the target reaction Lanes not showing visible amounts of the target PCR products but showing visible amounts of the reference system PCR product, indicate that the test sample from which the genomic template DNA was prepared, contained levels of EE-GM3 elite event below the detection limit of the target reaction Lanes not showing visible amounts of the endogenous and transgenic PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

3. Use of a Specific Integration Fragment as a Probe for Detection of Material Comprising EE-GM3.

A specific integration fragment of EE-GM3 is obtained by PCR amplification using specific primers SOY028 (SEQ ID No. 4) and SOY029 (SEQ ID No. 5) yielding an amplicon with the nucleotide sequence of SEQ ID No 8 or by chemical synthesis and is labeled. This integration fragment is used as a specific probe for the detection of EE-GM3 in biological samples. Nucleic acid is extracted from the samples according to standard procedures. This nucleic acid is then contacted with the specific probe under hybridization conditions which are optimized to allow formation of a hybrid. The formation of the hybrid is then detected to indicate the presence of EE-GM3 nucleic acid in the sample. Optionally, the nucleic acid in the samples is amplified using the specific primers prior to contact with the specific probe. Alternatively, the nucleic acid is labeled prior to contact with the specific probe instead of the integration fragment. Optionally, the specific probe is attached to a solid carrier (such as, but not limited to a filter, strip or beads), prior to contact with the samples.

4. Polymerase Chain Reaction Identification Protocol for EE-GM1.

4.1. Primers

Specific primers were developed which recognize sequences within the elite event. More particularly, a primer was developed which recognizes a sequence within the 5' flanking region of EE-GM1. A second primer was then selected within the sequence of the foreign DNA so that the primers span a sequence of about 183 nucleotides. The following primers were found to give particularly clear and reproducible results in a PCR reaction on EE-GM1 DNA:

```
                                            (SEQ ID No.: 16)
SOY06:   5'- ggC.gTT.CgT.AgT.gAC.TgA.gg -3'
         (target: plant DNA)

(SEQ ID No.: 17)
SOY07:   5'-gTT.TTA.CAA.CgT.CgT.gAC.Tgg-3'
         (target: insert DNA)
```

Primers targeting an endogenous sequence are preferably included in the PCR cocktail. These primers serve as an internal control in unknown samples and in the DNA positive control. A positive result with the endogenous primer-pair demonstrates that there is ample DNA of adequate quality in the genomic DNA preparation for a PCR product to be generated. The endogenous primers were selected to recognize a housekeeping gene in *Glycine max*:

```
                                            (SEQ ID No.: 9)
SOY01:   5'-gTC.AgC.CAC.ACA.gTg.CCT.AT-3'
         (located in Glycine max actin 1 gene
         (Accession J01298))

(SEQ ID No.: 10)
```

```
                                            -continued
SOY02:   5'-gTT.ACC.gTA.CAg.gTC.TTT.CC-3'
         (located in Glycine max actin 1 gene
         (Accession J01298))
```

4.2. Amplified Fragments

The expected amplified fragments in the PCR reaction are:
For primer pair SOY01-SOY02: 413 bp (endogenous control)
For primer pair SOY06-SOY07: 183 bp (EE-GM1 elite Event)

4.3. Template DNA

Template DNA was prepared from a leaf punch according to Edwards et al. (Nucleic Acid Research, 19, p 1349, 1991). When using DNA prepared with other methods, a test run utilizing different amounts of template should be done. Usually 50 ng of genomic template DNA yields the best results.

4.4. Assigned Positive and Negative Controls

To avoid false positives or negatives, it was determined that the following positive and negative controls should be included in a PCR run:

Master Mix control (DNA negative control). This is a PCR in which no DNA is added to the reaction. When the expected result, no PCR products, is observed this indicates that the PCR cocktail was not contaminated with target DNA.

A DNA positive control (genomic DNA sample known to contain the transgenic sequences). Successful amplification of this positive control demonstrates that the PCR was run under conditions which allow for the amplification of target sequences.

A wild-type DNA control. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

4.5. PCR Conditions

Optimal results were obtained under the following conditions:
the PCR mix for 25 µl reactions contains:
2.5 µl template DNA
2.5 µl 10×Amplification Buffer (supplied with Taq polymerase)
0.5 µl 10 mM dNTP's
0.5 µl SOY06 (10 pmoles/µl)
0.5 µl SOY07 (10 pmoles/µl)
0.25 µl SOY01 (10 pmoles/µl)
0.25 µl SOY02 (10 pmoles/µl)
0.1 µl Taq DNA polymerase (5 units/µl)
water up to 25 µl
the thermocycling profile to be followed for optimal results is the following:
4 min. at 95° C.
Followed by: 1 min. at 95° C.
1 min. at 57° C.
2 min. at 72° C.
For 5 cycles
Followed by: 30 sec. at 92° C.
30 sec. at 57° C.
1 min. at 72° C.
For 25 cycles
Followed by: 5 minutes at 72° C.

4.6. Agarose Gel Analysis

To optimally visualize the results of the PCR it was determined that between 10 and 20 µl of the PCR samples should be applied on a 1.5% agarose gel (Tris-borate buffer) with an appropriate molecular weight marker (e.g. 100 bp ladder Pharmacia).

4.7. Validation of the Results

It was determined that data from transgenic plant DNA samples within a single PCR run and a single PCR cocktail should not be acceptable unless 1) the DNA positive control shows the expected PCR products (transgenic and endogenous fragments), 2) the DNA negative control is negative for PCR amplification (no fragments) and 3) the wild-type DNA control shows the expected result (endogenous fragment amplification).

When following the PCR Identification Protocol for EE-GM1 as described above, lanes showing visible amounts of the transgenic and endogenous PCR products of the expected sizes, indicate that the corresponding plant from which the genomic template DNA was prepared, has inherited the EE-GM1 elite event. Lanes not showing visible amounts of either of the transgenic PCR products and showing visible amounts of the endogenous PCR product, indicate that the corresponding plant from which the genomic template DNA was prepared, does not comprise the elite event. Lanes not showing visible amounts of the endogenous and transgenic PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

4.8. Use of Discriminating PCR Protocol to Identify EE-GM1

Before attempting to screen unknowns, a test run, with all appropriate controls, has to be performed. The developed protocol might require optimization for components that may differ between labs (template DNA preparation, Taq DNA polymerase, quality of the primers, dNTP's, thermocyler, etc.).

Amplification of the endogenous sequence plays a key role in the protocol. One has to attain PCR and thermocycling conditions that amplify equimolar quantities of both the endogenous and transgenic sequence in a known transgenic genomic DNA template. Whenever the targeted endogenous fragment is not amplified or whenever the targeted sequences are not amplified with the same ethidium bromide staining intensities, as judged by agarose gel electrophoresis, optimization of the PCR conditions may be required.

*Glycine max* leaf material from a number of plants, some of which comprising EE-GM1 were tested according to the above-described protocol. Samples from elite event EE-GM1 and from *Glycine max* wild-type were taken as positive and negative controls, respectively.

Figure 5:
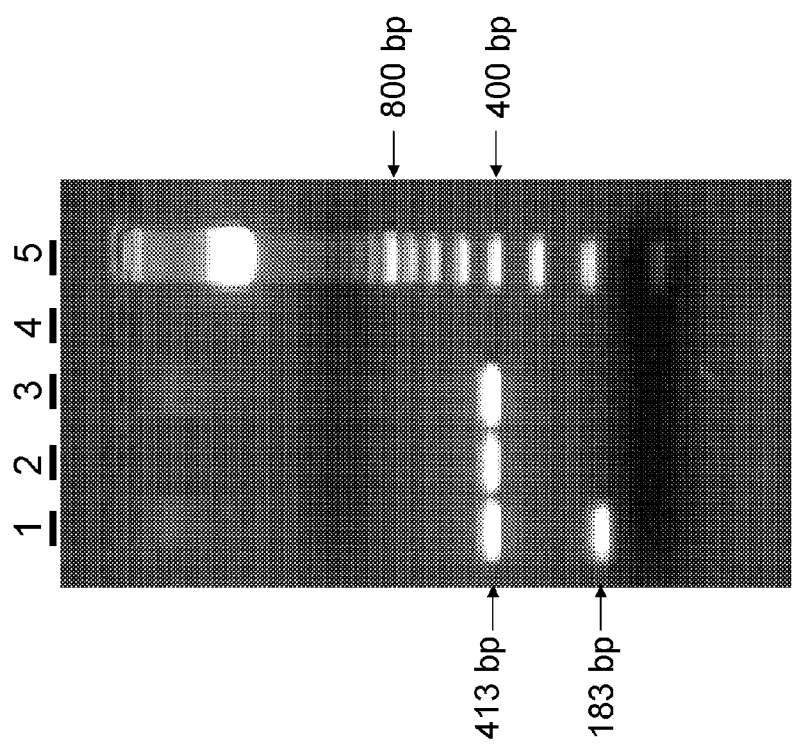
FIG. 5: PCR Identification Protocol developed for EE-GM1. Loading sequence of the gel: Lane 1: DNA sample from soybean plants comprising the transgenic event EE-GM1; lane 2: DNA sample from a transgenic soybean plant not comprising elite event EE-GM1; lane 3: control DNA samples from wild-type soybean plants; lane 4: no template control; lane 5: molecular weight marker.

FIG. 5 illustrates the result obtained with the elite event PCR Identification Protocol for EE-GM1 on a number of soybean plant samples (lanes 1 to 14). The samples in lane 1 were found to contain the elite event as the 185 bp band is detected, while the samples in lanes 2, 3 and 4 do not comprise EE-GM1. Lane 2 comprises another soybean elite event, lane 3 represents a non-transgenic *Glycine max* control; lane 4 represents the negative control (water) sample, and lane 5 represents the Molecular Weight Marker (100 bp).

5. Use of a Specific Integration Fragment as a Probe for Detection of Material Comprising EE-GM1.

A specific integration fragment of EE-GM1 is obtained by PCR amplification using specific primers SOY06 (SEQ ID No. 16) and SOY07 (SEQ ID No. 17) or by chemical synthesis and is labeled. This integration fragment is used as a specific probe for the detection of EE-GM1 in biological samples. Nucleic acid is extracted from the samples according to standard procedures. This nucleic acid is then contacted with the specific probe under hybridization conditions which are optimized to allow formation of a hybrid. The formation of the hybrid is then detected to indicate the presence of EE-GM1 nucleic acid in the sample. Optionally, the nucleic acid in the samples is amplified using the specific primers prior to contact with the specific probe. Alternatively, the nucleic acid is labeled prior to contact with the specific probe instead of the integration fragment. Optionally, the specific probe is attached to a solid carrier (such as, but not limited to a filter, strip or beads), prior to contact with the samples.

6. Polymerase Chain Reaction Identification Protocol for EE-GM2.

6.1. Primers

Specific primers were developed which recognize sequences within the elite event. More particularly, a primer was developed which recognizes a sequence within the 3' flanking region of EE-GM2. A second primer was then selected within the sequence of the foreign DNA so that the primers span a sequence of about 150 nucleotides. The following primers were found to give particularly clear and reproducible results in a PCR reaction on EE-GM2 DNA:

```
                                          (SEQ ID No.: 18)
SOY09:     5'- TgT.ggT.TAT.ggC.ggT.gCC.ATC -3'
           (target: plant DNA)
                                          (SEQ ID No.: 19)
SOY010:    5'-TgC.TAC.Agg.CAT.CgT.ggT.gTC-3'
           (target: insert DNA)
```

Primers targeting an endogenous sequence are preferably included in the PCR cocktail. These primers serve as an internal control in unknown samples and in the DNA positive control. A positive result with the endogenous primer-pair demonstrates that there is ample DNA of adequate quality in the genomic DNA preparation for a PCR product to be generated. The endogenous primers were selected to recognize a housekeeping gene in *Glycine max*:

```
                                          (SEQ ID No.: 9)
SOY01:     5'-gTC.AgC.CAC.ACA.gTg.CCT.AT-3'
           (located in Glycine max actin 1 gene
           (Accession J01298))

(SEQ ID No.: 10)
SOY02:     5'-gTT.ACC.gTA.CAg.gTC.TTT.CC-3'
           (located in Glycine max actin 1 gene
           (Accession J01298))
```

6.2. Amplified Fragments

The expected amplified fragments in the PCR reaction are:
For primer pair SOY01-SOY02: 413 bp (endogenous control)
For primer pair SOY09-SOY010: 151 bp (EE-GM2 elite Event)

6.3. Template DNA

Template DNA was prepared from a leaf punch according to Edwards et al. (Nucleic Acid Research, 19, p 1349, 1991). When using DNA prepared with other methods, a test run utilizing different amounts of template should be done. Usually 50 ng of genomic template DNA yields the best results.

6.4. Assigned Positive and Negative Controls

To avoid false positives or negatives, it was determined that the following positive and negative controls should be included in a PCR run:

Master Mix control (DNA negative control). This is a PCR in which no DNA is added to the reaction. When the expected result, no PCR products, is observed this indicates that the PCR cocktail was not contaminated with target DNA.

A DNA positive control (genomic DNA sample known to contain the transgenic sequences). Successful amplification of this positive control demonstrates that the PCR was run under conditions which allow for the amplification of target sequences.

A wild-type DNA control. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

6.5. PCR Conditions

Optimal results were obtained under the following conditions:

the PCR mix for 25 µl reactions contains:
- 2.5 µl template DNA
- 2.5 µl 10× Amplification Buffer (supplied with Taq polymerase)
- 0.5 µl 10 mM dNTP's
- 0.5 µl SOY09 (10 pmoles/µl)
- 0.5 µl SOY010 (10 pmoles/µl)
- 0.25 µl SOY01 (10 pmoles/µl)
- 0.25 µl SOY02 (10 pmoles/µl)
- 0.1 µl Taq DNA polymerase (5 units/µl)
- water up to 25 µl the thermocycling profile to be followed for optimal results is the following:
- 4 min. at 95° C.
- Followed by: 1 min. at 95° C.
- 1 min. at 57° C.
- 2 min. at 72° C.
- For 5 cycles
- Followed by: 30 sec. at 92° C.
- 30 sec. at 57° C.
- Followed by: 5 minutes at 72° C.

6.6. Agarose Gel Analysis

To optimally visualize the results of the PCR it was determined that between 10 and 20 µl of the PCR samples should be applied on a 1.5% agarose gel (Tris-borate buffer) with an appropriate molecular weight marker (e.g. 100 bp ladder Pharmacia).

6.7. Validation of the Results

It was determined that data from transgenic plant DNA samples within a single PCR run and a single PCR cocktail should not be acceptable unless 1) the DNA positive control shows the expected PCR products (transgenic and endogenous fragments), 2) the DNA negative control is negative for PCR amplification (no fragments) and 3) the wild-type DNA control shows the expected result (endogenous fragment amplification).

When following the PCR Identification Protocol for EE-GM2 as described above, lanes showing visible amounts of the transgenic and endogenous PCR products of the expected sizes, indicate that the corresponding plant from which the genomic template DNA was prepared, has inherited the EE-GM2 elite event. Lanes not showing visible amounts of either of the transgenic PCR products and showing visible amounts of the endogenous PCR product, indicate that the corresponding plant from which the genomic template DNA was prepared, does not comprise the elite event. Lanes not showing visible amounts of the endogenous and transgenic PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

6.8. Use of Discriminating PCR Protocol to Identify EE-GM2

Before attempting to screen unknowns, a test run, with all appropriate controls, has to be performed. The developed protocol might require optimization for components that may differ between labs (template DNA preparation, Taq DNA polymerase, quality of the primers, dNTP's, thermocyler, etc.).

Amplification of the endogenous sequence plays a key role in the protocol. One has to attain PCR and thermocycling conditions that amplify equimolar quantities of both the endogenous and transgenic sequence in a known transgenic genomic DNA template. Whenever the targeted endogenous fragment is not amplified or whenever the targeted sequences are not amplified with the same ethidium bromide staining intensities, as judged by agarose gel electrophoresis, optimization of the PCR conditions may be required.

*Glycine max* leaf material from a number of plants, some of which comprising EE-GM2 were tested according to the above-described protocol. Samples from elite event EE-GM2 and from *Glycine max* wild-type were taken as positive and negative controls, respectively.

Figure 6:
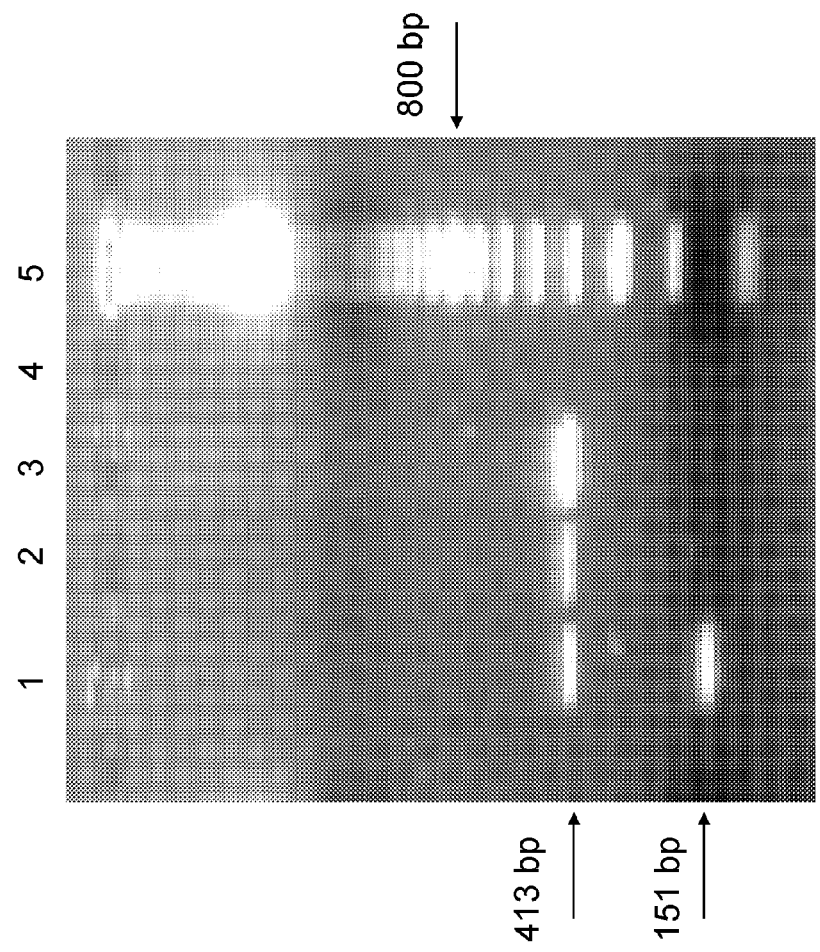
FIG. 6: PCR Identification Protocol developed for EE-GM2. Loading sequence of the gel: Lane 1: DNA sample from soybean plants comprising the transgenic event EE-GM2; lane 2: DNA sample from a transgenic soybean plant not comprising elite event EE-GM2; lane 3: control DNA samples from wild-type soybean plants; lane 4: no template control; lane 5: molecular weight marker.

FIG. 6 illustrates the result obtained with the elite event PCR Identification Protocol for EE-GM2 on a number of soybean plant samples (lanes 1 to 14). The samples in lane 1 were found to contain the elite event as the 185 bp band is detected, while the samples in lanes 2, 3 and 4 do not comprise EE-GM2. Lane 2 comprises another soybean elite event, lane 3 represents a non-transgenic *Glycine max* control; lane 4 represents the negative control (water) sample, and lane 5 represents the Molecular Weight Marker (100 bp).

7. Use of a Specific Integration Fragment as a Probe for Detection of Material Comprising EE-GM2.

A specific integration fragment of EE-GM2 is obtained by PCR amplification using specific primers SOY09 (SEQ ID No. 18) and SOY010 (SEQ ID No. 19) or by chemical synthesis and is labeled. This integration fragment is used as a specific probe for the detection of EE-GM2 in biological samples. Nucleic acid is extracted from the samples according to standard procedures. This nucleic acid is then contacted with the specific probe under hybridization conditions which are optimized to allow formation of a hybrid. The formation of the hybrid is then detected to indicate the presence of EE-GM2 nucleic acid in the sample. Optionally, the nucleic acid in the samples is amplified using the specific primers prior to contact with the specific probe. Alternatively, the nucleic acid is labeled prior to contact with the specific probe instead of the integration fragment. Optionally, the specific probe is attached to a solid carrier (such as, but not limited to a filter, strip or beads), prior to contact with the samples.

8. Generation of Soybean Plants Comprising EE-GM3 and EE-GM1 or EE-GM3 and EE-GM2 and Assessment of Agronomic Performance of Such Plants.

A soybean plant containing a combination of elite events EE-GM3 and EE-GM1 has been obtained by conventional crossing between a parent soybean plant comprising EE-GM3 and a parent soybean plant comprising EE-GM1. Progeny plants comprising both events are identified using PCR Identification Protocols for EE-GM1 and EE-GM3 as described herein. Specifically, crosses were made with plants containing EE-GM3 and several EE-GM1 lines. Resulting F1 plants were grown and sprayed with glyphosate and glufosinate. F2 seed was harvested from F1 plants and planted (F2 plants were not sprayed). F2 single plants were pulled. F2:F3 plant rows were grown and sprayed with glyphosate and glufosinate. Rows homozygous for both EE-GM3 and EE- GM1 were identified and later harvested. Segregation data from this trial showed an expected Mendelian segregation of the events.

A soybean plant containing a combination of elite events EE-GM3 and EE-GM2 has been obtained by conventional crossing between a parent soybean plant comprising EE-GM3 and a parent soybean plant comprising EE-GM2. Progeny plants comprising both events are identified using PCR Identification Protocols for EE-GM2 and EE-GM3 as described herein. Specifically, crosses were made with plants containing EE-GM3 and plants containing EE-GM2. The resulting F1 plants were crossed to 4 conventional lines. The F1s from these crosses were grown in the field and sprayed with glyphosate and glufosinate. F2 seed harvested from F1 plants resistant to both herbicides was then planted. The F2 plants were sprayed with both glyphosate and glufosinate. Nine hundred plants tolerant to both herbicides were harvested and planted in a field trial. Expected Mendelian segregation data for the events was obtained in this trial. Approximately 40 lines homozygous for tolerance to both herbicides were selected for agronomic uniformity for further studies. These lines had good tolerance to both herbicides with good agronomic characteristics.

Field trials with such soybean plants comprising the combined events in different types of commercial germplasm are being conducted at multiple locations and various agronomic parameters of the plants are being evaluated, including plant height, height to node, stand, vigor, seed yield, and glyphosate, isoxaflutole and glufosinate tolerance levels.

9. Introgression of EE-GM3 and EE-GM1 or EE-GM2 into Preferred Cultivars.

Elite event EE-GM3 and elite event EE-GM1 or EE-GM2 are introduced by repeated back-crossing into commercial soybean cultivars such as but not limited to Soybean Cultivar 7631014 (US2009252860); Soybean Cultivar 7431014 (US2009252859); Soybean Cultivar 7925084 (US2009252858); Soybean Cultivar 7311153 (US2009252857); Soybean Cultivar S070159 (US2009252856); Soybean Cultivar 7535357 (US2009246353); Soybean Cultivar S070160 (US2009246352); Soybean Cultivar 26074414 (US2009249508); Soybean Cultivar 7509171 (US2009249507); Soybean Cultivar S070158 (US2009246351); Soybean Cultivar 7511119 (US2009249506); Soybean Cultivar 7113111 (US2009238945); Soybean cultivar S06-02RM018047 (U.S. Pat. No. 7,592,518); Soybean Cultivar 7013345 (US2009232957); Soybean Cultivar 7041461 (US2009235376); Soybean Cultivar 7549450 (US2009232956); Soybean Cultivar 7317090 (US2009232955); Soybean Cultivar 2N2V58015 (US2009226597); Soybean Cultivar 7243182 (US2009226596); Soybean Cultivar 7143182 (US2009226595); Soybean Cultivar 7043182 (US2009220673); Soybean Cultivar S070157 (US2009222950); Soybean Cultivar 306924721 (US2009220672); Soybean Cultivar 7614385 (US2009220671); Soybean Cultivar 7925118 (US2009214750); Soybean Cultivar 7821295 (US2009214749); Soybean Cultivar 7811336 (US2009214748); Soybean Cultivar S070150 (US2009214747); Soybean Cultivar 6214260 (US2009214746); Soybean Cultivar S070152 (US2009214745); Soybean Cultivar 7429331 (US2009214751); Soybean Cultivar 26034631 (US2009208634); Soybean cultivar 507-03JR108674 (U.S. Pat. No. 7,560,621); Soybean cultivar 507-03KL016279 (U.S. Pat. No. 7,560,620); Soybean cultivar S06-CL959411 (U.S. Pat. No. 7,554,017); SOYBEAN CULTIVAR SG3870NRR (US2009158453); SOYBEAN CULTIVAR HFPR-G (CA2645702); Soybean cultivar S06-02JR423016 (U.S. Pat. No. 7,521,606); Soybean cultivar S06-01JR119814 (U.S. Pat. No. 7,518,039); Soybean cultivar S06-01JR119448 (U.S. Pat. No. 7,518,038); Soybean Cultivar 6540220 (US2009055960); Soybean Cultivar S060292 (US2009055959); Soybean Cultivar S050228 (US2009055958); Soybean cultivar S06-02JR423003 (U.S. Pat. No. 7,491,873); Soybean cultivar S06-02JR423005 (U.S. Pat. No. 7,491,872); Soybean cultivar S06-02JR409114 (U.S. Pat. No. 7,485,782); Soybean cultivar S06-SJ144056 (U.S. Pat. No. 7,473,823); Soybean cultivar (U.S. Pat. No. 7,470,835); Soybean cultivar 6910450 (US2008282369); SOYBEAN CULTIVAR 6223012 (U.S. Pat. No. 7,446,246); SOYBEAN CULTIVAR 6549250 (U.S. Pat. No. 7,446,245); Soybean Cultivar 17731225 (US2008271204); Soybean Cultivar 6928285 (US2008271203); Soybean Cultivar 6736054 (US2008271169); Soybean Cultivar S060299 (US2008271199); Soybean Cultivar S060294 (US2008271202); Soybean Cultivar 6943322 (US2008271201); Soybean cultivar 5343260 (US2008263719); Soybean cultivar 6439359 (US2008263704); Soybean cultivar 6238359 (US2008263703); Soybean cultivar 6547272 (US2008263702); Soybean cultivar 6929431 (US2008263701); Soybean cultivar 6703392 (US2008263700); Soybean cultivar 6044483 (US2008263699); Soybean cultivar S050224 (US2008263698); Soybean cultivar 6719022 (US2008263697); Soybean cultivar 5826056 (US2008263696); Soybean cultivar 6265047 (US2008263724); Soybean cultivar 6928331 (US2008263695); Soybean cultivar 6719331 (US2008263694); Soybean cultivar 6636454 (US2008263693); Soybean cultivar 6226454 (US2008263718); Soybean cultivar Q0073801 (US2008256657); SOYBEAN CULTIVAR 6326393 (US2008256652); SOYBEAN CULTIVAR 6408448 (US2008256651); Soybean cultivar 6449315 (US2008250524); Soybean cultivar S060296 (US2008250523); Soybean cultivar 6012078 (US2008250522); Soybean cultivar 6342078 (US2008250521); Soybean cultivar 6419156 (US2008250520); Soybean cultivar 5723264 (US2008250519); Soybean cultivar S050225 (US2008250518); Soybean cultivar S060298 (US2008244783); Soybean cultivar 6935331 (US2008244782); Soybean cultivar 6819456 (US2008244787); Soybean cultivar S060297 (US2008244781); Soybean cultivar 6135319 (US2008244786); Soybean cultivar 6819331 (US2008244780); Soybean cultivar 6137445 (US2008244779); Soybean cultivar 6917445 (US2008244778); Soybean cultivar 6111333 (US2008244777); Soybean Cultivar S050229 (US2008244776); Soybean Cultivar 6114011 (US2008244775); Soybean Cultivar 6900358 (US2008244784); Soybean Cultivar 6345184 (US2008244774); Soybean Cultivar 6836085 (US2008244773); Soybean Cultivar 6635047 (US2008244772); Soybean Cultivar 6139105 (US2008244771); SOYBEAN CULTIVAR 6434385 (US2008244770); SOYBEAN CULTIVAR S060295 (US2008244769); Soybean Cultivar 6035184 (US2008244768); Soybean Cultivar S060293

(US2008209590); Soybean Cultivar 6733322 (US2008209594); SOYBEAN CULTIVAR 6421326 (US2008209593); Soybean Cultivar S060077 (US2008209589); SOYBEAN CULTIVAR 6600375 (US2008209592); Soybean cultivar S06-CL821457 (U.S. Pat. No. 7,420,104); Soybean cultivar S07-02KG294306 (U.S. Pat. No. 7,414,178); Soybean cultivar S06-BA046119 (U.S. Pat. No. 7,414,175); Soybean cultivar S07-02KG294307 (U.S. Pat. No. 7,411,114); Soybean Cultivar SG3865N (US2008189802); Soybean cultivar 6701475 (U.S. Pat. No. 7,408,097); Soybean Cultivar 1335025 (US2008178316); Soybean Cultivar 1686017 (US2008178315); Soybean Cultivar 2388028 (US2008178314); Soybean Cultivar 2387029 (US2008178313); Soybean cultivar S06-WW152330 (U.S. Pat. No. 7,388,129); Soybean cultivar 6424090 (U.S. Pat. No. 7,385,118); Soybean cultivar 6723322 (U.S. Pat. No. 7,385,115); Soybean cultivar SG4377NRR (U.S. Pat. No. 7,385,114); Soybean cultivar S06-02JR111334 (U.S. Pat. No. 7,381,864); Soybean cultivar 6141287 (U.S. Pat. No. 7,378,577); Soybean cultivar MT110501 (U.S. Pat. No. 7,378,576); Soybean cultivar (U.S. Pat. No. 7,378,575); Soybean cultivar S06-WW169267 (U.S. Pat. No. 7,375,261); Soybean cultivar 6223392 (U.S. Pat. No. 7,371,939); Soybean cultivar S06-CL968413 (U.S. Pat. No. 7,371,937); Soybean cultivar S06-CL951107 (U.S. Pat. No. 7,368,636); Soybean cultivar S06-MT9152077 (U.S. Pat. No. 7,361,810); Soybean Cultivar 4211676 (US2008092253); Soybean cultivar S06-M059029 (U.S. Pat. No. 7,355,101); Soybean Cultivar 6548193 (U.S. Pat. No. 7,345,228); Soybean cultivar 6440261 (U.S. Pat. No. 7,345,227); Soybean cultivar S060291 (U.S. Pat. No. 7,342,151); Soybean cultivar S06-MT9206166 (U.S. Pat. No. 7,339,094); Soybean cultivar S06-WW013107 (U.S. Pat. No. 7,339,093); Soybean cultivar S06-M03256 (U.S. Pat. No. 7,335,820); Soybean cultivar 6134466 (U.S. Pat. No. 7,332,656); Soybean cultivar S06-01JR123373 (U.S. Pat. No. 7,329,800); Soybean cultivar S06-MT9211059 (U.S. Pat. No. 7,326,831); Soybean cultivar 26170838 (US2008016590); Soybean cultivar 306612412 (US2008016588); Soybean cultivar 26660135 (US2008016587); Soybean cultivar 306734323 (US2008016586); Soybean cultivar S06-01JR122235 (U.S. Pat. No. 7,317,144); SOYBEAN CULTIVAR 5900450 (U.S. Pat. No. 7,314,986); Soybean cultivar S06-MT116260 (U.S. Pat. No. 7,314,984); Soybean cultivar S06-SJ143606 (U.S. Pat. No. 7,312,381); Soybean cultivar S06-98181-G01-35167 (U.S. Pat. No. 7,309,819); SOYBEAN CULTIVAR 26082635 (U.S. Pat. No. 7,304,219); Soybean cultivar BA922834 (U.S. Pat. No. 7,304,217); Soybean cultivar 01JR123480 (U.S. Pat. No. 7,304,216); Soybean cultivar M061422 (U.S. Pat. No. 7,304,215); Soybean cultivar 17082821 (US2007277262); Soybean cultivar 17621620 (US2007277261); Soybean cultivar 00977706 (US2007277260); Soybean cultivar S060182 (US2007277259); Soybean cultivar 26312034 (U.S. Pat. No. 7,301,078); Soybean cultivar 26143837 (U.S. Pat. No. 7,301,077); Soybean cultivar 435.TCS (US2007271626); Soybean cultivar 495.RC (US2007271625); Soybean cultivar 5306230 (U.S. Pat. No. 7,297,845); Soybean cultivar S06-WW167686 (U.S. Pat. No. 7,291,772); Soybean cultivar 6141145 (US2007245426); Soybean cultivar S050232 (US2007226829); Soybean cultivar 5333301 (US2007226828); SOYBEAN CULTIVAR S050215 (US2007226827); SOYBEAN CULTIVAR 3235020 (US2007226826); Soybean cultivar 5720482 (US2007226825); Soybean cultivar S050216 (US2007226824); Soybean Cultivar 5512112 (US2007226823); Soybean cultivar 3233021 (US2007226822); SOYBEAN CULTIVAR 1336024 (US2007226821); Soybean cultivar 5348287 (US2007226820); Soybean cultivar 5204220 (US2007226819); Soybean cultivar 6188027 (US2007226818); Soybean cultivar 4183026 (US2007226817); Soybean cultivar S06-WW157958 (U.S. Pat. No. 7,271,325); Soybean cultivar 5733056 (US2007209091); Soybean cultivar 90501911 (US2007209090); Soybean cultivar S050221 (US2007204361); SOYBEAN CULTIVAR 5802205 (US2007204360); Soybean cultivar 1000642 (US2007204359); Soybean cultivar 5420128 (US2007204358); Soybean cultivar S050222 (US2007199094); Soybean cultivar S050217 (US2007199093); SOYBEAN CULTIVAR S050223 (US2007199092); Soybean cultivar S050218 (US2007199091); Soybean cultivar 5419227 (US2007199089); Soybean cultivar 5319227 (US2007199088); Soybean cultivar 5723045 (US2007199087); SOYBEAN CULTIVAR 5051007 (US2007199086); Soybean cultivar 5826175 (US2007192893); Soybean cultivar S050231 (US2007192892); SOYBEAN CULTIVAR 5826376 (US2007192891); SOYBEAN CULTIVAR 5628386 (US2007192890); Soybean cultivar 5138236 (US2007186307); Soybean cultivar 5608398 (US2007186306); SOYBEAN CULTIVAR S050230 (US2007186305); SOYBEAN CULTIVAR 5624126 (US2007180561); SOYBEAN CULTIVAR 5019225 (US2007180560); SOYBEAN CULTIVAR 5549483 (US2007180559); SOYBEAN CULTIVAR 4189010 (US2007180551); SOYBEAN CULTIVAR 1486018 (US2007180550); SOYBEAN CULTIVAR S050235 (US2007180549); SOYBEAN CULTIVAR 5023230 (US2007180548); SOYBEAN CULTIVAR S050238 (US2007174930); SOYBEAN CULTIVAR 5830261 (US2007174928); SOYBEAN CULTIVAR S050226 (U.S. Pat. No. 7,247,772); SOYBEAN CULTIVAR 5806063 (U.S. Pat. No. 7,247,771); SOYBEAN CULTIVAR S050233 (U.S. Pat. No. 7,244,881); SOYBEAN CULTIVAR 5726085 (U.S. Pat. No. 7,241,939); Soybean cultivar MT000792 (U.S. Pat. No. 7,238,867); Soybean cultivar 5521161 (U.S. Pat. No. 7,235,718); Soybean cultivar WW109447 (U.S. Pat. No. 7,235,717); Soybean cultivar BA947474 (U.S. Pat. No. 7,220,898); Soybean cultivar 5939002 (U.S. Pat. No. 7,217,870); Soybean cultivar 5726175 (U.S. Pat. No. 7,217,869); Soybean cultivar 5432082 (U.S. Pat. No. 7,217,868); Soybean cultivar SG0850RR (U.S. Pat. No. 7,211,715); Soybean cultivar SG1750NRR (U.S. Pat. No. 7,208,658); Soybean cultivar MT017827 (U.S. Pat. No. 7,208,657); Soybean cultivar 4N2V74028 (U.S. Pat. No. 7,205,458); Soybean cultivar CL431203 (U.S. Pat. No. 7,202,400); Soybean cultivar 4N0S63222 (U.S. Pat. No. 7,199,288); Soybean cultivar 5520279 (U.S. Pat. No. 7,196,253); Soybean cultivar 5834401 (U.S. Pat. No. 7,196,252); Soybean cultivar 5621161 (U.S. Pat. No. 7,196,251); Soybean cultivar CL722114 (U.S. Pat. No. 7,196,250); Soybean cultivar 5741081 (U.S. Pat. No. 7,193,140); Soybean cultivar CL727422 (U.S. Pat. No. 7,186,895); Soybean cultivar 4N2V55022 (U.S. Pat. No. 7,183,468); Soybean cultivar 5083011 (U.S. Pat. No. 7,173,169); Soybean cultivar 5626085 (U.S. Pat. No. 7,169,976); SOYBEAN CULTIVAR S050051 (U.S. Pat. No. 7,169,974); SOYBEAN CULTIVAR 4506816 (US2006294626); Soybean cultivar WW152201 (U.S. Pat. No. 7,132,594); Soybean cultivar CL727636 (U.S. Pat. No. 7,132,593); Soybean cultivar M08851 (U.S. Pat. No. 7,126,047); Soybean cultivar 4324401 (U.S. Pat. No. 7,105, 728); Soybean cultivar S050164 (U.S. Pat. No. 7,105,727); Soybean cultivar 4136015 (US2006195931); Soybean cultivar 3133014 (US2006195930); Soybean cultivar S040132 (US2006195929); Soybean Cultivar 4328386 (US2006195928); Soybean cultivar 1339013 (US2006195927); SOYBEAN CULTIVAR 4423183 (US2006195925); Soybean cultivar S040131 (US2006195924); Soybean cultivar 4929388 (US2006195923); Soybean cultivar 4817034 (US2006195922); Soybean cultivar 4916816 (U.S. Pat. No. 7,098,385); Soybean cultivar 4713487 (US2006191032); Soybean cultivar 4348019 (US2006191031); Soybean cultivar S040122 (US2006191030); Soybean cultivar S040133 (US2006185031); Soybean cultivar CL821418 (U.S. Pat. No. 7,091,404); SOYBEAN CULTIVAR 4441080 (U.S. Pat. No. 7,091,403); Soybean cultivar 4805442 (US2006179509); Soybean cultivar 4921237 (US2006179508); Soybean cultivar 4417380 (US2006174369); Soybean cultivar 4405070 (US2006174368); Soybean cultivar 4417779 (U.S. Pat. No. 7,084,328); Soybean cultivar S040125 (US2006168678); Soybean cultivar 4909380 (U.S. Pat. No. 7,081,572); Soybean cultivar S050162 (U.S. Pat. No. 7,081,571); Soybean cultivar 6084016 (U.S. Pat. No. 7,081,570); Soybean cultivar S050163 (U.S. Pat. No. 7,078,600); Soybean cultivar S040135 (U.S. Pat. No. 7,078,598); Soybean cultivar S040117 (U.S. Pat. No. 7,078,597); Soybean cultivar M03393 (U.S. Pat. No. 7,071,391); Soybean cultivar 4145306 (U.S. Pat. No. 7,064,253); Soybean cultivar 900213 (US2006117405); Soybean cultivar 1000126 (US2006117404); Soybean cultivar 901023 (US2006117403); Soybean cultivar S040130 (U.S. Pat. No. 7,053,280); Soybean cultivar 4706198 (U.S. Pat. No. 7,053,279); Soybean cultivar S040118 (U.S. Pat. No. 7,053,278); Soybean cultivar S040119 (U.S. Pat. No. 7,053,277); Soybean cultivar S040123 (U.S. Pat. No. 7,053,276); Soybean cultivar 4442112 (U.S. Pat. No. 7,049,497); SOYBEAN CULTIVAR 917013 (U.S. Pat. No. 7,045,689); Soybean cultivar S040124 (U.S. Pat. No. 7,045,691); Soybean cultivar 4238491 (U.S. Pat. No. 7,045,690); Soybean cultivar S010136 (U.S. Pat. No. 7,041,882); Soybean cultivar 900613 (U.S. Pat. No. 7,030,297); Soybean cultivar 4337175 (U.S. Pat. No. 7,030,301); Soybean cultivar S040121 (U.S. Pat. No. 7,030,300); Soybean cultivar 4216033 (U.S. Pat. No. 7,030,299); Soybean cultivar S040128 (U.S. Pat. No. 7,022,901); Soybean cultivar S040120 (U.S. Pat. No. 7,022,900); Soybean cultivar S040127 (U.S. Pat. No. 7,019,199); Soybean cultivar S040134 (U.S. Pat. No. 7,015,378); Soybean cultivar S040129 (U.S. Pat. No. 7,015,377); Soybean cultivar 4513420 (U.S. Pat. No. 7,005,564); Soybean cultivar 943013 (US2006031958); Soybean cultivar S030136 (US2006021081); Soybean cultivar 927013 (US2006021080); Soybean cultivar 1000109 (US2006015962); Soybean cultivar 90046112 (US2006010530); Soybean cultivar 90897327 (US2006010529); Soybean cultivar 90362421 (US2006010528); Soybean cultivar 03022253 (US2006010527); Soybean cultivar 02022433 (US2006010526); Soybean cultivar 02022323 (US2006010525); Soybean cultivar 02912951 (US2006010524); Soybean cultivar 0102115 (US2006010523); Soybean cultivar 915034 (US2006010522); Soybean cultivar 0509255 (US2006010521); Soybean cultivar 4803070 (U.S. Pat. No. 6,982,368); Soybean cultivar 4704310 (U.S. Pat. No. 6,979,762); Soybean cultivar SJ919784 (US2005268362); Soybean cultivar CL615261 (US2005268361); Novel soybean (US2004199964); Soybean cultivar 0509214 (US2005210542); Soybean cultivar 70826751 (US2005193442); Soybean cultivar 0509243 (US2005193441); Soybean cultivar 0509246 (US2005193440); Soybean cultivar 0509253 (US2005193439); Soybean cultivar 0509247 (US2005193438); Soybean cultivar 0509252 (US2005193437); Soybean cultivar 0509241 (US2005193436); Soybean cultivar 0509249 (U.S. Pat. No. 6,884,927); Soybean cultivar 0509244 (US2005183158); Soybean cultivar 0509240 (US2005183157); Soybean cultivar 0509239 (US2005183156); Soybean cultivar 0509254 (US2005183155); Soybean cultivar 0509245 (US2005183154); Soybean cultivar 0509251 (US2005183153); Soybean cultivar 4283008 (U.S. Pat. No. 6,888,050); Soybean cultivar 2386009 (US2005183152); Soybean cultivar 3282002 (U.S. Pat. No. 6,870,080); Soybean cultivar 0509248 (US2005183151); Soybean cultivar 5091007 (U.S. Pat. No. 6,906,249); Soybean cultivar 0509236 (US2005166281); Soybean cultivar 0509235 (US2005166280); Soybean cultivar 0509237 (US2005166279); Soybean cultivar SG5322NRR (US2005164390); Soybean cultivar SG5030NRR (US2005166278); Soybean cultivar SG4911NRR (US2005166277); Soybean cultivar S030153 (US2005160504); Soybean cultivar S030158 (US2005144680); SOYBEAN CULTIVAR S030160 (US2005144679); Soybean cultivar S030161 (US2005144678); Soybean cultivar S030157 (US2005144677); Soybean cultivar S030155 (US2005144676); Soybean cultivar S030156 (US2005144675); SOYBEAN CULTIVAR S030159 (US2005144674); Soybean cultivar S030154 (U.S. Pat. No. 6,900,376); Soybean cultivar S020030 (US2005114929); Soybean cultivar S030010 (US2005114928); Soybean cultivar SG1431RR (US2005097629); SOYBEAN CULTIVAR SG1330NRR (US2005097642); Soybean cultivar S030150 (US2005071900); SOYBEAN CULTIVAR S022209 (US2005050601); Soybean cultivar S022217 (US2005050600); Soybean cultivar S022219 (US2005050599); Soybean cultivar S030151 (US2005050598); Soybean cultivar 0491735 (US2005022272); Soybean cultivar SO22218 (US2005022271); Soybean cultivar 6190006 (US2004268447); Soybean cultivar SG1120RR (US2004250316); Soybean cultivar 0487681 (US2004237153); Soybean cultivar 0491717 (US2004237152); Soybean cultivar SO22220 (US2004237151); Soybean cultivar 0491715 (US2004237150); Soybean cultivar 0491712 (US2004237149); Soybean cultivar 0491718 (US2004237148); Soybean cultivar 99271316 (US2004221344); Soybean cultivar SO22212 (US2004221343); Soybean cultivar 0491737 (US2004221342); Soybean cultivar SO22211 (US2004221341); Soybean cultivar SO22210 (US2004221340); Soybean cultivar SO22213 (US2004221339); Soybean cultivar 0491725 (US2004221346); Soybean cultivar 03129016 (US2004221329); Soybean cultivar SO22208 (US2004221328); Soybean cultivar SO22207 (US2004221345); Soybean cultivar 02932 (US2004210968); Soybean cultivar 94137321 (US2004205862); Soybean cultivar 94106224 (US2004205861); Soybean cultivar 94143901 (US2004205859); SOYBEAN CULTIVAR 0487685 (US2004205858); SOYBEAN CULTIVAR 92440927 (US2004205857); Soybean cultivar 0487686 (US2004205856); Soybean cultivar SO22215

(US2004205855); Soybean cultivar SO22214 (US2004205854); SOYBEAN CULTIVAR 0491726 (US2004205849); SOYBEAN CULTIVAR 92478609 (US2004205853); Soybean cultivar 922013 (U.S. Pat. No. 6,781,040); SOYBEAN CULTIVAR 0491727 (US2004205852); SOYBEAN CULTIVAR 0491728 (US2004205851); Soybean cultivar 1465003 (US2004098766); Soybean cultivar 3186004 (US2004019936); Soybean cultivar 7085005 (US2004205850); Soybean cultivar SO22204 (US2004199958); Soybean cultivar SO22206 (US2004199957); Soybean cultivar 0491731 (US2004199956); Soybean cultivar 0491733 (US2004199955); Soybean cultivar 0491738 (US2004199954); Soybean cultivar 0491732 (US2004199953); Soybean cultivar 0491729 (US2004199952); Soybean cultivar SO20011 (US2004199951); Soybean cultivar 0491739 (US2004199950); Soybean cultivar 0491730 (US2004199949); Soybean cultivar 13873 (US2004199948); Soybean cultivar 954011 (US2004181822); Soybean cultivar 010022 (US2004181831); Soybean cultivar 4181001 (US2003229926); Soybean cultivar 0491721 (US2004168228); Soybean cultivar 0491723 (U.S. Pat. No. 6,911,581); Soybean cultivar 0491716 (US2004168226); Soybean cultivar 0491713 (US2004168225); Soybean cultivar 0491711 (US2004168224); Soybean cultivar 0491722 (US2004168223); Soybean cultivar 0491724 (US2004168222); Soybean cultivar 0491720 (US2004168221); Soybean cultivar 0487682 (US2004168220); Soybean cultivar 0491714 (US2004168219); Soybean cultivar 0491719 (US2004168218); Soybean cultivar DP 5634 RR (US2003177540); Soybean Cultivar S56-D7 (US2004098765); Soybean cultivar 926877 (US2004064859); Soybean cultivar SE73753 (US2004055059); Soybean cultivar SN83594 (US2004055058); Soybean cultivar SE71112 (US2004055056); Soybean cultivar SE73090 (US2004055054); Soybean cultivar SN79526 (US2004055053); Soybean cultivar SW90702 (US2004055052); Soybean cultivar SN79525 (US2004055051); Soybean cultivar SE90345 (US2004055050); Soybean cultivar 0149928 (US2004055049); Soybean cultivar SN83780 (US2004055048); Soybean cultivar 0053840 (US2004055047); Soybean cultivar 924001 (US2004055046); Soybean cultivar 0004747 (US2004055057); Soybean cultivar 0037357 (US2004055045); Soybean cultivar SN83366 (US2004055044); Soybean cultivar SN76208 (US2004055043); Soybean cultivar 0037370 (US2004055042); Soybean cultivar SX95512 (US2004049821); Soybean cultivar 0096008 (US2004049820); Soybean cultivar SN83544 (US2004049819); Soybean cultivar 0088401 (US2004049818); Soybean cultivar SN64195 (US2004049817); Soybean cultivar 0034754 (US2004049816); Soybean cultivar SN71173 (US2004049815); Soybean cultivar SN83211 (US2004049814); Soybean cultivar 92422749 (US2004045058); Soybean cultivar 0120311 (US2004045057); Soybean cultivar S010344 (US2004003438); Soybean cultivar 70876922 (US2004003437); Soybean cultivar 924496 (US2004003436); Soybean cultivar 19705120 (US2003237116); Soybean cultivar 19704220 (US2003235914); Soybean Cultivar 19704280 (US2003237115); Soybean cultivar 19704210 (US2003237114); Soybean cultivar S37-N4 (US2003237113); Soybean cultivar 19602310 (US2003233685); Soybean cultivar 19704120 (US2003233684); Soybean cultivar 19704230 (US2003233683); Soybean cultivar 1000126 (US2003233682); Soybean cultivar 93831526 (US2003221226); Soybean cultivar 0322581 (US2003221225); Soybean cultivar 0332149 (US2003213028); Soybean cultivar 0332144 (US2003213027); Soybean cultivar 924788 (US2003213026); Soybean cultivar 924861 (US2003213025); Soybean cultivar 928070 (US2003213024); Soybean cultivar S010354 (US2003213023); Soybean cultivar S010360 (US2003213022); Soybean cultivar S010361 (US2003213021); Soybean cultivar S010363 (US2003213020); Soybean cultivar S010364 (US2003213019); Soybean cultivar 0332148 (US2003208805); Soybean cultivar 0332147 (US2003208804); Soybean cultivar 0332146 (US2003208803); Soybean cultivar 0332135 (US2003208802); Soybean cultivar 1000144 (US2003208801); Soybean cultivar 0332143 (US2003208800); Soybean cultivar 0332145 (US2003208799); Soybean cultivar S010345 (US2003204884); Soybean cultivar 0332131 (US2003204883); Soybean cultivar 0332130 (US2003204882); Soybean cultivar 0332129 (US2003204881); Soybean cultivar 0332122 (US2003204880); Soybean cultivar S010350 (US2003204879); Soybean cultivar S010355 (US2003204878); Soybean cultivar 031766 (US2003204877); Soybean cultivar S010353 (US2003204876); Soybean cultivar 0322580 (US2003200579); Soybean cultivar 0322579 (US2003200578); Soybean cultivar S010347 (US2003200577); Soybean cultivar S010349 (US2003200576); Soybean cultivar 0332141 (US2003200575); Soybean cultivar 0332142 (US2003200574); Soybean Cultivar 0332133 (US2003200573); Soybean cultivar 0332134 (US2003200572); Soybean cultivar 0332139 (US2003200571); Soybean cultivar 0332137 (US2003200570); Soybean variety XB33U08 (U.S. Pat. No. 7,598,435); Soybean variety XB27D08 (U.S. Pat. No. 7,592,519); Soybean variety XB41M08 (U.S. Pat. No. 7,589,261); Soybean variety XB05J08 (U.S. Pat. No. 7,589,260); Soybean variety XB33T08 (U.S. Pat. No. 7,589,259); Soybean variety XB30Y08 (U.S. Pat. No. 7,586,025); Soybean variety XB40U08 (U.S. Pat. No. 7,582,813); Soybean variety XB29M08 (U.S. Pat. No. 7,582,811); SOYBEAN VARIETY 93Y10 (US2009144843); SOYBEAN VARIETY D4325666 (US2009055957); SOYBEAN VARIETY D4125897 (US2009055956); SOYBEAN VARIETY D4698573 (US2009055955); SOYBEAN VARIETY D4356652 (US2009019592); SOYBEAN VARIETY D4456885 (US2009019591); SOYBEAN VARIETY D4698013 (US2009019590); SOYBEAN VARIETY D4637114 (US2009019589); SOYBEAN VARIETY D4102367 (US2009019595); SOYBEAN VARIETY D4266582 (US2009019594); SOYBEAN VARIETY D4422801 (US2009019593); SOYBEAN VARIETY D4520980 (US2009019588); SOYBEAN VARIETY D4521369 (US2009019587); SOYBEAN VARIETY D4223057 (US2009019586); SOYBEAN VARIETY D4682156

(US2009019585); SOYBEAN VARIETY D4233569 (US2008178329); SOYBEAN VARIETY 4614131
(US2009019584); SOYBEAN VARIETY D4925614 (US2008178327); SOYBEAN VARIETY 4201823
(US2009019583); SOYBEAN VARIETY D4203144 (US2008178326); SOYBEAN VARIETY 92M22
(US2009019604); SOYBEAN VARIETY D4102536 (US2008178350); SOYBEAN VARIETY 4174206
(US2009019582); SOYBEAN VARIETY D4865324 (US2008178322); SOYBEAN VARIETY 4305498
(US2009019581); SOYBEAN VARIETY D4825495 (US2008178321); SOYBEAN VARIETY 4423586
(US2009019580); SOYBEAN VARIETY D4659251 (US2008172761); SOYBEAN VARIETY 4568207
(US2009019579); SOYBEAN VARIETY D4258962 (US2008172756); SOYBEAN VARIETY 4840308
(US2009019578); SOYBEAN VARIETY D4253969 (US2008172755); SOYBEAN VARIETY 4256323
(US2009019577); SOYBEAN VARIETY D4696658 (US2008172754); SOYBEAN VARIETY 4789516 (U.S. Pat.
(US2009019603); SOYBEAN VARIETY D4256925 No. 7,399,907); SOYBEAN VARIETY 90Y40
(US2009019576); SOYBEAN VARIETY D4253681 (US2008168581); SOYBEAN VARIETY 4959932 (U.S. Pat.
(US2009019575); SOYBEAN VARIETY D4789254 No. 7,396,983); SOYBEAN VARIETY 4062885 (U.S. Pat.
(US2009019574); SOYBEAN VARIETY D4713125 No. 7,394,000); Soybean variety 4858197 (U.S. Pat. No.
(US2009019573); SOYBEAN VARIETY D4526223 7,390,940); Soybean variety 4092390 (U.S. Pat. No. 7,390,
(US2009019572); SOYBEAN VARIETY D4556201 939); Soybean variety 4735486 (U.S. Pat. No. 7,390,938);
(US2009019571); SOYBEAN VARIETY D4012368 Soybean variety 4219527 (U.S. Pat. No. 7,388,132); Soybean
(US2009019570); SOYBEAN VARIETY D4452019 variety 4599695 (U.S. Pat. No. 7,388,131); Soybean variety
(US2009019569); SOYBEAN VARIETY D4201483 4554257 (U.S. Pat. No. 7,388,130); Soybean variety 4896902
(US2009019568); SOYBEAN VARIETY D4463892 (U.S. Pat. No. 7,385,113); Soybean variety 4367308 (U.S.
(US2009019567); SOYBEAN VARIETY D4159630 Pat. No. 7,385,112); Soybean variety 4589609 (U.S. Pat. No.
(US2009019566); SOYBEAN VARIETY D4470236 7,385,111); Soybean variety 4640250 (U.S. Pat. No. 7,385,
(US2009019565); SOYBEAN VARIETY D4063284 110); Soybean variety 4540394 (U.S. Pat. No. 7,385,109);
(US2009019564); SOYBEAN VARIETY D4021792 Soybean variety 4297661 (U.S. Pat. No. 7,385,108); Soybean
(US2009013429); SOYBEAN VARIETY D4902530 variety 4958786 (U.S. Pat. No. 7,381,866); Soybean variety
(US2009013428); SOYBEAN VARIETY D4367012 4440685 (U.S. Pat. No. 7,375,262); Soybean variety 4008211
(US2009013427); SOYBEAN VARIETY D4923560 (U.S. Pat. No. 7,371,938); Soybean variety 4778469 (U.S.
(US2009013426); SOYBEAN VARIETY D4253854 Pat. No. 7,368,637); Soybean variety 4766295 (U.S. Pat. No.
(US2009013425); SOYBEAN VARIETY D4210110 7,355,103); Soybean variety 4436909 (U.S. Pat. No. 7,355,
(US2009007290); SOYBEAN VARIETY D4523081 102); Soybean variety 4812469 (U.S. Pat. No. 7,351,886);
(US2009007289); SOYBEAN VARIETY D4328762 Soybean variety 4761767 (U.S. Pat. No. 7,351,885); Soybean
(US2009007288); SOYBEAN VARIETY D4483789 variety 4142393 (U.S. Pat. No. 7,329,801); Soybean variety
(US2009007287); SOYBEAN VARIETY D4311702 4502135 (U.S. Pat. No. 7,326,832); Soybean variety 4353363
(US2009007286); SOYBEAN VARIETY D4127789 (U.S. Pat. No. 7,321,082); Soybean variety 91B42 (U.S. Pat.
(US2008313765); SOYBEAN VARIETY D4361423 No. 7,317,143); SOYBEAN VARIETY 0330739
(US2008313764); SOYBEAN VARIETY D4208814 (US2007271622); Soybean variety 0384279 (U.S. Pat. No.
(US2008313763); SOYBEAN VARIETY D4201139 7,294,768); SOYBEAN VARIETY 4175567
(US2008313762); SOYBEAN VARIETY D4120384 (US2007256187); SOYBEAN VARIETY 4336643
(US2008313761); SOYBEAN VARIETY D4572906 (US2007256186); SOYBEAN VARIETY 4671685
(US2008313760); SOYBEAN VARIETY D4301279 (US2007256185); SOYBEAN VARIETY 4309194
(US2008313759); SOYBEAN VARIETY D4422957 (US2007256190); SOYBEAN VARIETY 0330738
(US2008313758); SOYBEAN VARIETY D4256958 (US2007256184); SOYBEAN VARIETY 0045477
(US2008313757); SOYBEAN VARIETY 4074328 (US2007256183); SOYBEAN VARIETY 0437973
(US2008282366); SOYBEAN VARIETY XB47Q06 (US2007256182); SOYBEAN VARIETY 0457028
(US2008244767); SOYBEAN VARIETY XB26R06 (US2007256181); SOYBEAN VARIETY 0367478
(US2008244766); SOYBEAN VARIETY 4991629 (US2007256180); SOYBEAN VARIETY 0358232
(US2008216190); SOYBEAN VARIETY 4158090 (US2007256179); SOYBEAN VARIETY 0417158
(US2008216189); Soybean Variety XB40K07 (US2007256178); SOYBEAN VARIETY 4559809
(US2008209582); SOYBEAN VARIETY D0069201 (US2007256177); SOYBEAN VARIETY 0196172
(US2008178345); SOYBEAN VARIETY D0064801 (US2007256176); SOYBEAN VARIETY 4785923
(US2008178320); SOYBEAN VARIETY D0063801 (US2007256175); SOYBEAN VARIETY 4587513
(US2008178344); SOYBEAN VARIETY D0061501 (US2007256174); SOYBEAN VARIETY 0409670
(US2008178343); SOYBEAN VARIETY 4938051 (US2007256173); SOYBEAN VARIETY 4010165
(US2008178319); SOYBEAN VARIETY 4880500 (US2007256172); SOYBEAN VARIETY 0421133
(US2008178318); SOYBEAN VARIETY 4835953 (US2007256171); SOYBEAN VARIETY 0240187
(US2008178317); SOYBEAN VARIETY 4684181 (US2007256170); SOYBEAN VARIETY 0387907
(US2008178342); SOYBEAN VARIETY 4427363 (US2007256169); SOYBEAN VARIETY 0232405
(US2008178340); SOYBEAN VARIETY 4676311 (US2007256168); SOYBEAN VARIETY 0146529
(US2008178339); SOYBEAN VARIETY 4953710 (US2007256167); SOYBEAN VARIETY 4788561
(US2008178337); SOYBEAN VARIETY 4857548 (US2007256166); SOYBEAN VARIETY 457114
(US2008178336); SOYBEAN VARIETY 4551757 (US2007256165); SOYBEAN VARIETY 0149217
(US2008178335); SOYBEAN VARIETY 4027271 (US2007256164); SOYBEAN VARIETY 4247825
(US2008178334); SOYBEAN VARIETY 4274171 (US2007254366); SOYBEAN VARIETY 0212938
(US2008178333); SOYBEAN VARIETY 0341931 (US2007256163); SOYBEAN VARIETY 0146529
(US2008178332); SOYBEAN VARIETY 4282159 (US2007256162); SOYBEAN VARIETY 4647672
(US2008178331); SOYBEAN VARIETY 4852004 (US2007256161); SOYBEAN VARIETY 0215818
(US2008178330); SOYBEAN VARIETY 4688589 (US2007256160); SOYBEAN VARIETY 0384531

(US2007256159); SOYBEAN VARIETY 4878185 (US2007254365); SOYBEAN VARIETY 4498438 (US2007256158); SOYBEAN VARIETY 0436052 (US2007256157); SOYBEAN VARIETY 4782157 (US2007256156); SOYBEAN VARIETY 0385457 (US2007256155); SOYBEAN VARIETY 0385240 (US2007256154); SOYBEAN VARIETY 4735316 (US2007256153); SOYBEAN VARIETY 0277524 (US2007256152); SOYBEAN VARIETY 0276951 (US2007256151); Soybean Variety XB37L07 (US2007245429); Soybean Variety XB35X07 (US2007226837); Soybean Variety XB35S07 (US2007226836); Soybean Variety XB35F07 (US2007226835); Soybean Variety XB34R07 (US2007226834); Soybean Variety XB34L07 (US2007226833); Soybean Variety XB34D07 (US2007226832); Soybean Variety XB33G07 (US2007226831); Soybean Variety 98Y11 (US2007169220); Soybean variety 0137335 (U.S. Pat. No. 7,241,941); Soybean Variety XB15E07 (US2007150980); Soybean Variety 92M52 (US2007150979); Soybean Variety XB47R07 (US2007136888); Soybean Variety XB46V07 (US2007136887); Soybean Variety XB57E07 (US2007136886); Soybean Variety XB54X07 (US2007136885); Soybean Variety XB54V07 (US2007136884); Soybean Variety XB52Q07 (US2007136883); Soybean Variety XB37M07 (US2007136882); Soybean Variety XB37J07 (US2007136881); Soybean Variety XB34Q07 (US2007136880); Soybean Variety XB32S07 (US2007136879); Soybean Variety XB32J07 (US2007136878); Soybean Variety XB31R07 (US2007136877); Soybean Variety XB31J07 (US2007136876); Soybean Variety XB29K07 (US2007136875); Soybean Variety XB31H07 (US2007136874); Soybean Variety XB30G07 (US2007136873); Soybean Variety XB30E07 (US2007136872); Soybean Variety XB25E07 (US2007136871); Soybean Variety XB26X07 (US2007136870); Soybean Variety XB23L07 (US2007136869); Soybean Variety XB19Z07 (US2007136868); Soybean Variety XB19E07 (US2007136867); Soybean Variety XB18M07 (US2007136866); Soybean Variety XB18K07 (US2007136865); Soybean Variety XB18J07 (US2007136864); Soybean Variety XB17W07 (US2007136863); Soybean Variety XB17U07 (US2007136862); Soybean Variety XB15B07 (US2007136861); Soybean Variety XB12R07 (US2007136860); Soybean Variety XB11J07 (US2007136859); Soybean Variety XB04E07 (US2007136858); Soybean Variety XB02K07 (US2007136857); Soybean Variety XB49V07 (US2007136856); Soybean Variety XB48X07 (US2007136855); Soybean Variety 92M75 (US2007136854); Soybean Variety XB48W07 (US2007136853); Soybean Variety XB44G07 (US2007136852); Soybean Variety XB42K07 (US2007136851); Soybean Variety XB42H07 (US2007136850); Soybean Variety XB41J07 (US2007136849); Soybean Variety XB40Y07 (US2007136848); Soybean Variety XB40X07 (US2007136847); Soybean Variety XB39E07 (US2007136846); Soybean Variety XB38W07 (US2007136845); Soybean Variety XB38S07 (US2007136844); Soybean Variety XB23V07 (US2007136843); Soybean Variety XB31M07 (US2007130652); Soybean Variety XB28E07 (US2007130651); Soybean Variety XB25S07 (US2007130650); Soybean Variety XB21N07 (US2007130649); Soybean Variety XB03Q07 (US2007130648); Soybean Variety XB49Q07 (US2007130647); Soybean Variety XB06M07 (US2007130646); Soybean variety S04-97130-15-02 (U.S. Pat. No. 7,196,249); Soybean variety S04-97026-N99-42648-01 (U.S. Pat. No. 7,189,896); Soybean variety S05-97016-G99-21212 (U.S. Pat. No. 7,186,894); Soybean variety S05-99048-19 (U.S. Pat. No. 7,164,064); Soybean variety 92B14 (U.S. Pat. No. 7,161,065); Soybean Variety 98R31 (US2007006350); Soybean variety 505-97177-N00-22972 (U.S. Pat. No. 7,132,592); Soybean variety XB25G06 (US2006225160); Soybean variety 91M70 (US2006174381); Soybean variety XB24R06 (US2006162029); Soybean variety S03-95368-N98-52902 (U.S. Pat. No. 7,078,594); Soybean variety S05-97130-51 (U.S. Pat. No. 7,078,599); Soybean variety XB11L06 (US2006130187); Soybean variety 94B13 (U.S. Pat. No. 7,064,251); Soybean variety 94B74 (U.S. Pat. No. 7,064,250); Soybean variety XB27J06 (US2006112462); Soybean variety XB29N06 (US2006112460); Soybean variety XB28T06 (US2006112459); Soybean variety XB16W06 (US2006112458); Soybean variety XB18C06 (US2006112456); Soybean variety XB 10M06 (US2006107391); Soybean variety XB06K06 (US2006107390); Soybean variety XB28V06 (US2006107389); Soybean variety XB004A06 (US2006107388); Soybean variety XB12L06 (US2006107387); Soybean variety XB005A06 (US2006107386); Soybean variety XB25H06 (US2006107385); Soybean variety XB39WO6 (US2006107384); Soybean variety XB27K06 (US2006107383); Soybean variety XB29R06 (US2006107382); Soybean variety XB16S06 (US2006107381); Soybean variety XB36V06 (US2006107380); Soybean variety XB07N06 (US2006107379); Soybean variety XB23H06 (US2006107378); Soybean variety XB35C06 (US2006107377); Soybean variety XB32L06 (US2006107376); Soybean variety XB58P06 (US2006107375); Soybean variety XB36M06 (US2006107374); Soybean variety XB22G06 (US2006107373); Soybean variety XB36Q06 (US2006107372); Soybean variety 91M61 (US2006107371); Soybean variety XB32A06 (US2006107370); Soybean variety XB19V06 (US2006107369); Soybean variety XB43C06 (US2006107368); Soybean variety XB22N06 (US2006107367); Soybean variety XB38E06 (US2006107366); Soybean variety XB37U06 (US2006107365); Soybean variety XB37Q06 (US2006107364); Soybean variety XB00D06 (US2006107363); Soybean variety XB14N06 (US2006107362); Soybean variety XB31H06 (US2006107361); Soybean variety XB21Z06 (US2006107360); Soybean variety XB005B06 (US2006107359); Soybean variety XB15W06 (US2006107358); Soybean variety XB33N06 (US2006107357); Soybean variety XB18W06 (US2006107356); Soybean variety XB32M06 (US2006107355); Soybean variety XB19F06 (US2006107354); Soybean variety S03-95021-55-138-AB (U.S. Pat. No. 7,026,531); Soybean variety 94M41 (U.S. Pat. No. 7,002,061); Soybean variety 91M50 (U.S. Pat. No. 6,998,518); Soybean variety 92B13 (U.S. Pat. No. 6,989,475); Soybean variety 93B68 (U.S. Pat. No. 6,989,474); Soybean variety 93B09 (U.S. Pat. No. 6,979,759); Soybean variety 92M00 (U.S. Pat. No. 6,972,352); Soybean variety XB08P05 (US2005120433); Soybean variety XB26V05 (US2005150023); Soybean variety XB21R05 (US2005108795); Soybean variety XB28E05 (US2005114942); Soybean variety XB58K05 (US2005114941); Soybean variety XB27B05 (US2005114940); Soybean variety XB21S05 (US2005150022); Soybean variety XB26U05 (US2005138695); Soybean variety XB35K05 (US2005150021); Soybean variety XB18S05 (US2005120436); Soybean variety XB25C05 (US2005120435); Soybean variety 90M01 (US2005120434); Soybean variety XB22H05 (US2005150020); Soybean variety XB22K05 (US2005114939); Soybean variety XB58G05 (US2005114938); Soybean variety XB57U05 (US2005120432); Soybean variety XB49M05 (US2005120431); Soybean variety XB20D05 (US2005144683); Soybean variety XB41B05 (US2005150019); Soybean variety XB38T05 (US2005120430); Soybean variety XB13T05 (US2005120429); Soybean variety XB19Y05 (US2005120428); Soybean variety XB43D05 (US2005120427); Soybean variety XB40E05 (US2005120426); Soybean variety XB39N05 (US2005120425); Soybean variety 93M01 (US2005120424); SOYBEAN VARIETY XB31W05 (US2005223439); Soybean variety XB32C05 (US2005114937); Soybean variety XB40D05 (US2005120423); Soybean variety 92M61 (US2005120422); Soybean variety 91M91 (US2005114936); Soybean variety XB33Y05 (US2005120421); Soybean variety XB34A05 (US2005120420); Soybean variety XB13U05 (US2005114935); Soybean variety XB12K05 (US2005114934); Soybean variety XB30P05 (US2005120419); Soybean variety XB57T05 (US2005114933); Soybean variety XB17S05 (US2005114932); Soybean variety XB25Y05 (US2005114930); Soybean variety XB25S05 (US2005150017); Soybean variety XB43W04 (US2004177420); Soybean variety XB44W04 (US2004177419); Soybean variety XB53J04 (US2004199960); Soybean variety XB43V04 (US2004216192); Soybean variety XB49K04 (US2004172668); Soybean variety XB27P04 (US2004205864); Soybean variety XB29L04 (US2004177418); Soybean variety XB29K04 (US2004177417); Soybean variety XB41U04 (US2004231017); Soybean variety XB34D04 (US2004177416); Soybean variety XB09J04 (US2004172711); Soybean variety XB32Y04 (US2004194169); Soybean variety XB44D04 (US2004172710); Soybean variety XB44C04 (US2004172709); Soybean variety XB10L04 (US2004172708); Soybean variety XB19U04 (US2004172707); Soybean variety XB02F04 (US2004172706); Soybean variety XB25X04 (US2004172705); Soybean variety XB26L04 (US2004172704); Soybean variety XB11F04 (US2004172703); Soybean variety XB40Z04 (US2004177415); Soybean variety XB40Y04 (US2004181833); Soybean variety XB007C04 (US2004181832); Soybean variety 96M20 (US2004172702); Soybean variety XB39J04 (US2004172701); Soybean variety XB29A04 (US2004172700); Soybean variety XB35P04 (US2004172699); Soybean variety XB58Z04 (US2004177414); Soybean variety XB43R04 (US2004172698); Soybean variety XB35L04 (US2004172697); Soybean variety XB06H04 (US2004172696); Soybean variety XB59U04 (US2004172695); Soybean variety XB64C04 (US2004172694); Soybean variety 95M80 (US2004172693); Soybean variety XB35Q04 (US2004177413); Soybean variety XB04D04 (US2004177412); Soybean variety XB08L04 (US2004177411); Soybean variety XB18Q04 (US2004177410); Soybean variety XB16Q04 (US2004177409); Soybean variety XB55K04 (US2004172692); Soybean variety XB57M04 (US2004172691); Soybean variety XB25L04 (US2004205863); Soybean variety XB48T04 (US2004194168); Soybean variety XB42X04 (US2004199959); Soybean variety XB31T04 (US2004177408); Soybean variety XB31U04 (US2004194167); Soybean variety XB30E04 (US2004177407); Soybean variety XB31R04 (US2004177406); Soybean variety S03-95341-A98-60618 (U.S. Pat. No. 6,909,033); Soybean variety SN97-6946 (US2004168227); Soybean variety 94M70 (U.S. Pat. No. 6,864,408); Soybean variety 92M70 (U.S. Pat. No. 6,797,866); Soybean variety 92M71 (U.S. Pat. No. 6,858,782); Soybean variety 91M40 (U.S. Pat. No. 6,828,490); Soybean variety 93M80 (U.S. Pat. No. 6,849,789); Soybean variety XB39N03 (U.S. Pat. No. 6,864,407); Soybean variety 93M90 (U.S. Pat. No. 6,846,975); Soybean variety 90M90 (U.S. Pat. No. 6,852,913); Soybean variety 92M72 (U.S. Pat. No. 6,960,708); Soybean variety 91M90 (U.S. Pat. No. 6,849,788); Soybean variety 92M50 (U.S. Pat. No. 6,855,876); Soybean variety 92M30 (U.S. Pat. No. 6,951,974); Soybean variety 93M60 (U.S. Pat. No. 6,797,865); Soybean variety 93M40 (U.S. Pat. No. 6,791,016); Soybean variety 93M41 (U.S. Pat. No. 6,835,875); Soybean variety XB15P03 (U.S. Pat. No. 6,797,864); Soybean variety XB24H03 (U.S. Pat. No. 6,936,752); Soybean variety XB05A03 (U.S. Pat. No. 6,815,585); Soybean variety 92M80 (U.S. Pat. No. 6,849,787); Soybean variety XB33S03 (U.S. Pat. No. 6,855,875); Soybean variety XB48P03 (U.S. Pat. No. 6,797,863); Soybean variety XB29X03 (U.S. Pat. No. 6,806,406); Soybean variety XB02C03 (U.S. Pat. No. 6,800,795); Soybean variety XB29W03 (U.S. Pat. No. 6,858,781); Soybean variety 91M10 (U.S. Pat. No. 6,958,437); Soybean variety 92M10 (U.S. Pat. No. 6,916,975); Soybean variety XB10G03 (U.S. Pat. No. 6,806,405); Soybean variety 92M31 (U.S. Pat. No. 6,846,974); Soybean variety XB38D03 (U.S. Pat. No. 6,806,404); Soybean variety XB34N03 (U.S. Pat. No. 6,803,508); Soybean variety XB30W03 (U.S. Pat. No. 6,809,236); Soybean variety XB37J03 (U.S. Pat. No. 6,844,488); Soybean variety SE72581 (US2004148665); Soybean variety SE90076 (US2004148664); Soybean variety SD82997 (US2004148663); Soybean variety 0037393 (US2004148662); Soybean variety 0088414 (US2004148661); Soybean variety 0149926 (US2004148660); Soybean variety 0037209 (US2004148659); Soybean variety 93B36 (U.S. Pat. No. 6,833,498); Soybean variety 90B74 (U.S. Pat. No. 6,812,384); Soybean variety 90B51 (U.S. Pat. No. 6,818,809); Soybean variety 91B03 (U.S. Pat. No. 6,815,584); Soybean variety 95B43 (U.S. Pat. No. 6,818,808); Soybean variety 95B42 (U.S. Pat. No. 6,815,583); Soybean variety 92B47 (U.S. Pat. No. 6,812,383); Soybean variety SE90346 (US2004055055);

Soybean variety 0007583 (US2004010824); Soybean variety 0008079 (US2004010823); Soybean variety 502-AP98041-2-333-01 (US2003121076); Soybean variety S02-98041-2-251-01 (US2003182694); Soybean variety S02-AP98041-2-262-02 (US2003196220); Soybean variety S02-95021-55-240-BA (US2003188348); Soybean variety APA94-31572 (US2003061641); Soybean variety AP98041-1-203 (US2003056251); Soybean variety APA95-15294 (US2003061640); Soybean variety AP98041-4-117 (US2003056250); Soybean variety 91B33 (U.S. Pat. No. 6,580,018); Soybean variety 93B85 (U.S. Pat. No. 6,605,762); Soybean variety 92B76 (U.S. Pat. No. 6,610,911); Soybean variety 92B38 (U.S. Pat. No. 6,605,761); Soybean variety 94B24 (U.S. Pat. No. 6,613,967); Soybean variety 94B73 (U.S. Pat. No. 6,605,760); Soybean variety 93B86 (U.S. Pat. No. 6,610,910); Soybean variety 91B12 (U.S. Pat. No. 6,583,343); Soybean variety 95B34 (U.S. Pat. No. 6,605,759); Soybean variety 94B23 (U.S. Pat. No. 6,605,758); Soybean variety 90B11 (U.S. Pat. No. 6,583,342); Soybean variety 91B92 (U.S. Pat. No. 6,586,659); Soybean variety 95B96 (U.S. Pat. No. 6,605,757); Soybean variety 93B72 (U.S. Pat. No. 6,566,589); Soybean variety 95B97 (U.S. Pat. No. 6,613,966); Soybean variety 92B95 (U.S. Pat. No. 6,608,243); Soybean variety 93B47 (U.S. Pat. No. 6,583,341); Soybean variety 97B52 (U.S. Pat. No. 6,605,756); Soybean variety 93B15 (U.S. Pat. No. 6,617,499); Soybean variety 94B54 (U.S. Pat. No. 6,613,965); Soybean variety 93B67 (U.S. Pat. No. 6,573,433); Soybean variety 93B87 (U.S. Pat. No. 6,727,410); Soybean variety 96B51 (U.S. Pat. No. 6,613,964); Soybean variety 92B84 (U.S. Pat. No. 6,730,829); Soybean variety 92B12 (U.S. Pat. No. 6,605,755); Soybean variety 90A07 (U.S. Pat. No. 6,320,105); Soybean variety 93B26 (U.S. Pat. No. 6,342,659); Soybean variety 96B21 (U.S. Pat. No. 6,369,301); Soybean variety 92B63 (U.S. Pat. No. 6,326,529); Soybean variety 93B46 (U.S. Pat. No. 6,323,402); Soybean variety 92B75 (U.S. Pat. No. 6,362,400); Soybean variety 93B08 (U.S. Pat. No. 6,323,401); Soybean variety 97B62 (U.S. Pat. No. 6,323,400); Soybean variety 92B37 (U.S. Pat. No. 6,323,399); Soybean variety 92B56 (U.S. Pat. No. 6,339,186); Soybean variety 93B66 (U.S. Pat. No. 6,307,131); Soybean variety 92B62 (U.S. Pat. No. 6,346,657); Soybean variety 92B36 (U.S. Pat. No. 6,369,300); Soybean variety 90B73 (U.S. Pat. No. 6,316,700); Soybean variety 95B95 (U.S. Pat. No. 6,323,398); Soybean variety 93B65 (U.S. Pat. No. 6,229,074); Soybean variety 92B24 (U.S. Pat. No. 6,284,950); Soybean variety 94B53 (U.S. Pat. No. 6,235,976); Soybean variety 94B22 (U.S. Pat. No. 6,140,557); Soybean variety 93B84 (U.S. Pat. No. 6,143,956); Soybean variety 95B32 (U.S. Pat. No. 6,229,073); Soybean variety 95B53 (U.S. Pat. No. 6,147,283); Soybean variety 93B35 (U.S. Pat. No. 6,153,816); Soybean variety 93B07 (U.S. Pat. No. 6,143,955); Soybean variety 92B74 (U.S. Pat. No. 6,124,526); Soybean variety 92B35 (U.S. Pat. No. 6,166,296); Soybean variety 94B45 (U.S. Pat. No. 6,162,968); Soybean variety 96B01 (U.S. Pat. No. 6,143,954); Soybean variety 93B53 (U.S. Pat. No. 6,335,197).

It is observed that the introgression of the elite events into these cultivars does not significantly influence any of the desirable phenotypic or agronomic characteristics of these cultivars (no yield drag) while expression of the transgene, as determined by glyphosate and/or isoxaflutole or glufosinate tolerance, meets commercially acceptable levels.

The stacks may be advantageously further combined with one or more other soybean events available in the market, including but not limited to other herbicide tolerance events, such as events described in USDA-APHIS petitions: 09-349-01p, 09-201-01p, 09-183-01p, 09-082-01p, 09-015-01p, 06-354-01p, 06-271-01p, 06-178-01p, 98-238-01p, 98-014-01p, 97-008-01p, 96-068-01p, 95-335-01p, 93-258-01p, (see, e.g., the USDA's aphis website) or event MON89788 (Glyphosate tolerance) described in US 2006-282915, event DP-305423-1 (High oleic acid/ALS inhibitor tolerance) described in WO 2008/054747, MON87701 described in US2009130071, event 3560.4.3.5 described in US2009036308, or event DP-305423-1 described in US2008312082, or event BPS-CV127-9 (Event 127) of WO 2010/080829.

As used in the claims below, unless otherwise clearly indicated, the term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts.

Reference seed comprising elite event EE-GM3 was deposited as 32-RRMM-0531 at the NCIMB (Ferguson Building, Craibstone Estate, Bucksburn, Aberdeen AB9YA, Scotland) on Oct. 12, 2009, under NCIMB accession number NCIMB 41659, and the viability thereof was confirmed. All restrictions on the availability to the public of the deposited material will be irrevocably removed upon the granting of a patent on the present application. An alternative name for EE-GM3 is event FG-072, or MST-FGØ72-3.

Reference seed comprising elite event EE-GM1 was deposited as 32RR1VM0368 at the NCIMB (Ferguson Building, Craibstone Estate, Bucksburn, Aberdeen AB9YA, Scotland) on Oct. 12, 2009, under NCIMB accession number NCIMB 41658. All restrictions on the availability to the public of the deposited material will be irrevocably removed upon the granting of a patent on the present application. An alternative name for EE-GM1 is LL27, A2704-12, or ACS-GM ØØ5-3.

Reference seed comprising elite event EE-GM2 was deposited as 32CON0688 at the NCIMB (Ferguson Building, Craibstone Estate, Bucksburn, Aberdeen AB9YA, Scotland) on Oct. 12, 2009, under NCIMB accession number NCIMB 41660. All restrictions on the availability to the public of the deposited material will be irrevocably removed upon the granting of a patent on the present application. An alternative name for EE-GM2 is LL55, A5547-127, or ACS-GM ØØ6-4.

Reference seed comprising elite event EE-GM3 and EE-GM1 was deposited as 111606 soybean at the ATCC (American Type Culture Collection, 10801 University Blvd., Manassas, Va. 20110-2209, USA) on Jun. 11, 2010, under ATCC accession number PTA-11041. All restrictions on the availability to the public of the deposited material will be irrevocably removed upon the granting of a patent on the present application.

Reference seed comprising elite event EE-GM3 and EE-GM2 was deposited as 05SHX2XEB Soybean at the ATCC (American Type Culture Collection, 10801 University Blvd., Manassas, Va. 20110-2209, USA) on Jun. 11, 2010, under ATCC accession number PTA-11042. All restrictions on the availability to the public of the deposited material will be irrevocably removed upon the granting of a patent on the present application.

The above description of the invention is intended to be illustrative and not limiting.

Various changes or modifications in the embodiments described may occur to those skilled in the art. These can be made without departing from the spirit or scope of the invention.

SEQUENCE LISTING

<160> NUMBER OF SEQ ID NOS: 22

<210> SEQ ID NO 1
<211> LENGTH: 7296
<212> TYPE: DNA
<213> ORGANISM: Artificial
<220> FEATURE:
<223> OTHER INFORMATION: SalI fragment of vector pSF10
<220> FEATURE:
<221> NAME/KEY: terminator
<222> LOCATION: (188)..(479)
<223> OTHER INFORMATION: 3'nos: sequence including the 3' untranslated
      region of the nopaline synthase gene from the T-DNA of pTiT37 of
      Agrobacterium tumefaciens -complement
<220> FEATURE:
<221> NAME/KEY: misc_feature
<222> LOCATION: (480)..(1556)
<223> OTHER INFORMATION: hppdPf W336: the coding sequence of the
      4-hydroxyphenylpyruvate dioxygenase of Pseudomonas fluorescens
      strain A32 modified by the replacement of the amino acid Glycine
      336 with a Tryptophane - complement
<220> FEATURE:
<221> NAME/KEY: transit_peptide
<222> LOCATION: (1557)..(1928)
<223> OTHER INFORMATION: TPotp Y: coding sequence of an optimized
      transit peptide derivative (position 55 changed into Tyrosine),
      containing sequence of the RuBisCO small subunit genes of Zea mays
      (corn) and Helianthus annuus (sunflower)-complement
<220> FEATURE:
<221> NAME/KEY: 5'UTR
<222> LOCATION: (1929)..(2069)
<223> OTHER INFORMATION: 5'tev: sequence including the leader sequence
      of the tobacco etch virus - complement
<220> FEATURE:
<221> NAME/KEY: promoter
<222> LOCATION: (2070)..(3359)
<223> OTHER INFORMATION: Ph4a748 ABBC: sequence including the promoter
      region of the histone H4 gene of Arabidopsis thaliana, containing
      an internal duplication - complement
<220> FEATURE:
<221> NAME/KEY: promoter
<222> LOCATION: (3360)..(4374)
<223> OTHER INFORMATION: Ph4a748: sequence including the promoter region
      of the histone H4 gene of Arabidopsis thaliana
<220> FEATURE:
<221> NAME/KEY: Intron
<222> LOCATION: (4375)..(4855)
<223> OTHER INFORMATION: intron1 h3At: first intron of gene II of the
      histone H3.III variant of Arabidopsis thaliana
<220> FEATURE:
<221> NAME/KEY: transit_peptide
<222> LOCATION: (4856)..(5227)
<223> OTHER INFORMATION: TPotp C: coding sequence of the optimized
      transit peptide, containing sequence of the RuBisCO small subunit
      genes of Zea mays (corn) and Helianthus annuus (sunflower)
<220> FEATURE:
<221> NAME/KEY: misc_feature
<222> LOCATION: (5228)..(6565)
<223> OTHER INFORMATION: 2mepsps: the coding sequence of the double-
      mutant 5-enol-pyruvylshikimate-3-phosphate synthase gene of Zea
      mays (corn) (Lebrun et al., 1997)
<220> FEATURE:
<221> NAME/KEY: terminator
<222> LOCATION: (6566)..(7252)
<223> OTHER INFORMATION: 3'histonAt: sequence including the 3'
      untranslated region of the histone H4 gene of Arabidopsis thaliana
      (Chabouté et al., 1987)

<400> SEQUENCE: 1
gtcgactcta gcagatctgg ccggcccacc ggtgggccat atgggcccgc ggccgcgaat      60
tcgagctcgg tacctacctg gcgaaagggg gatgtgctgc aaggcgatta agttgggtaa     120
cgccagggtt ttcccagtca cgacgttgta aaacgacggc cagtgaattg cggccgcaat     180
tcccgatcta gtaacataga tgacaccgcg cgcgataatt tatcctagtt tgcgcgctat     240

```
attttgttttt ctatcgcgta ttaaatgtat aattgcggga ctctaatcat aaaaacccat    300
ctcataaata acgtcatgca ttacatgtta attattacat gcttaacgta attcaacaga    360
aattatatga taatcatcgc aagaccggca acaggattca atcttaagaa actttattgc    420
caaatgtttg aacgatcggg gaaattcgtc gagtcaccct cggccgggct ttttgacgct    480
taatcggcgg tcaatacacc acgacgcacc tggtcacgtt cgatggactc gaacagcgcc    540
ttgaagttcc actcgccaaa cccatcgtcg cccttgcgct ggatgaattc gaagaacacc    600
gggcccatca gggtttccga aagatctgc agcagcaggc gtttgtcgcc ttccacggaa    660
gatccgtcca gcaggatacc gcgtgcctgc agttgatcca ccggctcgcc gtggtcaggc    720
aggcggcctt cgagcatttc gtaataagtg tctggcggcg cggtcatgaa gcgcatgccg    780
attttcttca acgcgtccca ggtcttgacc aggtcgtcgg tgaggaacgc cacgtgctgg    840
atgccttcgc cgttgaactg catcaggaac tcttcgatct gccccgcgcc cttggacgac    900
tcttcgttca gcgggatgcg gatcatgccg tccggcgcac tcatggcctt ggaagtcagg    960
ccggtgtact cgcccttgat atcgaagtaa cgcgcttcac ggaagttgaa caatttctcg   1020
tagaagttgg cccagtagac catgcggccg cgatagacgt tgtgggtcag gtggtcgatg   1080
actttgagac ctgcaccgac cggattgcgc tccacacctt cgaggtacac gaagtcgatg   1140
tcgtagatcg agctgccttc gccgaaacgg tcgatcaggt acaacggcgc gccgccgatg   1200
cccttgatcg ccggcaggtt caattccatc ggcccggtgt caatatggat cggctgggcg   1260
ccgagttcca gggcgcggtt gtaggccttt tgcgagtcct tcacgcggaa cgccatgccg   1320
cacaccgacg ggccgtgttc ggccgcaaag taggaggcga tgctgttggg ctcgttgttg   1380
aggatcaggt tgatctcgcc ctggcggtac aggtgcacgt tcttggaacg gtgggtcgcg   1440
actttggtga agcccatgat ctcgaagatc ggctccaggg tacccggcgt cggcgacgcg   1500
aattcgatga attcaaagcc catcaggccc attgggtttt cgtatagatc tgccatgcac   1560
cggatccttc cgccgttgct gacgttgccg aggcttctgg aggagcggcg ggcgacgggg   1620
aggctggcgg tggacttgag cccctggaac ggagcgacgg cggtggccga cgaggccatc   1680
atcacggtgg gcgccataga cagcggcggc aggtacgaca gcgtctcgaa cttcttgttg   1740
ccgtaggccg gccacacctg catatattga actcttccac cgttgctggg aagggtggag   1800
aagtcgttag ccttcttggt ggtggggaag gcggcgttgg acttaaggcc ggtgaacgga   1860
gccaccatgt tggcctgagc aggggcggtc cggctaacgg tcgcgactga ggaggagatc   1920
gaagccatgg ctatcgttcg taaatggtga aaattttcag aaaattgctt ttgctttaaa   1980
agaaatgatt taaattgctg caatagaagt agaatgcttg attgcttgag attcgtttgt   2040
tttgtatatg ttgtgtttcg aattctagag tcgagagaaa ttgatgtctg tagaagaaga   2100
agaacggtta agagtagatt tgggtgagaa agatgtgaaa ttgttttttat aggcaaagac   2160 ggagagtcta ttttttgagc aatcagatcg catattaaat ctaacggctg agatatcgat   2220
ccgtgtgtac aataaaatga tgtataaacc gtcgatctgt tttaatcgac ggttcatatt   2280
agtgatccgc gtgatggcag tgatagccac taagaatcgt cttttgtttt acatgtggcg   2340
ccacaaatta gggtaatgaa gcggcaatat tttggaactc ggaaaataaa attgcgccat   2400
cacattattt gaaaattttc acatgctttt attttaaaaa cccacgaatt acaagttaca   2460
accgaaaaag atttataata tagtgattta tactaatttt gtagtagctt aatgtatatt   2520
gatactggaa aaacaatgac aatcatacga tccgtgtgta caataaaatg atgtataaac   2580
cgtcgatctg ttttaatcga cggttcatat tagtgatccg cgtgatggca gtgatagcca   2640
```

```
ctaagaatcg tcttttgttt tacatgtggc gccacaaatt agggtaatga agcggcaata    2700 tttggaact cggaaaataa aattgcgcca tcacattatt tgaaaatttt cacatgcttt    2760
tattttaaaa acccacgaat tacaagttac aaccgaaaaa gatttataat atagtgattt    2820
atactaattt tgtagtagct taatgtatat tgatactgga aaaacaatga caatcatatg    2880
ttagtattat caagttatcg tattgatatt gatattggaa catacaatgg gtattgcctt    2940
ctttcgacca taaatatcac caaatttaca agtttgtgt ataccaagtt atcaattgta    3000
aatgggatgt caacatttta atttcccttt gagaaactat agaccacaag aacacacttc    3060
aatagataaa gtaactattt acataagagg ttttaaaatc acattaacaa aaataattac    3120
caaccggcac tcacaaatac aaacagagca cacgacatgt caaagccaca agtaaattcg    3180
ttgagtggtg gtttcattac aattgtgtca cttgcagcac aaactatctt gctctgggaa    3240
tcatctcagc atcaaagatc atgctcactt caggggaact tagtgtatcc atgcctcgac    3300
tcatatttct cctcgacctg caggcatgca agctctagag cggccgccac cgcggtggag    3360
gtactcgagt cgcgacgtac gttcgaacaa ttggttttaa aagcttgcat gcctgcaggt    3420
cgaggagaaa tatgagtcga ggcatggata cactaagttc ccctgaagtg agcatgatct    3480
ttgatgctga tgatgattccc agagcaagat agtttgtgct gcaagtgaca caattgtaat    3540
gaaaccacca ctcaacgaat ttacttgtgg ctttgacatg tcgtgtgctc tgtttgtatt    3600
tgtgagtgcc ggttggtaat tatttttgtt aatgtgattt taaaacctct tatgtaaata    3660
gttactttat ctattgaagt gtgttcttgt ggtctatagt ttctcaaagg gaaattaaaa    3720
tgttgacatc ccatttacaa ttgataactt ggtatacaca aactttgtaa atttggtgat    3780
atttatggtc gaaagaaggc aatacccatt gtatgttcca atatcaatat caatacgata    3840
acttgataat actaacatat gattgtcatt gttttttccag tatcaatata cattaagcta    3900
ctacaaaatt agtataaatc actatattat aaatcttttt cggttgtaac ttgtaattcg    3960
tgggttttta aaataaaagc atgtgaaaat tttcaaataa tgtgatggcg caatttatt    4020 ttccgagttc caaaatattg ccgcttcatt accctaattt gtggcgccac atgtaaaaca    4080
aaagacgatt cttagtggct atcactgcca tcacgcggat cactaatatg aaccgtcgat    4140
taaaacagat cgacggttta tacatcattt tattgtacac acggatcgat atctcagccg    4200
ttagatttaa tatgcgatct gattgctcaa aaaatagact ctccgtcttt gcctataaaa    4260
acaatttcac atctttctca cccaaatcta ctcttaaccg ttcttcttct tctacagaca    4320
tcaatttctc tcgactctag aggatccaag cttatcgatt tcgaacccct caggcgaaga    4380
acaggtatga tttgtttgta attagatcag gggtttaggt cttccatta cttttttaatg    4440 tttttctgt tactgtctcc gcgatctgat tttacgacaa tagagtttcg ggtttttgtcc    4500 cattccagtt tgaaaataaa ggtccgtctt ttaagtttgc tggatcgata aacctgtgaa    4560
gattgagtct agtcgattta ttggatgatc cattcttcat cgtttttttc ttgcttcgaa    4620
gttctgtata accagatttg tctgtgtgcg attgtcatta cctagccgtg tatcgagaac    4680
tagggttttc gagtcaattt tgcccctttt ggttatatct ggttcgataa cgattcatct    4740
ggattagggt tttaagtggt gacgttagt attccattt cttcaaaatt tagttatgga    4800
taatgaaaat ccccaattga ctgttcaatt tcttgttaaa tgcgcagatc cccatggctt    4860
cgatctcctc ctcagtcgcg accgttagcc ggaccgcccc tgctcaggcc aacatggtgg    4920
ctccgttcac cggccttaag tccaacgccg ccttccccac caccaagaag gctaacgact    4980
```

```
tctccaccct tcccagcaac ggtggaagag ttcaatgtat gcaggtgtgg ccggcctacg   5040
gcaacaagaa gttcgagacg ctgtcgtacc tgccgccgct gtctatggcg cccaccgtga   5100
tgatggcctc gtcggccacc gccgtcgctc cgttccaggg gctcaagtcc accgccagcc   5160
tccccgtcgc ccgccgctcc tccagaagcc tcggcaacgt cagcaacggc ggaaggatcc   5220
ggtgcatggc cggcgccgag gagatcgtgc tgcagcccat caaggagatc tccggcaccg   5280
tcaagctgcc ggggtccaag tcgctttcca accggatcct cctactcgcc gccctgtccg   5340
aggggacaac agtggttgat aacctgctga acagtgagga tgtccactac atgctcgggg   5400
ccttgaggac tcttggtctc tctgtcgaag cggacaaagc tgccaaaaga gctgtagttg   5460
ttggctgtgg tggaaagttc ccagttgagg atgctaaaga ggaagtgcag ctcttcttgg   5520
ggaatgctgg aatcgcaatg cggtccttga cagcagctgt tactgctgct ggtgaaaatg   5580
caacttacgt gcttgatgga gtaccaagaa tgagggagag acccattggc gacttggttg   5640
tcggattgaa gcagcttggt gcagatgttg attgtttcct tggcactgac tgcccacctg   5700
ttcgtgtcaa tggaatcgga gggctacctg gtggcaaggt caagctgtct ggctccatca   5760
gcagtcagta cttgagtgcc ttgctgatgg ctgctccttt ggctcttggg gatgtggaga   5820
ttgaaatcat tgataaatta atctccattc cgtacgtcga aatgacattg agattgatgg   5880
agcgttttgg tgtgaaagca gagcattctg atagctggga cagattctac attaagggag   5940
gtcaaaaata caagtcccct aaaaatgcct atgttgaagg tgatgcctca agcgcaagct   6000
atttcttggc tggtgctgca attactggag ggactgtgac tgtggaaggt tgtggcacca   6060
ccagtttgca gggtgatgtg aagtttgctg aggtactgga tgatgggga gcgaaggtta   6120 catggaccga gactagcgta actgttactg gcccaccgcg ggagccattt gggaggaaac   6180
acctcaaggc gattgatgtc aacatgaaca agatgcctga tgtcgccatg actcttgctg   6240
tggttgccct ctttgccgat ggcccgacag ccatcagaga cgtggcttcc tggagagtaa   6300
aggagaccga gaggatggtt gcgatccgga cggagctaac caagctggga gcatctgttg   6360
aggaagggcc ggactactgc atcatcacgc cgccggagaa gctgaacgtg acggcgatcg   6420
acacgtacga cgaccacagg atggcgatgg ctttctcct tgccgcctgt gccgaggtcc   6480
ccgtcaccat ccgggaccct gggtgcaccc ggaagacctt ccccgactac ttcgatgtgc   6540
tgagcacttt cgtcaagaat taagctctag aactagtgga tcccccgatc cgcgtttgtg   6600
ttttctgggt ttctcactta agcgtctgcg ttttactttt gtattgggtt tggcgtttag   6660
tagtttgcgg tagcgttctt gttatgtgta attacgcttt ttcttcttgc ttcagcagtt   6720
tcggttgaaa tataaatcga atcaagtttc actttatcag cgttgtttta aattttggca   6780
ttaaattggt gaaaattgct tcaattttgt atctaaatag aagagacaac atgaaattcg   6840
acttttgacc tcaaatcttc gaacatttat ttcctgattt cacgatggat gaggataacg   6900
aaagggcggt tcctatgtcc gggaaagttc ccgtagaaga caatgagcaa agctactgaa   6960
acgcggacac gacgtcgcat tggtacggat atgagttaaa ccgactcaat tcctttatta   7020
agacataaac cgattttggt taaagtgtaa cagtgagctg atataaaacc gaaacaaacc   7080
ggtacaagtt tgattgagca acttgatgac aaacttcaga attttggtta ttgaatgaaa   7140
atcatagtct aatcgtaaaa aatgtacaga agaaaagcta gagcagaaca aagattctat   7200
attctggttc caatttatca tcgctttaac gtccctcaga tttgatcggg ctgcaggaat   7260
taaacgcccg ggcacgtggg atcctctaga gtcgac                             7296
```

```
<210> SEQ ID NO 2
<211> LENGTH: 1843
<212> TYPE: DNA
<213> ORGANISM: Artificial
<220> FEATURE:
<223> OTHER INFORMATION: 5' flanking region of the foreign DNA
      comprising herbicide tolerance genes in EE-GM3
<220> FEATURE:
<221> NAME/KEY: misc_feature
<222> LOCATION: (1)..(1451)
<223> OTHER INFORMATION: 5' flanking plant DNA
<220> FEATURE:
<221> NAME/KEY: misc_feature
<222> LOCATION: (1452)..(1843)
<223> OTHER INFORMATION: insert or foreign DNA

<400> SEQUENCE: 2
gacttccatg tctagattca ttgtactaag atttcaaacg atatatatat atatatatat      60
atatatattc aattacatct tttctcaaaaa acatatatgc atcgtatttt ctaatacatt     120
tttttatata tgttattagt taaaatttat taaaaatcat aaaattaagt aagtttcaca     180
taacatccaa tgatttttctc gtaattttaa gactggacta agaatatag tagtaacact      240 tctcttcaaa taatatactt tatttgcccg aggaatagca ttgccatatt gaactattag     300
gaaagctgaa catcaattgg tacacttgga tggttcccac ggtttattat tgtctacatc     360
tggtcatcca agcagaggtt atatcttcta taactcgaca aatcttcgtt gtgcctatat     420
agagttgctt gtacgactaa aacgcttata ataatcgtta tacaatctat gattcacagt     480
tatgatacgt gtatgcaata aatgaataga tagataaata tgatacaatt atacaattat     540
tctaaaatat atagaataca atatatgtat gtataaaaaa ttcataaaac accaataagc     600
atataattgc aattttgcaa aaccaaatta agaatataac tcaaatatta ctagaaacaa     660
aaaaaattat aaatcattgt cttcataaat taattctaag tatctacaaa tagaaataat     720
atgaatttta tataaaaaag taatataaat tttattcctt tcttaaattt atgaaaaata     780
atacttctat atttctatac atgtttctat acatgcgttt caatgtctga tagtgatagg     840
aaactctact gtattttcaa aagtttttt ttgtttaaat atattttttg tcatgtaatt     900
gtgtgtgttt tcatttacgt ccatgtaaaa agaaaatatt ttagttctat taaaatattt     960 tttttattt ttatccttaa aatactttaa ataatatttt ttcctattta aagcattttt    1020
tataatttaa agcgctattt aaaacgtttt tagaataaaa acataaaaca aacacatttt    1080
aaaatgattg aaatgaaaaa taaaactaat gaaaacgaaa acaatactaa attacaggaa    1140
agaaaaatat attcaaactt ttatgtttaa aggttttga atatttctct gattcgtttg    1200
aaatatgtga agaaaattaa aatatcaagt agtaggttac aacagttcgg gtgcaacagt    1260
gactatgaca gcaagataat agggccaata tatttggata cctctcttaa gacgtaaaca    1320
ttttgagcga gaaaataatg gaaaaaaaat aagtcattca aatgataata gatatataaa    1380
ttatttttta ttttaaatat cttattaata ttttttatttt tttatcatat tataaattat    1440
attatattta tgtagctttg ctcattgtct tctacgggaa ctttcccgga cataggaacc    1500 gcccttttcgt tatcctcatc catcgtgaaa tcaggaaata aatgttcgaa gatttgaggt    1560
caaaagtcga atttcatgtt gtctcttcta tttagataca aaattgaagc aattttcacc    1620
aatttaatgc caaaatttaa aacaacgctg tcctgatttc acgatggatg aggataacga    1680
aagggcggtt cctatgtccg ggaaagttcc cgtagaagac aatgagcaaa gctactgaaa    1740
cgcggacacg acgtcgcatt ggtacggata tgagttaaac cgactcaatt cctttattaa    1800
gacataaacc gattttggtt aaagtgtaac agtgagctga tat                     1843
```

```
<210> SEQ ID NO 3
<211> LENGTH: 1408
<212> TYPE: DNA
<213> ORGANISM: Artificial
<220> FEATURE:
<223> OTHER INFORMATION: 3' flanking sequence of foreign DNA comprising
      herbicide tolerance genes in EE-GM3
<220> FEATURE:
<221> NAME/KEY: misc_feature
<222> LOCATION: (1)..(240)
<223> OTHER INFORMATION: insert or foreign DNA
<220> FEATURE:
<221> NAME/KEY: misc_feature
<222> LOCATION: (241)..(1408)
<223> OTHER INFORMATION: plant DNA

<400> SEQUENCE: 3
taacagtgag ctgatataaa accgaaacaa accggtacaa gtttgattga gcaacttgat      60
gacaaacttc agaattttgg ttattgaatg aaaatcatag tctaatcgta aaaaatgtac     120
agaagaaaag ctagagcaga acaaagattc tatattctgg ttccaattta tcatcgcttt     180
aacgtccctc agatttgatc gggctgcagg aattaatgtg gttcatccgt cttttttgtta    240 atgcggtcat caatacgtgc ctcaaagatt gccaaataga ttaatgtggt tcatctccct     300
atatgttttg cttgttggat tttgctatca catgtttatt gctccaaact aattataata     360
aaatgacttt caaatgattg gtgttgacat tcttttcaaa ttgttcgctg aagaaaagat     420
aatctcgagg ccttgatttg ttaatgcttt cattaataaa taaataaaat aactcttttcc    480 aaatttcaat tcatgctttt atattgtgtg gttcatcctc atcttatgtc actattatca    540
tttcatgttt gagactttac ttggccatat ttgagaagac cttcttcatt ataggcaatt    600
ttatctccac aataatataa agaaatatct tgaattaata attattgagg atatattata    660
gggttctatg tggaactaaa gacatggtta ccccattaag agagagtata gaggaattac   720
ttttatttgc cacgaggcga cgcgacttgt atttattttg gaattgtact tttgcgtgag   780
cagtgtggct ctatgttggg gcctccactt gttggtgttt tatatatgtg aaaggaggat   840
gagggtgatg gttcatttct ttgcattatt tttgttattc gcgcgaatga tatatgccct   900
gtttttgaag attgataggg aagtccatat ataggaattg aagtgtcaaa agggtgtgag   960
tatgtgctat gataatcacc caattaatgt acatctggtg tggtgtttga atttgtaggt  1020
cattaattaa tattcctctt ggtgaagttt ggagttcttt tgcaattaca attctgtttt  1080
gtaagtgatt atgatggact tttagatgtt tctcaaacag taggtgtaaa gaaaaatggg  1140
ccctggtatg aaaatttgtt ttcactcttt ctcattcata tctttaaaaa aagaatgata  1200
attttgtaat aaaaataaaa aaatattaaa tattttctca aatcaaacaa cctttatttt  1260
ttatgccaac aataattttg ttaaagatgg agatttcaat tattatataa gagttcatta  1320
tagttgaaaa ttgaatgaat gtatatgttt acgttttttg tctcaagtga aactaagatc  1380
aaatattcat atctattgag ctggtctt                                    1408

<210> SEQ ID NO 4
<211> LENGTH: 20
<212> TYPE: DNA
<213> ORGANISM: Artificial
<220> FEATURE:
<223> OTHER INFORMATION: primer SOY028

<400> SEQUENCE: 4
atcgctttaa cgtccctcag                                                20
```

```
<210> SEQ ID NO 5
<211> LENGTH: 18
<212> TYPE: DNA
<213> ORGANISM: Artificial
<220> FEATURE:
<223> OTHER INFORMATION: primer SOY029

<400> SEQUENCE: 5
caaggcctcg agattatc                                                   18

<210> SEQ ID NO 6
<211> LENGTH: 20
<212> TYPE: DNA
<213> ORGANISM: Artificial
<220> FEATURE:
<223> OTHER INFORMATION: primer SMP187

<400> SEQUENCE: 6
atatcaaccc gtagctcgac                                                 20

<210> SEQ ID NO 7
<211> LENGTH: 23
<212> TYPE: DNA
<213> ORGANISM: Artificial
<220> FEATURE:
<223> OTHER INFORMATION: primer STV019

<400> SEQUENCE: 7
ggcattaaat tggtgaaaat tgc                                             23

<210> SEQ ID NO 8
<211> LENGTH: 263
<212> TYPE: DNA
<213> ORGANISM: Artificial
<220> FEATURE:
<223> OTHER INFORMATION: nucleotide sequence of PCR amplicon using
      primers SOY028 - SOY029

<400> SEQUENCE: 8
atcgctttaa cgtccctcag atttgatcgg gctgcaggaa ttaatgtggt tcatccgtct     60
ttttgttaat gcggtcatca atacgtgcct caaagattgc caaatagatt aatgtggttc    120
atctccctat atgttttgct tgttggattt tgctatcaca tgtttattgc tccaaactaa    180
ttataataaa atgactttca aatgattggt gttgacattc ttttcaaatt gttcgctgaa    240
gaaaagataa tctcgaggcc ttg                                            263

<210> SEQ ID NO 9
<211> LENGTH: 20
<212> TYPE: DNA
<213> ORGANISM: Artificial
<220> FEATURE:
<223> OTHER INFORMATION: primer 1 for amplification of control fragment
      (SOY01)

<400> SEQUENCE: 9
gtcagccaca cagtgcctat                                                 20

<210> SEQ ID NO 10
<211> LENGTH: 20
<212> TYPE: DNA
<213> ORGANISM: Artificial
<220> FEATURE:
<223> OTHER INFORMATION: primer 2 for amplification of control fragment
      (SOY02)
```

<400> SEQUENCE: 10
gttaccgtac aggtctttcc                                               20

<210> SEQ ID NO 11
<211> LENGTH: 4076
<212> TYPE: DNA
<213> ORGANISM: Artificial
<220> FEATURE:
<223> OTHER INFORMATION: nucleotide sequence of pB2/P35SAcK
<220> FEATURE:
<221> NAME/KEY: promoter
<222> LOCATION: (461)..(1003)
<223> OTHER INFORMATION: CamV35S promoter sequence
<220> FEATURE:
<221> NAME/KEY: misc_feature
<222> LOCATION: (1004)..(1011)
<223> OTHER INFORMATION: synthetic coding sequence for
      phosphinoacetyltransferase
<220> FEATURE:
<221> NAME/KEY: misc_feature
<222> LOCATION: (1582)..(1784)
<223> OTHER INFORMATION: CaMV 35S terminator

<400> SEQUENCE: 11
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgca acaaacata cacagcgact tatgctcaaa ttacaacggt atatatcctg    240
ccacatatgc ggtgtgaaat accgcacaga tgcgtaagga aaaataccg catcaggcgc    300 cattcgccat tcaggctgcg caactgttgg gaagggcgat cggtgcgggc ctcttcgcta    360
ttacgccagc tggcgaaagg gggatgtgct gcaaggcgat taagttgggt aacgccaggg    420
ttttcccagt cacgacgttg taaaacgacg ccagtgaat tcccatggag tcaaagattc    480
aaatagagga cctaacagaa ctcgccgtaa agactggcga acagttcata cagagtctct    540
tacgactcaa tgacaagaag aaaatcttcg tcaacatggt ggagcacgac acgcttgtct    600
actccaaaaa tatcaaagat acagtctcag aagaccaaag gcaattgag acttttcaac    660 aaagggtaat atccggaaac ctcctcggat tccattgccc agctatctgt cactttattg    720
tgaagatagt ggaaaaggaa ggtggctcct acaaatgcca tcattgcgat aaaggaaagg    780
ccatcgttga agatgcctct gccgacagtg gtcccaaaga tggacccca cccacgagga    840 gcatcgtgga aaagaagac gttccaacca cgtcttcaaa gcaagtggat tgatgtgata    900
tctccactga cgtaagggat gacgcacaat cccactatcc ttcgcaagac ccttcctcta    960
tataaggaag ttcatttcat ttggagagga cagggtaccc gggatccac catgtctccg   1020 gagaggagac cagttgagat taggccagct acagcagctg atatggccgc ggtttgtgat   1080
atcgttaacc attacattga cgtctaca gtgaacttta ggacagagcc acaaacacca   1140
caagagtgga ttgatgatct agagaggttg caagatagat acccttggtt ggttgctgag   1200
gttgagggtg ttgtggctgg tattgcttac gctgggccct ggaaggctag aacgcttac    1260 gattggacag ttgagagtac tgtttacgtg tcacataggc atcaaaggtt gggcctagga   1320
tccacattgt acacacattt gcttaagtct atggaggcgc aaggttttaa gtctgtggtt   1380
gctgttatag gccttccaaa cgatccatct gttaggttgc atgaggcttt gggatacaca   1440
gcccggggta cattgcgcgc agctggatac aagcatggtg gatggcatga tgttggtttt   1500
tggcaaaggg attttgagtt gccagctcct ccaaggccag ttaggccagt tacccagatc   1560

-continued

```
tgagtcgacc tgcaggcatg cccgctgaaa tcaccagtct ctctctacaa atctatctct   1620
ctctataata atgtgtgagt agttcccaga taagggaatt agggttctta tagggtttcg   1680
ctcatgtgtt gagcatataa gaaacccttg gtatgtattt gtatttgtaa aatacttcta   1740
tcaataaaat ttctaattcc taaaaccaaa atccagggcg agctcgaatt cgagctcggt   1800
acccggggat cctctagagt cgacctgcag gcatgcaagc ttggcgtaat catggtcata   1860
gctgtttcct gtgtgaaatt gttatccgct cacaattcca cacaacatac gagccggaag   1920
cataaagtgt aaagcctggg gtgcctaatg agtgagctaa ctcacattaa ttgcgttgcg   1980
ctcactgccc gctttccagt cgggaaacct gtcgtgccag ctgcattaat gaatcggcca   2040
acgcgcgggg agaggcggtt tgcgtattgg gcgctcttcc gcttcctcgc tcactgactc   2100
gctgcgctcg gtcgttcggc tgcggcgagc ggtatcagct cactcaaagg cggtaatacg   2160
gttatccaca gaatcagggg ataacgcagg aaagaacatg tgagcaaaag gccagcaaaa   2220
ggccaggaac cgtaaaaagg ccgcgttgct ggcgtttttc cataggctcc gcccccctga   2280
cgagcatcac aaaaatcgac gctcaagtca gaggtggcga aacccgacag gactataaag   2340
ataccaggcg tttccccctg gaagctccct cgtgcgctct cctgttccga ccctgccgct   2400
taccggatac ctgtccgcct ttctcccttc gggaagcgtg gcgctttctc atagctcacg   2460
ctgtaggtat ctcagttcgg tgtaggtcgt tcgctccaag ctgggctgtg tgcacgaacc   2520
ccccgttcag cccgaccgct gcgccttatc cggtaactat cgtcttgagt ccaacccggt   2580
aagacacgac ttatcgccac tggcagcagc cactggtaac aggattagca gagcgaggta   2640
tgtaggcggt gctacagagt tcttgaagtg gtggcctaac tacggctaca ctagaagaac   2700
agtatttggt atctgcgctc tgctgaagcc agttaccttc ggaaaaagag ttggtagctc   2760
ttgatccggc aaacaaacca ccgctggtag cggtggtttt tttgtttgca agcagcagat   2820
tacgcgcaga aaaaaaggat ctcaagaaga tcctttgatc ttttctacgg ggtctgacgc   2880
tcagtggaac gaaaactcac gttaagggat tttggtcatg agattatcaa aaaggatctt   2940
cacctagatc cttttaaatt aaaaatgaag ttttaaatca atctaaagta tatatgagta   3000
aacttggtct gacagttacc aatgcttaat cagtgaggca cctatctcag cgatctgtct   3060
atttcgttca tccatagttg cctgactccc cgtcgtgtag ataactacga tacgggaggg   3120
cttaccatct ggccccagtg ctgcaatgat accgcgagac ccacgctcac cggctccaga   3180
tttatcagca ataaaccagc cagccggaag ggccgagcgc agaagtggtc ctgcaacttt   3240
atccgcctcc atccagtcta ttaattgttg ccgggaagct agagtaagta gttcgccagt   3300
taatagtttg cgcaacgttg ttgccattgc tacaggcatc gtggtgtcac gctcgtcgtt   3360
tggtatggct tcattcagct ccggttccca acgatcaagg cgagttacat gatccccat    3420 gttgtgcaaa aaagcggtta gctccttcgg tcctccgatc gttgtcagaa gtaagttggc   3480
cgcagtgtta tcactcatgg ttatggcagc actgcataat tctcttactg tcatgccatc   3540
cgtaagatgc ttttctgtga ctggtgagta ctcaaccaag tcattctgag aatagtgtat   3600
gcggcgaccg agttgctctt gcccggcgtc aatacgggat aataccgcgc cacatagcag   3660
aactttaaaa gtgctcatca ttggaaaacg ttcttcgggg cgaaaactct caaggatctt   3720
accgctgttg agatccagtt cgatgtaacc cactcgtgca cccaactgat cttcagcatc   3780
ttttactttc accagcgttt ctgggtgagc aaaaacagga aggcaaaatg ccgcaaaaaa   3840
gggaataagg gcgacacgga aatgttgaat actcatactc ttcctttttc aatattattg   3900
```

```
aagcatttat cagggttatt gtctcatgag cggatacata tttgaatgta tttagaaaaa    3960
taaacaaata ggggttccgc gcacatttcc ccgaaaagtg ccacctgacg tctaagaaac    4020
cattattatc atgacattaa cctataaaaa taggcgtatc acgaggccct ttcgtc        4076
```

<210> SEQ ID NO 12
<211> LENGTH: 720
<212> TYPE: DNA
<213> ORGANISM: Artificial
<220> FEATURE:
<223> OTHER INFORMATION: nucleotide sequence comprising the 5' region
      flanking the foreign DNA in EE-GM1
<220> FEATURE:
<221> NAME/KEY: misc_feature
<222> LOCATION: (1)..(209)
<223> OTHER INFORMATION: plant DNA
<220> FEATURE:
<221> NAME/KEY: misc_feature
<222> LOCATION: (210)..(720)
<223> OTHER INFORMATION: foreign DNA

<400> SEQUENCE: 12

```
gagaagaaaa aggaaggcat aagagaccc tcctggcaca accctagaca ctctaagatc     60 cttttttcaaa cctgctccca ccatttcgag tcaagagata gataaataga cacatctcat  120
tgcaccgatc gggggcgttc gtagtgactg aggggtcaa agaccaagaa gtgagttatt    180
tatcagccaa gcattctatt cttcttatgt cggtgcgggc ctcttcgcta ttacgccagc   240
tggcgaaagg gggatgtgct gcaaggcgat taagttgggt aacgccaggg ttttcccagt   300
cacgacgttg taaaacgacg gccagtgaat tcccatggag tcaaagattc aaatagagga   360
cctaacagaa ctcgccgtaa agactggcga acagttcata cagagtctct tacgactcaa   420
tgacaagaag aaaatcttcg tcaacatggt ggagcacgac acgcttgtct actccaaaaa   480
tatcaaagat acagtctcag aagaccaaag ggcaattgag acttttcaac aaagggtaat   540
atccggaaac ctcctcggat tccattgccc agctatctgt cactttattg tgaagatagt   600
ggaaaaggaa ggtggctcct acaaatgcca tcattgcgat aaaggaaagg ccatcgttga   660
agatgcctct gccgacagtg gtcccaaaga tggacccccca cccacgagga gcatcgtgga  720
```

<210> SEQ ID NO 13
<211> LENGTH: 1000
<212> TYPE: DNA
<213> ORGANISM: Artificial
<220> FEATURE:
<223> OTHER INFORMATION: nucleotide sequence comprising the 3' region
      flanking the foreign DNA in EE-GM1
<220> FEATURE:
<221> NAME/KEY: misc_feature
<222> LOCATION: (1)..(568)
<223> OTHER INFORMATION: foreign DNA
<220> FEATURE:
<221> NAME/KEY: misc_feature
<222> LOCATION: (569)..(1000)
<223> OTHER INFORMATION: plant DNA

<400> SEQUENCE: 13

```
ttcggtgtag gtcgttcgct ccaagctggg ctgtgtgcac gaaccccccg ttcagcccga    60
ccgctgcgcc ttatccggta actatcgtct gagtccaac ccggtaagac acgacttatc    120
gccactggca gcagccactg gtaacaggat tagcagagcg aggtatgtag gcggtgctac   180
agagttcttg aagtggtggc ctaactacgg ctacactaga agaacagtat tggtatctg    240 cgctctgcta aagccagtta ccttcggaaa aagagttggt agctcttgat ccggcaaaca   300
aaccaccgct ggtagcggtg gtttttttgt ttgcaagcag cagattacgc gcagaaaaaa   360
```

```
aggatctcaa gaagatcctt tgatctttc tacggggtct gacgctcagt ggaacgaaaa      420
ctcacgttaa gggatttgg tcatgagatt atcaaaaagg atcttcacct agatccttt      480 aaattaaaaa tgaagtttta aatcaatcta agtatatat gagtaaactt ggtctgacag      540
ttaccaatgc ttaatcagtg aggcacctt aatctagatg atctgtctca actttaccaa      600 aagtttgag cacatgtttg gattcacctt aaataatcta aaatcacagc ttgtttgatc      660
ccaaaggagt taattctaag taaaattgat tgagttaaaa caattgtgtt agatagagaa      720
attttctttg aataaaaaca tctagacaca aatcatttca cttcaaaata attttaaaca      780
aaataaattt tgcaattcat tcatccaaac aaacatttga attaactata atcaattcaa      840
attgttacag tgtgttgcat tcatatcatt cctaataagt ctacattaaa gattaagagt      900
gagaatgaga ggaagagaga acggtttcag ggttaaccct ttgtttggaa gaaccatcaa      960
acagtggcaa cggatcatcc ttgctgcaaa acatagcttt                           1000
```

<210> SEQ ID NO 14
<211> LENGTH: 810
<212> TYPE: DNA
<213> ORGANISM: Artificial
<220> FEATURE:
<223> OTHER INFORMATION: nucleotide sequence comprising the 5' region
      flanking the foreign DNA in EE-GM2
<220> FEATURE:
<221> NAME/KEY: misc_feature
<222> LOCATION: (1)..(311)
<223> OTHER INFORMATION: plant DNA
<220> FEATURE:
<221> NAME/KEY: misc_feature
<222> LOCATION: (312)..(810)
<223> OTHER INFORMATION: foreign DNA

<400> SEQUENCE: 14

```
gtcatcgtcg tcgcgctgga gttcttgtgg tgccgctggt cgcactggag tttgggtgtt       60
gttgttcatg cttgcgctgc taatcccctt ttgtatgcga aaatcgggtt tgggtcgggt      120
cgggtcagcc caacacgacc taatttgtgt tacgaaaatt tcaacaaaaa aaaaaagtta      180
tcttccgcca ttatcgccat tccgccacga tcattaaggc tatggcggcc gcaatggcgc      240
cgccatatga aacccgcaat gccatcgcta tttggtggca ttttccaaa acccgcaat      300 gtcataccgt catcgttgtc agaagtaagt tggccgcagt gttatcactc atggttatgg      360
cagcactgca taattctctt actgtcatgc catccgtaag atgcttttct gtgactggtg      420
agtactcaac caagtcattc tgagaatagt gtatgcggcg accgagttgc tcttgcccgg      480
cgtcaatacg ggataatacc gcgccacata gcagaacttt aaaagtgctc atcattggaa      540
aacgttcttc ggggcgaaaa ctctcaagga tcttaccgct gttgagatcc agttcgatgt      600
aacccactcg tgcacccaac tgatcttcag catcttttac tttcaccagc gtttctgggt      660
gagcaaaaac aggaaggcaa aatgccgcaa aaaagggaat aacgccaggg ttttcccagt      720
cacgacgttg taaaacgacg gccagtgaat tcccatggag tcaaagattc aaatagagga      780
cctaacagaa ctcgccgtaa agactggcga                                       810
```

<210> SEQ ID NO 15
<211> LENGTH: 1880
<212> TYPE: DNA
<213> ORGANISM: Artificial
<220> FEATURE:
<223> OTHER INFORMATION: nucleotide sequence comprising the 3' region
      flanking the foreign DNA in EE-GM2
<220> FEATURE:

<221> NAME/KEY: misc_feature
<222> LOCATION: (1)..(507)
<223> OTHER INFORMATION: foreign DNA
<220> FEATURE:
<221> NAME/KEY: misc_feature
<222> LOCATION: (508)..(1880)
<223> OTHER INFORMATION: plant DNA

<400> SEQUENCE: 15

```
cttttaaatt aaaaatgaag ttttaaatca atctaaagta tatatgagta aacttggtct    60
gacagttacc aatgcttaat cagtgaggca cctatctcag cgatctgtct atttcgttca   120
tccatagttg cctgactccc cgtcgtgtag ataactacga tacggagggg cttaccatct   180
ggccccagtg ctgcaatgat accgcgagac ccacgctcac cggctccaga tttatcagca   240
ataaaccagc cagccggaag ggccgagcgc agaagtggtc ctgcaacttt atccgcctcc   300
atccagtcta ttaattgttg ccgggaagct agagtaagta gttcgccagt taatagtttg   360
cgcaacgttg ttgccattgc tacaggcatc gtggtgtcac gctcgtcgtt tggtatggct   420
tcattcagct ccggttccca acgatcaagg cgagttacat gatcccccat gttgtgcaaa   480
aaagcggtta gctccttcgg tcctccgatg gcaccgccat aaccacaatt taacaacttt   540
ataaatgact tagtatatta gcaatttatc ttgtcacatg cacatatttt ataactataa   600
taggagtttg agtttaaatg atgtaatgaa ttttggattg catgttgttt tgtactatat   660
tggtagcttt ttccaatgaa gtgttaaatt tgtattttc atattcaggg tcacgtttga   720
ccttctctag tcactgccct aattaagccc tttctcttgc actcttgatg cttacttaac   780
ctgggcatca ggcatatgta atgttatcaa tcaaactatc acgtttcatg catttattaa   840
tcttcattga tgcccttgtc tcgctcttgc ccctttttcc aatttatgct tcaaatcttt   900
gacatgttcc atgtccttat tccttttctc tgtaactgtt cattttcgtt atgaaccatg   960
aagataaact actattgtta aagtctcggt tcaaatttaa cttttctgct tttccccata  1020
taattgaata agacttggtc gtggttgttc tcattgcata tacctttatt atatgcatag  1080
aagtgatttt tttgcctaac ttgtacattt ttttatggca gtgatganga tgtagagagg  1140
cttatcgagc ttgtgaaggg aatttcttgc aagattaatc taatctcatt caatccgcac  1200
agtggatcat tcttcaaacc aaccaaatat gaaaggatga ttgaattccg aaatacattg  1260
gctggggcag gattgatagt attttttaaga cttagtagag gtgatgatca attggcttcc  1320
tgtggtcaat tgggtaagcc tggcaccatt caagctccat ttcttcgtgt accagagcaa  1380
ttccaaatgg caattggaag ttcaacttga ttctttgtgg aggttctgtg gcaaattgat  1440
cttacagtta ttaacgaaga attatatagg acacttgtgg tgggggtagc tagggatgac  1500
ttcatactga caatgcaaga ccaagagcta aattagggg atgtctgtct gttttcatat   1560
tgtactttc cattttacag ttaattgata tatttttttt tattaatgtg acggatccag   1620
attacttact ggctaagaaa taagaaataa aaatgattta aatatatttt tagtcgaagt   1680
ctgtattttt tagtttccca aattaaaatt tgcatttttt aatctctcat ttataaaatg   1740
cctttttaag ttcttcttag ctgattttg gcaacttgga tgcacaatgt gcaactatcg   1800
taacaatatt tttcttgaaa tttaaagaga ctaaatata tgttttacca taacactcat   1860
gttagtaaaa ccattatttg                                              1880
```

<210> SEQ ID NO 16
<211> LENGTH: 20
<212> TYPE: DNA
<213> ORGANISM: Artificial

```
<220> FEATURE:
<223> OTHER INFORMATION: primer SOY06

<400> SEQUENCE: 16
ggcgttcgta gtgactgagg                                           20

<210> SEQ ID NO 17
<211> LENGTH: 21
<212> TYPE: DNA
<213> ORGANISM: Artificial
<220> FEATURE:
<223> OTHER INFORMATION: primer SOY 07

<400> SEQUENCE: 17
gttttacaac gtcgtgactg g                                         21

<210> SEQ ID NO 18
<211> LENGTH: 21
<212> TYPE: DNA
<213> ORGANISM: Artificial
<220> FEATURE:
<223> OTHER INFORMATION: primer SOY 09

<400> SEQUENCE: 18
tgtggttatg gcggtgccat c                                         21

<210> SEQ ID NO 19
<211> LENGTH: 21
<212> TYPE: DNA
<213> ORGANISM: Artificial
<220> FEATURE:
<223> OTHER INFORMATION: SOY 010

<400> SEQUENCE: 19
tgctacaggc atcgtggtgt c                                         21

<210> SEQ ID NO 20
<211> LENGTH: 17806
<212> TYPE: DNA
<213> ORGANISM: Artificial
<220> FEATURE:
<223> OTHER INFORMATION: nucleotide sequence of a foreign DNA and
      flanking plant sequences in EE-GM3

<400> SEQUENCE: 20
gacttccatg tctagattca ttgtactaag atttcaaacg atatatatat atatatatat     60
atatatattc aattacatct tttcaaaaaa acatatatgc atcgtatttt ctaatacatt    120
tttttatata tgttattagt taaaatttat taaaaatcat aaaattaagt aagtttcaca    180
taacatccaa tgattttctc gtaattttaa gactggacta agaatatag tagtaacact     240 tctcttcaaa taatatactt tatttgcccg aggaatagca ttgccatatt gaactattag    300
gaaagctgaa catcaattgg tacacttgga tggttcccac ggtttattat tgtctacatc    360
tggtcatcca agcagaggtt atatcttcta aactcgaca atcttcgtt gtgcctatat      420 agagttgctt gtacgactaa aacgcttata ataatcgtta tacaatctat gattcacagt    480
tatgatacgt gtatgcaata aatgaataga tagataaata tgatacaatt atacaattat   540
tctaaaatat atagaataca atatatgtat gtataaaaaa ttcataaaac accaataagc    600
atataattgc aatttttgcaa aaccaaatta agaatataac tcaaatatta ctagaaacaa   660
aaaaaattat aaatcattgt cttcataaat taattctaag tatctacaaa tagaaataat    720 atgaattta tataaaaaag taatataaat tttattcctt tcttaaattt atgaaaaata    780
```

```
atacttctat atttctatac atgtttctat acatgcgttt caatgtctga tagtgatagg    840
aaactctact gtattttcaa aagtttttt ttgtttaaat atattttttg tcatgtaatt    900
gtgtgtgttt tcatttacgt ccatgtaaaa agaaatatt ttagttctat taaaatattt    960
tttttatttt ttatccttaa aatacttaa ataaatttt ttcctattta aagcattttt   1020
tataatttaa agcgctattt aaaacgtttt tagaataaaa acataaaaca aacacattt    1080
aaaatgattg aaatgaaaaa taaaactaat gaaaacgaaa acaatactaa attacaggaa   1140
agaaaaatat attcaaactt ttatgtttaa aggtttttga atatttctct gattcgtttg   1200
aaatatgtga agaaaattaa aatatcaagt agtaggttac aacagttcgg gtgcaacagt   1260
gactatgaca gcaagataat agggccaata tatttggata cctctcttaa gacgtaaaca   1320
ttttgagcga gaaataatg gaaaaaaaat aagtcattca aatgataata gatatataaa    1380
ttatttttta ttttaaatat cttattaata tttttatttt tttatcatat tataaattat   1440
attatattta tgtagctttg ctcattgtct tctacgggaa ctttcccgga cataggaacc   1500
gcccttcgt tatcctcatc catcgtgaaa tcaggaaata aatgttcgaa gatttgaggt    1560
caaaagtcga atttcatgtt gtctcttcta tttagataca aaattgaagc aatttcacc    1620
aatttaatgc caaaatttaa aacaacgctg tcctgatttc acgatggatg aggataacga   1680
aagggcggtt cctatgtccg ggaaagttcc cgtagaagac aatgagcaaa gctactgaaa   1740
cgcggacacg acgtcgcatt ggtacggata tgagttaaac cgactcaatt cctttattaa   1800
gacataaaacc gattttggtt aaagtgtaac agtgagctga tataaaaccg aaacaaaccg   1860
gtacaagttt gattgagcaa cttgatgaca aacttcagaa ttttggttat tgaatgaaaa   1920
tcatagtcta atcgtaaaaa atgtacagaa gaaaagctag agcagaacaa agattctata   1980
ttctggttcc aatttatcat cgctttaacg tccctcagat ttgatcgggc tgcaggaatt   2040
aaacgcccgg gcacgtggga tcctctagag tcgactctag cagatctggc cggcccaccg   2100
gtgggccata tgggcccgcg gccgcgaatt cgagctcggt acctacctgg cgaaaggggg   2160
atgtgctgca aggcgattaa gttgggtaac gccagggttt tcccagtcac gacgttgtaa   2220
aacgacggcc agtgaattgc ggccgcaatt cccgatctag taacatagat gacaccgcgc   2280
gcgataattt atcctagttt gcgcgctata ttttgttttc tatcgcgtat taaatgtata   2340
attgcgggac tctaatcata aaaacccatc tcataaataa cgtcatgcat tacatgttaa   2400
ttattacatg cttaacgtaa ttcaacagaa attatatgat aatcatcgca agaccggcaa   2460
caggattcaa tcttaagaaa ctttattgcc aaatgtttga acgatcgggg aaattcgtcg   2520
agtcaccctc ggccgggctt tttgacgctt aatcggcggt caatacacca cgacgcacct   2580
ggtcacgttc gatggactcg aacagcgcct tgaagttcca ctcgccaaac ccatcgtcgc   2640
ccttgcgctg gatgaattcg aagaacaccg ggcccatcag ggtttccgag aagatctgca   2700
gcagcaggcg tttgtcgcct tccacggaag atccgtccag caggataccg cgtgcctgca   2760
gttgatccac cggctcgccg tggtcaggca ggcggccttc gagcatttcg taataagtgt   2820
ctggcggcgc ggtcatgaag cgcatgccga ttttcttcaa cgcgtcccag gtcttgacca   2880
ggtcgtcggt gaggaacgcc acgtgctgga tgccttcgcc gttgaactgc atcaggaact   2940
cttcgatctg ccccgcgccc ttggacgact cttcgttcag cgggatgcgg atcatgccgt   3000
ccggcgcact catggccttg gaagtcaggc cggtgtactc gcccttgata tcgaagtaac   3060
gcgcttcacg gaagttgaac aatttctcgt agaagttggc ccagtagacc atgcggccgc   3120
```

```
gatagacgtt gtgggtcagg tggtcgatga ctttgagacc tgcaccgacc ggattgcgct    3180
ccacaccttc gaggtacacg aagtcgatgt cgtagatcga gctgccttcg ccgaaacggt    3240
cgatcaggta caacggcgcg ccgccgatgc ccttgatcgc cggcaggttc aattccatcg    3300
gcccggtgtc aatatggatc ggctgggcgc cgagttccag ggcgcggttg taggccttt     3360
gcgagtcctt cacgcggaac gccatgccgc acaccgacgg gccgtgttcg gccgcaaagt    3420
aggaggcgat gctgttgggc tcgttgttga ggatcaggtt gatctcgccc tggcggtaca    3480
ggtgcacgtt cttggaacgg tgggtcgcga ctttggtgaa gcccatgatc tcgaagatcg    3540
gctccagggt acccgcgtc ggcgacgcga attcgatgaa ttcaaagccc atcaggccca     3600
ttgggttttc gtatagatct gccatgcacc ggatccttcc gccgttgctg acgttgccga    3660
ggcttctgga ggagcggcgg gcgacgggga ggctggcggt ggacttgagc ccctggaacg    3720
gagcgacggc ggtggccgac gaggccatca tcacggtggg cgccatagac agcggcggca    3780
ggtacgacag cgtctcgaac ttcttgttgc cgtaggccgg ccacacctgc atatattgaa    3840
ctcttccacc gttgctggga agggtggaga agtcgttagc cttcttggtg gtggggaagg    3900
cggcgttgga cttaaggccg gtgaacggag ccaccatgtt ggcctgagca ggggcggtcc    3960
ggctaacggt cgcgactgag gaggagatcg aagccatggc tatcgttcgt aaatggtgaa    4020
aattttcaga aaattgcttt tgcttttaaaa gaaatgattt aaattgctgc aatagaagta    4080
gaatgcttga ttgcttgaga ttcgtttgtt ttgtatatgt tgtgttgaga attctagagt    4140
cgagagaaat tgatgtctgt agaagaagaa gaacggttaa gagtagattt gggtgagaaa    4200
gatgtgaaat tgttttttata ggcaaagacg gagagtctat tttttgagca atcagatcgc    4260
atattaaatc taacggctga gatatcgatc cgtgtgtaca ataaaatgat gtataaaccg    4320
tcgatctgtt ttaatcgacg gttcatatta gtgatccgcg tgatggcagt gatagccact    4380
aagaatcgtc ttttgttta catgtggcgc cacaaattag ggtaatgaag cggcaatatt    4440
ttggaactcg gaaataaaa ttgcgccatc acattatttg aaaattttca catgctttta     4500
ttttaaaaac ccacgaatta caagttacaa ccgaaaaaga tttataatat agtgatttat    4560
actaattttg tagtagctta atgtatattg atactggaaa aacaatgaca atcataatcg    4620
atccgtgtgt acaataaaat gatgtataaa ccgtcgatct gttttaatcg acggttcata    4680
ttagtgatcc gcgtgatggc agtgatagcc actaagaatc gtcttttgtt ttacatgtgg    4740
cgccacaaat tagggtaatg aagcggcaat attttggaac tcggaaaata aaattgcgcc    4800
atcacattat ttgaaaattt tcacatgctt ttattttaaa acccacgaa ttacaagtta     4860
caaccgaaaa agatttataa tatagtgatt tatactaatt ttgtagtagc ttaatgtata    4920
ttgatactgg aaaaacaatg acaatcatat gttagtatta tcaagttatc gtattggatat   4980
tgatattgga acatacaatg ggtattgcct tctttcgacc ataaatatca ccaaatttac    5040
aaagtttgtg tataccaagt tatcaattgt aaatgggatg tcaacatttt aatttcccttt   5100
tgagaaacta tagaccacaa gaacacactt caatagataa agtaactatt tacataagag    5160
gttttaaaat cacattaaca aaataatta ccaaccggca ctcacaaata caaacagagc     5220
acacgacatg tcaaagccac aagtaaattc gttgagtggt ggtttcatta caattgtgtc    5280
acttgcagca caaactatct tgctctggga atcatctcag catcaaagat catgctcact    5340
tcaggggaac ttagtgtatc catgcctcga ctcatatttc tcctcgacct gcaggcatgc    5400
aagctctaga gcggccgcca ccgcggtgga ggtactcgag tcgcgacgta cgttcgaaca    5460
attggtttta aaagcttgca tgcctgcagg tcgaggagaa atatgagtcg aggcatggat    5520
```

```
acactaagtt cccctgaagt gagcatgatc tttgatgctg agatgattcc cagagcaaga    5580
tagtttgtgc tgcaagtgac acaattgtaa tgaaaccacc actcaacgaa tttacttgtg    5640
gctttgacat gtcgtgtgct ctgtttgtat ttgtgagtgc cggttggtaa ttatttttgt    5700
taatgtgatt ttaaaacctc ttatgtaaat agttacttta tctattgaag tgtgttcttg    5760
tggtctatag tttctcaaag ggaaattaaa atgttgacat cccatttaca attgataact    5820
tggtatacac aaactttgta aatttggtga tatttatggt cgaaagaagg caatacccat    5880
tgtatgttcc aatatcaata tcaatacgat aacttgataa tactaacata tgattgtcat    5940 tgttttttcca gtatcaatat acattaagct actacaaaat tagtataaat cactatatta    6000
taaatctttt tcggttgtaa cttgtaattc gtgggttttt aaaataaaag catgtgaaaa    6060
ttttcaaata atgtgatggc gcaatttat tttccgagtt ccaaaatatt gccgcttcat     6120
taccctaatt tgtggcgcca catgtaaaac aaaagacgat tcttagtggc tatcactgcc    6180
atcacgcgga tcactaatat gaaccgtcga ttaaaacaga tcgacggttt atacatcatt    6240
ttattgtaca cacggatcga tatctcagcc gttagattta atatgcgatc tgattgctca    6300
aaaaatagac tctccgtctt tgcctataaa aacaatttca catctttctc acccaaatct    6360
actcttaacc gttcttcttc ttctacagac atcaatttct ctcgactcta gaggatccaa    6420
gcttatcgat ttcgaccccc tcaggcgaag aacaggtatg atttgtttgt aattagatca    6480
ggggtttagg tctttccatt actttttaat gttttttctg ttactgtctc cgcgatctga    6540
ttttacgaca atagagtttc gggttttgtc ccattccagt ttgaaaataa aggtccgtct    6600
tttaagtttg ctggatcgat aaacctgtga agattgagtc tagtcgattt attggatgat    6660
ccattcttca tcgtttttttt cttgcttcga agttctgtat aaccagattt gtctgtgtgc    6720
gattgtcatt acctagccgt gtatcgagaa ctagggtttt cgagtcaatt ttgccccttt    6780
tggttatatc tggttcgata acgattcatc tggattaggg ttttaagtgg tgacgtttag    6840
tattccaatt tcttcaaaat ttagttatgg ataatgaaaa tccccaattg actgttcaat    6900
ttcttgttaa atgcgcagat ccccatggct tcgatctcct cctcagtcgc gaccgttagc    6960
cggaccgccc ctgctcaggc caacatggtg gctccgttca ccggccttaa gtccaacgcc    7020
gccttcccca ccaccaagaa ggctaacgac ttctccaccc ttcccagcaa cggtggaaga    7080
gttcaatgta tgcaggtgtg gccggcctac ggcaacaaga agttcgagac gctgtcgtac    7140
ctgccgccgc tgtctatggc gcccaccgtg atgatggcct cgtcggccac cgccgtcgct    7200
ccgttccagg ggctcaagtc caccgccagc ctccccgtcg cccgccgctc ctccagaagc    7260
ctcggcaacg tcagcaacgg cggaaggatc cggtgcatgg ccggcgccga ggagatcgtg    7320
ctgcagccca tcaaggagat ctccggcacc gtcaagctgc cggggtccaa gtcgctttcc    7380
aaccggatcc tcctactcgc cgccctgtcc gagggacaa cagtggttga taacctgctg     7440
aacagtgagg atgtccacta catgctcggg gccttgagga ctcttggtct ctctgtcgaa    7500
gcggacaaag ctgccaaaag agctgtagtt gttggctgtg gtggaaagtt cccagttgag    7560
gatgctaaag aggaagtgca gctcttcttg gggaatgctg gaatcgcaat gcggtccttg    7620
acagcagctg ttactgctgc tggtggaaat gcaacttacg tgcttgatgg agtaccaaga    7680
atgagggaga gacccattgg cgacttggtt gtcggattga agcagcttgg tgcagatgtt    7740
gattgtttcc ttggcactga ctgcccacct gttcgtgtca atggaatcgg aggctaccct    7800
ggtggcaagg tcaagctgtc tggctccatc agcagtcagt acttgagtgc cttgctgatg    7860
```

```
gctgctcctt tggctcttgg ggatgtggag attgaaatca ttgataaatt aatctccatt    7920
ccgtacgtcg aaatgacatt gagattgatg gagcgttttg gtgtgaaagc agagcattct    7980
gatagctggg acagattcta cattaaggga ggtcaaaaat acaagtcccc taaaaatgcc    8040
tatgttgaag gtgatgcctc aagcgcaagc tatttcttgg ctggtgctgc aattactgga    8100
gggactgtga ctgtggaagg ttgtggcacc accagtttgc agggtgatgt gaagtttgct    8160
gaggtactgg agatgatggg agcgaaggtt acatggaccg agactagcgt aactgttact    8220
ggcccaccgc gggagccatt tgggaggaaa cacctcaagg cgattgatgt caacatgaac    8280
aagatgcctg atgtcgccat gactcttgct gtggttgccc tctttgccga tggcccgaca    8340
gccatcagag acgtggcttc ctggagagta aaggagaccg agaggatggt tgcgatccgg    8400
acggagctaa ccaagctggg agcatctgtt gaggaagggc cggactactg catcatcacg    8460
ccgccggaga agctgaacgt gacggcgatc gacacgtacg acgaccacag gatggcgatg    8520
gctttctccc ttgccgcctg tgccgaggtc ccgtcacca tccggacccc tgggtgcacc    8580
cggaagacct tcccccgacta cttcgatgtg ctgagcactt tcgtcaagaa ttaagctcta    8640
gaactagtgg atcccccgat ccgcgtttgt gttttctggg tttctcactt aagcgtctgc    8700
gttttacttt tgtattgggt ttggcgttta gtagtttgcg gtagcgttct tgttatgtgt    8760
aattacgctt tttcttcttg cttcagcagt ttcggttgaa atataaatcg aatcaagttt    8820
cactttatca gcgttgtttt aaattttggc attaaattgg tgaaaattgc ttcaattttg    8880
tatctaaata gaagagacaa catgaaattc gacttttgac ctcaaatctt cgaacattta    8940
tttcctgatt tcacgatgga tgaggataac gaaagggcgg ttcctatgtc cgggaaagtt    9000
cccgtagaag acaatgagca agctactga aacgcggaca cgacgtcgca ttggtacgga    9060
tatgagttaa accgactcaa ttcctttatt aagacataaa ccgattttgg ttaaagtgta    9120
acagtgagct gatataaaac cgaaacaaac cggtacaagt ttgattgagc aacttgatga    9180
caaacttcag aattttggtt attgaatgaa atcatagtc taatcgtaaa aaatgtacag    9240
aagaaaagct agagcagaac aaagattcta tattctggtt ccaatttatc atcgctttaa    9300
cgtccctcag atttgatcgg gctgcaggaa ttaaacgccc gggcacgtgg gatcctctag    9360
cagatctggc cggcccaccg gtgggccata tgggcccgcg gccgcgaatt cgagctcggt    9420
acctacctgg cgaagggggg atgtgctgca aggcgattaa gttgggtaac gccagggttt    9480
tcccagtcac gacgttgtaa aacgacggcc agtgaattgc ggccgcaatt cccgatctag    9540
taacatagat gacaccgcgc gcgataattt atcctagttt gcgcgctata ttttgttttc    9600
tatcgcgtat taaatgtata attgcgggac tctaatcata aaaacccatc tcataaataa    9660
cgtcatgcat tacatgttaa ttattacatg cttaacgtaa ttcaacagaa attatatgat    9720
aatcatcgca agaccggcaa caggattcaa tcttaagaaa ctttattgcc aaatgtttga    9780
acgatcgggg aaattcgtcg agtcaccctc ggccgggctt tttgacgctt aatcggcggt    9840
caatacacca cgacgcacct ggtcacgttc gatggactcg aacagcgcct tgaagttcca    9900
ctcgccaaac ccatcgtcgc ccttgcgctg gatgaattcg aagaacaccg ggcccatcag    9960
ggtttccgag aagatctgca gcagcaggcg tttgtcgcct tccacggaag atccgtccag   10020
caggataccg cgtgcctgca gttgatccac cggctcgccg tggtcaggca ggcggccttc   10080
gagcatttcg taataagtgt ctggcggcgc ggtcatgaag cgcatgccga tttcttcaa   10140
cgcgtcccag gtcttgacca ggtcgtcggt gaggaacgcc acgtgctgga tgccttcgcc   10200
gttgaactgc atcaggaact cttcgatctg ccccgcgccc ttggacgact cttcgttcag   10260
```

-continued

```
cgggatgcgg atcatgccgt ccggcgcact catggccttg gaagtcaggc cggtgtactc   10320
gcccttgata tcgaagtaac gcgcttcacg gaagttgaac aatttctcgt agaagttggc   10380
ccagtagacc atgcggccgc gatagacgtt gtgggtcagg tggtcgatga ctttgagacc   10440
tgcaccgacc ggattgcgct ccacaccttc gaggtacacg aagtcgatgt cgtagatcga   10500
gctgccttcg ccgaaacggt cgatcaggta caacggcgcg ccgccgatgc ccttgatcgc   10560
cggcaggttc aattccatcg gcccggtgtc aatatggatc ggctgggcgc cgagttccag   10620
ggcgcggttg taggccttt gcgagtcctt cacgcggaac gccatgccgc acaccgacgg   10680
gccgtgttcg gccgcaaagt aggaggcgat gctgttgggc tcgttgttga ggatcaggtt   10740
gatctcgccc tggcggtaca ggtgcacgtt cttggaacgg tgggtcgcga ctttggtgaa   10800
gcccatgatc tcgaagatcg gctccagggt accggcgtc ggcgacgcga attcgatgaa   10860
ttcaaagccc atcaggccca ttgggttttc gtatagatct gccatgcacc ggatccttcc   10920
gccgttgctg acgttgccga ggcttctgga ggagcgcgg gcgacgggga ggctggcggt   10980
ggacttgagc ccctggaacg gagcgacggc ggtggccgac gaggccatca tcacggtggg   11040
cgccatagac agcggcggca ggtacgacag cgtctcgaac ttcttgttgc cgtaggccgg   11100
ccacacctgc atatattgaa ctcttccacc gttgctggga agggtggaga agtcgttagc   11160
cttcttggtg gtggggaagg cggcgttgga cttaaggccg gtgaacggag ccaccatgtt   11220
ggcctgagca ggggcggtcc ggctaacggt cgcgactgag gaggagatcg aagccatggc   11280
tatcgttcgt aaatggtgaa aattttcaga aaattgcttt tgctttaaaa gaaatgattt   11340
aaattgctgc aatagaagta gaatgcttga ttgcttgaga ttcgtttgtt ttgtatatgt   11400
tgtgttgaga attctagagt cgagagaaat tgatgtctgt agaagaagaa gaacggttaa   11460
gagtagattt gggtgagaaa gatgtgaaat tgttttata ggcaaagacg gagagtctat   11520
tttttgagca atcagatcgc atattaaatc taacggctga gatatcgatc cgtgtgtaca   11580
ataaaatgat gtataaaccg tcgatctgtt ttaatcgacg gttcatatta gtgatccgcg   11640
tgatggcagt gatagccact aagaatcgtc ttttgtttta catgtggcgc cacaaattag   11700
ggtaatgaag cggcaatatt ttggaactcg gaaaataaaa ttgcgccatc acattatttg   11760
aaaattttca catgctttta ttttaaaaac ccacgaatta caagttacaa ccgaaaaaga   11820
tttataatat agtgatttat actaattttg tagtagctta atgtatattg atactggaaa   11880
aacaatgaca atcataatcg atccgtgtgt acaataaaat gatgtataaa ccgtcgatct   11940
gttttaatcg acggttcata ttagtgatcc gcgtgatggc agtgatagcc actaagaatc   12000
gtcttttgtt ttacatgtgg cgccacaaat tagggtaatg aagcggcaat attttggaac   12060
tcggaaaata aaattgcgcc atcacattat ttgaaaattt tcacatgctt ttatttaaa   12120 aacccacgaa ttacaagtta caaccgaaaa agatttataa tatagtgatt tatactaatt   12180
ttgtagtagc ttaatgtata ttgatactgg aaaaacaatg acaatcatat gttagtatta   12240
tcaagttatc gtattgatat tgatattgga acatacaatg ggtattgcct tctttcgacc   12300
ataaatatca ccaaatttac aaagtttgtg tataccaagt tatcaattgt aaatgggatg   12360
tcaacatttt aatttccctt tgagaaacta tagaccacaa gaacacactt caatagataa   12420
agtaactatt tacataagag gttttaaaat cacattaaca aaaataatta ccaaccggca   12480
ctcacaaata caaacagagc acacgacatg tcaaagccac aagtaaattc gttgagtggt   12540
ggtttcatta caattgtgtc acttgcagca caaactatct tgctctggga atcatctcag   12600
```

```
catcaaagat catgctcact tcagggaac  ttagtgtatc catgcctcga ctcatatttc   12660
tcctcgacct gcaggcatgc aagctctaga gcggccgcca ccgcggtgga ggtactcgag   12720
tcgcgacgta cgttcgaaca attggtttta aaagcttgca tgcctgcagg tcgaggagaa   12780
atatgagtcg aggcatggat acactaagtt cccctgaagt gagcatgatc tttgatgctg   12840
agatgattcc cagagcaaga tagtttgtgc tgcaagtgac acaattgtaa tgaaaccacc   12900
actcaacgaa tttacttgtg gctttgacat gtcgtgtgct ctgttttgtat ttgtgagtgc   12960 cggttggtaa ttattttttgt taatgtgatt ttaaaacctc ttatgtaaat agttacttta   13020
tctattgaag tgtgttcttg tggtctatag tttctcaaag ggaaattaaa atgttgacat   13080
cccatttaca attgataact tggtatacac aaactttgta aatttggtga tatttatggt   13140
cgaaagaagg caatacccat tgtatgttcc aatatcaata tcaatacgat aacttgataa   13200
tactaacata tgattgtcat tgtttttcca gtatcaatat acattaagct actacaaaat   13260
tagtataaat cactatatta taaatctttt tcggttgtaa cttgtaattc gtgggtttt    13320 aaaataaaag catgtgaaaa ttttcaaata atgtgatggc gcaattttat tttccgagtt   13380
ccaaaatatt gccgcttcat taccctaatt tgtggcgcca catgtaaaac aaaagacgat   13440
tcttagtggc tatcactgcc atcacgcgga tcactaatat gaaccgtcga ttaaaacaga   13500
tcgacggttt atacatcatt ttattgtaca cacggatcga tatctcagcc gttagattta   13560
atatgcgatc tgattgctca aaaaatagac tctccgtctt tgcctataaa aacaatttca   13620
catctttctc acccaaatct actcttaacc gttcttcttc ttctacagac atcaatttct   13680
ctcgactcta gaggatccaa gcttatcgat ttcgaacccc tcaggcgaag aacaggtatg   13740
atttgtttgt aattagatca ggggtttagg tcttcccatt actttttaat gttttttctg   13800
ttactgtctc cgcgatctga ttttacgaca atagagtttc gggttttgtc ccattccagt   13860
ttgaaaataa aggtccgtct tttaagtttg ctggatcgat aaacctgtga agattgagtc   13920
tagtcgattt attggatgat ccattcttca tcgtttttttt cttgcttcga agttctgtat   13980
aaccagattt gtctgtgtgc gattgtcatt acctagccgt gtatcgagaa ctagggtttt   14040
cgagtcaatt ttgcccctttt tggttatatc tggttcgata acgattcatc tggattaggg   14100 tttttaagtgg tgacgtttag tattccaatt tcttcaaaat ttagttatgg ataatgaaaa   14160 tcccaattg actgttcaat ttcttgttaa atgcgcagat ccccatggct tcgatctcct   14220
cctcagtcgc gaccgttagc cggaccgccc ctgctcaggc caacatggtg gctccgttca   14280
ccggccttaa gtccaacgcc gccttcccca ccaccaagaa ggctaacgac ttctccaccc   14340
ttcccagcaa cggtggaaga gttcaatgta tgcaggtgtg gccggcctac ggcaacaaga   14400
agttcgagac gctgtcgtac ctgccgccgc tgtctatggc gcccaccgtg atgatggcct   14460
cgtcggccac cgccgtcgct ccgttccagg ggctcaagtc caccgccagc ctccccgtcg   14520
cccgccgctc ctccagaagc ctcggcaacg tcagcaacgg cggaaggatc cggtgcatgg   14580
ccggcgccga ggagatcgtg ctgcagccca tcaaggagat ctccggcacc gtcaagctgc   14640
cggggtccaa gtcgctttcc aaccggatcc tcctactcgc cgccctgtcc gaggggacaa   14700
cagtggttga taacctgctg aacagtgagg atgtccacta catgctcggg gccttgagga   14760
ctcttggtct ctctgtcgaa gcggacaaag ctgccaaaag agctgtagtt gttggctgtg   14820
gtggaaagtt cccagttgag gatgctaaag aggaagtgca gctcttcttg gggaatgctg   14880
gaatcgcaat gcggtccttg acagcagctg ttactgctgc tggtgaaat gcaacttacg   14940 tgcttgatgg agtaccaaga atgagggaga gacccattgg cgacttggtt gtcggattga   15000
```

```
agcagcttgg tgcagatgtt gattgtttcc ttggcactga ctgcccacct gttcgtgtca   15060
atggaatcgg agggctacct ggtggcaagg tcaagctgtc tggctccatc agcagtcagt   15120
acttgagtgc cttgctgatg gctgctcctt tggctcttgg ggatgtggag attgaaatca   15180
ttgataaatt aatctccatt ccgtacgtcg aaatgacatt gagattgatg gagcgttttg   15240
gtgtgaaagc agagcattct gatagctggg acagattcta cattaaggga ggtcaaaaat   15300
acaagtcccc taaaaatgcc tatgttgaag gtgatgcctc aagcgcaagc tatttcttgg   15360
ctggtgctgc aattactgga gggactgtga ctgtggaagg ttgtggcacc accagtttgc   15420
agggtgatgt gaagtttgct gaggtactgg agatgatggg agcgaaggtt acatggaccg   15480
agactagcgt aactgttact ggcccaccgc gggagccatt tgggaggaaa cacctcaagg   15540
cgattgatgt caacatgaac aagatgcctg atgtcgccat gactcttgct gtggttgccc   15600
tctttgccga tggcccgaca gccatcagag acgtggcttc ctggagagta aggagaccg   15660 agaggatggt tgcgatccgg acggagctaa ccaagctggg agcatctgtt gaggaagggc   15720
cggactactg catcatcacg ccgccggaga agctgaacgt gacggcgatc gacacgtacg   15780
acgaccacag gatggcgatg gctttctccc ttgccgcctg tgccgaggtc cccgtcacca   15840
tccgggaccc tgggtgcacc cggaagacct cccccgacta cttcgatgtg ctgagcactt   15900
tcgtcaagaa ttaagctcta gaactagtgg atccccgat ccgcgtttgt gttttctggg   15960
tttctcactt aagcgtctgc gttttacttt tgtattgggt ttggcgttta gtagtttgcg   16020
gtagcgttct tgttatgtgt aattacgctt tttcttcttg cttcagcagt ttcggttgaa   16080
atataaatcg aatcaagttt cactttatca gcgttgtttt aaattttggc attaaattgg   16140
tgaaaattgc ttcaattttg tatctaaata gaagagacaa catgaaattc gacttttgac   16200
ctcaaatctt cgaacattta tttcctgatt tcacgatgga tgaggataac gaaagggcgg   16260
ttcctatgtc cgggaaagtt cccgtagaag acaatgagca aagctactga acgcgggaca   16320
cgacgtcgca ttggtacgga tatgagttaa accgactcaa ttcctttatt aagacataaa   16380
ccgattttgg ttaaagtgta acagtgagct gatataaaac cgaaacaaac cggtacaagt   16440
ttgattgagc aacttgatga caaacttcag aattttggtt attgaatgaa atcatagtc   16500 taatcgtaaa aaatgtacag aagaaaagct agagcagaac aaagattcta tattctggtt   16560
ccaatttatc atcgctttaa cgtccctcag atttgatcgg gctgcaggaa ttaatgtggt   16620
tcatccgtct ttttgttaat gcggtcatca atacgtgcct caaagattgc caaatagatt   16680
aatgtggttc atctccctat atgttttgct tgttggattt tgctatcaca tgtttattgc   16740
tccaaactaa ttataataaa atgactttca aatgattggt gttgacattc ttttcaaatt   16800
gttcgctgaa gaaagataa tctcgaggcc ttgatttgtt aatgctttca ttaataaata   16860
aataaaataa ctcttttccaa atttcaattc atgcttttat attgtgtggt tcatcctcat   16920
cttatgtcac tattatcatt tcatgtttga gactttactt ggccatattt gagaagacct   16980
tcttcattat aggcaatttt atctccacaa taatataaga gaatatcttg aattaataat   17040
tattgaggat atattatagg gttctatgtg gaactaaaga catggttacc ccattaagag   17100
agagtataga ggaattactt ttatttgcca cgaggcgacg cgacttgtat ttattttgga   17160
attgtacttt tgcgtgagca gtgtggctct atgttggggc ctccacttgt tggtgtttta   17220
tatatgtgaa aggaggatga gggtgatggt tcatttcttt gcattatttt tgttattcgc   17280
gcgaatgata tatgccctgt ttttgaagat tgatagggaa gtccatatat aggaattgaa   17340
```

-continued

```
gtgtcaaaag ggtgtgagta tgtgctatga taatcaccca attaatgtac atctggtgtg    17400
gtgtttgaat ttgtaggtca ttaattaata ttcctcttgg tgaagtttgg agttcttttg    17460
caattacaat tctgttttgt aagtgattat gatggacttt tagatgtttc tcaaacagta    17520
ggtgtaaaga aaaatgggcc ctggtatgaa aatttgtttt cactctttct cattcatatc    17580
tttaaaaaaa gaatgataat tttgtaataa aaataaaaaa atattaaata ttttctcaaa    17640
tcaaacaacc tttattttt atgccaacaa taattttgtt aaagatggag atttcaatta    17700
ttatataaga gttcattata gttgaaaatt gaatgaatgt atatgtttac gtttttgtc     17760 tcaagtgaaa ctaagatcaa atattcatat ctattgagct ggtctt                  17806
```

```
<210> SEQ ID NO 21
<211> LENGTH: 23
<212> TYPE: DNA
<213> ORGANISM: Artificial
<220> FEATURE:
<223> OTHER INFORMATION: primer SHA130

<400> SEQUENCE: 21
ctatattctg gttccaattt atc                                            23

<210> SEQ ID NO 22
<211> LENGTH: 20
<212> TYPE: DNA
<213> ORGANISM: Artificial
<220> FEATURE:
<223> OTHER INFORMATION: primer SMP178

<400> SEQUENCE: 22
tgaggcacgt attgatgacc                                                20
```

The invention claimed is:

1. A plant, cell, plant part, tissue, seed, or progeny thereof, which is (a) a soybean plant, cell, a plant part, tissue, seed, or progeny thereof, each comprising elite event EE-GM3 and elite event EE-GM1, reference seed comprising said elite event EE-GM3 having been deposited at the NCIMB under deposit number NCIMB 41659 and reference seed comprising said elite event EE-GM1 having being deposited at the NCIMB under deposit number NCIMB 41658, or reference seed comprising elite event EE-GM3 and elite event EE-GM1 in its genome having been deposited at the ATCC under deposit number PTA-11041; or (b) a soybean plant, plant part, seed, cell, or tissue thereof, each comprising elite event EE-GM3 and elite event EE-GM1, said soybean plant being obtained by crossing a soybean plant comprising elite event EE-GM3 obtainable by propagation of, breeding with, or propagation of and breeding with a soybean plant grown from the seed deposited at the NCIMB under deposit number NCIMB 41659 with a soybean plant comprising elite event EE-GM1 in its genome, obtainable by propagation of, breeding with, or propagation of and breeding with a soybean plant grown from the seed deposited at the NCIMB under deposit number NCIMB 41658, or said soybean plant being obtainable by propagation of, breeding with, or propagation of and breeding with a soybean plant grown from the seed deposited at the ATCC under accession number PTA-11041; or (c) a soybean seed comprising elite events EE-GM3 and EE-GM1, reference seed comprising elite event EE-GM3 having been deposited at the NCIMB under deposit number NCIMB 41659, reference seed comprising elite event EE-GM1 having been deposited at the NCIMB under deposit number NCIMB 41658, and reference seed comprising elite events EE-GM3 and EE-GM1 having been deposited at the ATCC under deposit number PTA-11041; or (d) a soybean plant, plant part, cell, or tissue, each comprising elite events EE-GM3 and EE-GM1, obtainable from the seed of (c); or (e) a soybean plant, or cells, part, seed or progeny thereof, each comprising elite events EE-GM3 and EE-GM1, wherein the inserted foreign DNA of elite event EE-GM3 is oriented as indicated in FIG. 1, and wherein said event has 5' and 3' flanking DNA and sequences in the foreign DNA contiguous therewith, wherein said 5' flanking DNA and the foreign DNA contiguous therewith comprises a nucleotide sequence of SEQ ID No: 2, and said 3' flanking DNA and the foreign DNA contiguous therewith comprises a nucleotide sequence of SEQ ID No: 3, said inserted foreign DNA of FIG. 1 being present in the soybean elite event EE-GM3 deposited under deposit number NCIMB 41659, and wherein the inserted foreign DNA of elite event EE-GM1 is oriented as indicated in FIG. 3, and wherein said event has 5' and 3' flanking DNA and sequences in the foreign DNA contiguous therewith, wherein said 5' flanking DNA and the foreign DNA contiguous therewith comprises a nucleotide sequence of SEQ ID No: 12, and said 3' flanking DNA and the foreign DNA contiguous therewith comprises a nucleotide sequence of SEQ ID No: 13, said inserted foreign DNA of FIG. 3 being present in the soybean elite event EE-GM2 deposited under deposit number NCIMB 41658, or (f) a soybean plant, plant cell, tissue, or seed, each comprising in their genome a nucleic acid molecule comprising a nucleotide sequence of SEQ ID No: 1 from nucleotide position 188 to nucleotide position 7252 or the complement thereof, and comprising in their genome a nucleic acid molecule comprising a nucleotide sequence of elite event EE-GM1 or the complement thereof, reference seed comprising elite event EE-GM1 having been deposited under deposit number NCIMB 41658, wherein said nucleotide sequence of elite event EE-GM1 comprises or is the foreign DNA sequence in SEQ ID No: 12 or 13, or the foreign DNA sequence in the plant genome between the sequence of SEQ ID No: 12 and that of SEQ ID No: 13.

2. The soybean plant, seed, cell, tissue, part or progeny of claim 1(a), the genomic DNA of which, when amplified with two primers comprising the nucleotide sequence of SEQ ID No: 4 and SEQ ID No: 5 respectively, yields a DNA fragment of about 263 bp and the genomic DNA of which, when amplified with two primers comprising the nucleotide sequence of SEQ ID No: 16 and SEQ ID No: 17 respectively, yields a DNA fragment of about 183 bp.

3. A method for producing a soybean plant or seed comprising elite events EE-GM3 and EE-GM1 comprising crossing a plant according to claim 1(a) with another soybean plant, and planting the seed comprising said elite events obtained from said cross.

4. A soybean plant, cell, plant part, seed, or progeny thereof, each comprising in its genome elite event EE-GM3, wherein said event comprises in order the following nucleotide sequences:

(a) the nucleotide sequence of SEQ ID No: 2 from nucleotide 1 to 1451;
(b) the nucleotide sequence of the complement of the nucleotide sequence of SEQ ID No: 1 from nucleotide 6760 to nucleotide 6958;
(c) the nucleotide sequence of SEQ ID No: 1 from nucleotide 6874 to nucleotide 7298;
(d) the nucleotide sequence of SEQ ID No: 1 from nucleotide 7 to nucleotide 7291;
(e) the nucleotide sequence of SEQ ID No: 1 from nucleotide 12 to nucleotide 7265;
(f) the nucleotide sequence of SEQ ID No: 3 from nucleotide 217 to nucleotide 240;
(g) the nucleotide sequence of SEQ ID No: 3 from nucleotide 241 to nucleotide 1408; and further comprising in its genome elite event EE-GM1, wherein said event comprises in order the following sequences:
(h) the nucleotide sequence of SEQ ID No: 12 from nucleotide 1 to 209;
(i) the nucleotide sequence of SEQ ID No: 11 from nucleotide 340 to nucleotide 3461;
(j) the nucleotide sequence of the complement of the nucleotide sequence of SEQ ID No: 11 from nucleotide 1 to nucleotide 336;
(k) the nucleotide sequence of the complement of the nucleotide sequence of SEQ ID No: 11 from nucleotide 3462 to nucleotide 4076;
(l) the nucleotide sequence of SEQ ID No: 11 from nucleotide 337 to nucleotide 3043;
(m) the nucleotide sequence of SEQ ID No: 13 from nucleotide 559 to nucleotide 568; and
(n) the nucleotide sequence of SEQ ID No: 13 from nucleotide 569 to nucleotide 1000.

5. A plant, cell, plant part, tissue, seed, or progeny thereof, which is (a) a soybean plant, cell, plant part, tissue, seed, or progeny thereof, each comprising elite event EE-GM3 and elite event EE-GM2 in its genome, reference seed comprising said elite event EE-GM3 having been deposited at the NCIMB under deposit number NCIMB 41659 and reference seed comprising said elite event EE-GM2 having been deposited at the NCIMB under deposit number NCIMB 41660, or reference seed comprising elite event EE-GM3 and elite event EE-GM2 in its genome having been deposited at the ATCC under deposit number PTA-11042; or (b) a soybean plant, plant part, tissue, seed or progeny thereof, each comprising elite event EE-GM3 and elite event EE-GM2 in its genome, said soybean plant being obtained by crossing a soybean plant comprising elite event EE-GM3 in its genome, obtainable by propagation of, breeding with, or propagation of and breeding with a soybean plant grown from the seed deposited at the NCIMB under deposit number NCIMB 41659 with a soybean plant comprising elite event EE-GM2 in its genome, obtainable by propagation of, breeding with, or propagation of and breeding with a soybean plant grown from the seed deposited at the NCIMB under deposit number NCIMB 41660, or said soybean plant being obtainable by propagation of, breeding with, or propagation of and breeding with a soybean plant grown from the seed deposited at the ATCC under accession number PTA-11042; or (c) a soybean seed comprising elite events EE-GM3 and EE-GM2, reference seed comprising elite event EE-GM3 having been deposited at the NCIMB under deposit number NCIMB 41659, reference seed comprising elite event EE-GM2 having been deposited at the NCIMB under deposit number NCIMB 41660, and reference seed comprising elite events EE-GM3 and EE-GM2 having been deposited at the ATCC under deposit number PTA-11042; or (d) a soybean plant, cell, plant part, tissue, or progeny therof, each comprising elite events EE-GM3 and EE-GM2, produced from the seed of (c); or (e) a soybean plant, cell, plant part, tissue, seed, or progeny thereof, each comprising elite events EE-GM3 and EE-GM1, wherein said events comprise a nucleic acid sequence of SEQ ID No: 2 from nucleotide 1431 to 1472 and a nucleic acid sequence of SEQ ID No: 3 from nucleotide 220 to 261, or the complement of said sequences, and also a nucleic acid sequence of SEQ ID No: 12 from nucleotide 199 to 220 and a nucleic acid sequence of SEQ ID No: 13 from nucleotide 558 to 579, or the complement of said sequences; or (f) a soybean plant, cell, plant part, tissue, seed, or progeny thereof, each comprising elite events EE-GM3 and EE-GM2, wherein said events comprise a nucleic acid sequence of SEQ ID No: 2 from nucleotide 1431 to 1472 and a nucleic acid sequence of SEQ ID No: 3 from nucleotide 220 to 261, or the complement of said sequences, and also a nucleic acid sequence of SEQ ID No: 14 from nucleotide 301 to 322 and a nucleic acid sequence of SEQ ID No: 15 from nucleotide 497 to 518, or the complement of said sequences; or (g) a soybean plant, cell, plant part, tissue, seed, or progeny therof, each comprising in their genome a nucleic acid molecule comprising a nucleotide sequence of SEQ ID No: 20 from nucleotide position 1452 to nucleotide position 16638 or the complement thereof, or a nucleotide sequence of SEQ ID No: 20 or the complement thereof, and comprising in their genome a nucleic acid molecule comprising a nucleotide sequence of elite events EE-GM1 or EE-GM2 or the complement thereof, reference seed comprising elite event EE-GM1 having been deposited under deposit number NCIMB 41658, and reference seed comprising elite event EE-GM2 having been deposited under deposit number NCIMB 41660, wherein said nucleotide sequence of elite events EE-GM1 or EE-GM2 comprises or is the foreign DNA sequence in SEQ ID No: 12 or 13, or the foreign DNA sequence in SEQ ID No: 14 or 15, respectively, or the foreign DNA sequence in the plant genome between the sequence of SEQ ID No: 12 and that of SEQ ID No: 13, or the foreign DNA sequence in the plant genome between the sequence of SEQ ID No: 14 and that of SEQ ID No: 15, respectively; or (h) a soybean plant, cell, plant part, tissue, seed, or progeny thereof, each comprising elite events EE-GM3 and EE-GM2 in its genome, wherein the inserted foreign DNA of elite event EE-GM3 is oriented as indicated in FIG. 1, and wherein said event has 5' and 3' flanking DNA and foreign DNA contiguous therewith, wherein said 5' flanking DNA and the foreign DNA contiguous therewith comprises a nucleotide sequence of SEQ ID No: 2, and said 3' flanking DNA and the foreign DNA contiguous therewith comprises a nucleotide sequence of SEQ ID No: 3, said inserted foreign DNA of FIG. 1 being present in the soybean elite event EE-GM3 deposited under deposit number NCIMB 41659, and wherein the inserted foreign DNA of elite event EE-GM2 is oriented as indicated in FIG. 4, and wherein said event has 5' and 3' flanking DNA and foreign DNA contiguous therewith, wherein said 5' flanking DNA and the foreign DNA contiguous therewith comprises a nucleotide sequence of SEQ ID No: 14 and said 3' flanking DNA and the foreign DNA contiguous therewith comprises a nucleotide sequence of SEQ ID No: 15, said inserted foreign DNA of FIG. 4 being present in the soybean elite event EE-GM2 deposited under deposit number NCIMB 41660, or (i) a soybean plant, cell, plant part, tissue, seed, or progeny thereof, each comprising in their genome a nucleic acid molecule comprising a nucleotide sequence of SEQ ID No: 1 from nucleotide position 188 to nucleotide position 7252 or the complement thereof, and comprising in their genome a nucleic acid molecule comprising a nucleotide sequence of elite event EE-GM2 or the complement thereof, reference seed comprising elite event EE-GM2 having been deposited under deposit number NCIMB 41660, wherein said nucleotide sequence of elite event EE-GM2 comprises or is the foreign DNA sequence in SEQ ID No: 14 or 15, or the foreign DNA sequence in the plant genome between the sequence of SEQ ID No: 14 and that of SEQ ID No: 15.

6. The soybean plant, cell, plant part, tissue, seed, or progeny of claim 5(a), the genomic DNA of which, when amplified with two primers comprising the nucleotide sequence of SEQ ID No: 4 and SEQ ID No: 5 respectively, yields a DNA fragment of about 263 bp and the genomic DNA of which, when amplified with two primers comprising the nucleotide sequence of SEQ ID No: 18 and SEQ ID No: 19 respectively, yields a DNA fragment of about 151 bp.

7. A method for producing a soybean plant or seed comprising elite events EE-GM3 and EE-GM2 said method comprising crossing a plant according to claim 5(a) with another soybean plant, and planting the seed comprising said elite events obtained from said cross.

8. A soybean plant, cell, plant part, seed, or progeny thereof, each comprising elite event EE-GM3, wherein said event comprises in order the following nucleotide sequences:
    (a) the nucleotide sequence of SEQ ID No: 2 from nucleotide 1 to 1451;
    (b) the nucleotide sequence of the complement of the nucleotide sequence of SEQ ID No: 1 from nucleotide 6760 to nucleotide 6958;
    (c) the nucleotide sequence of SEQ ID No: 1 from nucleotide 6874 to nucleotide 7298;
    (d) the nucleotide sequence of SEQ ID No: 1 from nucleotide 7 to nucleotide 7291;
    (e) the nucleotide sequence of SEQ ID No: 1 from nucleotide 12 to nucleotide 7265;
    (f) the nucleotide sequence of SEQ ID No: 3 from nucleotide 217 to nucleotide 240; and
    (g) the nucleotide sequence of SEQ ID No: 3 from nucleotide 241 to nucleotide 1408, and further comprising in its genome elite event EE-GM2, wherein said event comprises in order the following sequences:
    (h) the nucleotide sequence of SEQ ID No: 14 from nucleotide 1 to 311;
    (i) the nucleotide sequence of SEQ ID No: 11 from nucleotide 3458 to nucleotide 3848;
    (j) the nucleotide sequence of SEQ ID No: 11 from nucleotide 413 to nucleotide 3457;
    (k) the nucleotide sequence of SEQ ID No: 15 from nucleotide 508 to nucleotide 1880.

9. The soybean plant, cell, part, tissue, seed or progeny of claim 1(a).

10. The soybean plant, cell, plant part, tissue, seed, or progeny of claim 5(a).

11. The soybean plant, cell, plant part, tissue, seed, or progeny of claim 5(a), wherein said elite event EE-GM3 comprises a foreign DNA comprising a chimeric gene encoding the 4-hydroxyphenylpyruvate dioxygenase of Pseudomonas fluorescens strain A32 modified by the replacement of the amino acid Glycine 336 with a Tryptophane (HPPD PF W336 gene) and a chimeric gene encoding the 5-enolpyruvyl shikimate-3-phosphate synthase enzyme double mutant from Zea Mays (2mEPSPS gene), said elite event EE-GM3 also comprising nucleotides 1 to 1451 of SEQ ID No: 2 immediately upstream of and contiguous with said foreign DNA and nucleotides 241 to 1408 of SEQ ID No: 3 immediately downstream of and contiguous with said foreign DNA, and wherein said elite event EE-GM2 comprises a foreign DNA comprising a chimeric phosphinothricin acetyltransferase encoding gene, said elite event EE-GM2 also comprising nucleotides 1 to 311 of SEQ ID No: 14 immediately upstream of and contiguous with said foreign DNA and nucleotides 508 to 1880 of SEQ ID No: 15 immediately downstream of and contiguous with said foreign DNA.

12. The soybean plant, cell, plant part, tissue, seed, or progeny of claim 5(h).

13. The soybean seed of claim 5(c).

14. The soybean plant, cell, plant part, tissue, seed, or progeny of claim 5(d).

15. The soybean plant, cell, plant part, tissue, seed, or progeny of claim 5(e).

16. The soybean plant, cell, plant part, tissue, seed, or progeny of claim 5(f).

17. The soybean plant, cell, plant part, tissue, seed, or progeny of claim 5(g).

18. The soybean plant, cell, plant part, tissue, seed, or progeny of claim 5(i), comprising in their genome a nucleic acid molecule comprising a nucleotide sequence of SEQ ID No: 20 or SEQ ID No: 20 from nucleotide position 1452 to nucleotide position 16638 or the complement thereof.

19. A method for producing a soybean plant or seed comprising elite events EE-GM3 and EE-GM2 comprising crossing a plant according to claim 5(h) with another soybean plant, and planting the seed comprising elite events EE-GM3 and EE-GM2 obtained from said cross.

20. A method for producing a soybean plant or seed comprising elite events EE-GM3 and EE-GM2 comprising crossing a plant according to claim 5(f) with another soybean plant, and planting the seed comprising elite events EE-GM3 and EE-GM2 obtained from said cross.

21. A soybean product produced from seed comprising elite events EE-GM3 and EE-GM2 of any one of claim 5(a), 5(h) or 5(f), wherein said soybean product is or comprises soybean meal, ground seeds, flour, or flakes.

22. A soybean product produced from seed comprising elite events EE-GM3 and EE-GM2 of claim 6, wherein said soybean product is or comprises soybean meal, ground seeds, flour, or flakes.

23. A soybean product produced from seed comprising elite events EE-GM3 and EE-GM2 of claim 8, wherein said soybean product is or comprises soybean meal, ground seeds, flour, or flakes.

24. A soybean product produced from seed comprising elite events EE-GM3 and EE-GM2 of claim 18, wherein said soybean product is or comprises soybean meal, ground seeds, flour, or flakes.

25. A method for producing a soybean product, comprising obtaining soybean seed comprising elite event EE-GM3 and elite event EE-GM2 of claim 5(a), and producing such soybean product therefrom.

26. A method for producing a soybean product, comprising obtaining soybean seed comprising elite event EE-GM3 and elite event EE-GM2 of claim 5(h), and producing such soybean product therefrom.

27. A method for producing a soybean product, comprising obtaining soybean seed comprising elite event EE-GM3 and elite event EE-GM2 of claim 5(f), and producing such soybean product therefrom.

28. A method for controlling weeds in a field of soybean plants comprising elite events EE-GM3 and EE-GM2 of claim 5(a), comprising treating the field with an effective amount of an isoxaflutole-based and/or glyphosate-based and/or glufosinate-based herbicide, wherein such plants are tolerant to such herbicide(s).

29. A process for weed control, comprising treating a field in which seeds containing elite events EE-GM3 and EE-GM2 of claim 5(a) were sown with an HPPD inhibitor herbicide, optionally followed by application of glyphosate and/or glufosinate or a mixture of an HPPD inhibitor with glyphosate and/or glufosinate as post-emergent herbicide over the top of the plants.

30. A process for weed control, comprising treating soybean plants containing elite events EE-GM3 and EE-GM2 of claim 5(a) with an HPPD inhibitor herbicide over the top of the plants, applied together, followed by or preceded by a treatment with glyphosate and/or glufosinate as post-emergent herbicide over the top of the plants.

31. A method for producing a soybean plant tolerant to glyphosate and/or glufosinate and/or isoxaflutole herbicides, comprising introducing into the genome of such plant elite event EE-GM3 and elite event EE-GM2 of claim 5(a).

32. A method for controlling weeds in a field of soybean plants comprising elite events EE-GM3 and EE-GM1 of claim 1(a) comprising treating the field with an effective amount of an isoxaflutole-based and/or glyphosate-based and/or glufosinate-based herbicide, wherein such plants are tolerant to such herbicide(s).

33. A process for weed control, comprising treating a field in which seeds containing elite events EE-GM3 and EE-GM1 of claim 1(a) were sown with an HPPD inhibitor herbicide, optionally followed by application of glyphosate and/or glufosinate or a mixture of an HPPD inhibitor with glyphosate and/or glufosinate as post-emergent herbicide over the top of the plants.

34. A process for weed control, comprising treating soybean plants containing elite events EE-GM3 and EE-GM1 of claim 1(a) with an HPPD inhibitor herbicide over the top of the plants, applied together, followed by or preceded by a treatment with glyphosate and/or glufosinate as post-emergent herbicide over the top of the plants.

35. A method for producing a soybean plant tolerant to glyphosate and/or glufosinate and/or isoxaflutole herbicides, comprising introducing into the genome of such plant elite event EE-GM3 and elite event EE-GM1 of claim 1(a).

36. A soybean plant, plant part, cell, tissue, or seed comprising elite events EE-GM3 and EE-GM1.

37. A method for producing a soybean plant or seed comprising elite events EE-GM3 and EE-GM1, said method comprising crossing the plant according to claim 36 with another soybean plant, and planting the seed comprising elite events EE-GM3 and EE-GM1 obtained from said cross.

38. A soybean product produced from the seed of claim 36, wherein said soybean product comprises elite events EE-GM3 and EE-GM1 and comprises soybean meal, ground seeds, soybean flour, or soybean flakes.

39. A method for producing a soybean plant tolerant to glyphosate and/or isoxaflutole herbicides, comprising introducing into the genome of said soybean plant elite events EE-GM3 and EE-GM1 of claim 36, and selecting a progeny plant tolerant to glyphosate and/or isoxaflutole, wherein said progeny plant comprises elite events EE-GM3 and EE-GM1.

40. A method for controlling weeds in a field of the soybean plant of claim 36, comprising treating the field with an effective amount of an isoxaflutole-based, glyphosate-based and/or glufosinate-based herbicide, wherein said soybean plant is tolerant to said isoxaflutole-based herbicide.

41. A method for controlling weeds in a field of the soybean plants or seeds of claim 36, comprising treating a field with an HPPD inhibitor herbicide, before said soybean plants are planted or the seeds are sown, followed by planting or sowing of said soybeans in that same pre-treated field.

42. The method of claim 41, wherein glyphosate, or an HPPD inhibitor-glyphosate mixture, is applied as post-emergent herbicide over the top of said soybean plants once weeds tend to re-appear.

43. A method for controlling weeds in a field of the soybean seeds of claim 36, comprising treating a field in which said seeds were sown, with an HPPD inhibitor herbicide before the soybean plants emerge but after the seeds are sown.

44. The method of claim 43, wherein glyphosate, or an HPPD inhibitor-glyphosate mixture, is applied as post-emergent herbicide over the top of said soybean plants once weeds tend to re-appear.

45. A method for controlling weeds in a field of the soybean plants of claim 36, comprising treating said plants with an HPPD inhibitor herbicide over the top of the soybean plants, which application can be together with, followed by or preceded by a treatment with glyphosate as post-emergent herbicide over the top of the plants.

46. A soybean plant, plant part, cell, tissue, or seed comprising elite events EE-GM3 and EE-GM2.

47. A method for producing a soybean plant or seed comprising elite events EE-GM3 and EE-GM2, said method comprising crossing the plant according to claim 46 with another soybean plant, and planting the seed comprising elite events EE-GM3 and EE-GM2 obtained from said cross.

48. A soybean product produced from the seed of claim 46, wherein said soybean product comprises elite events EE-GM3 and EE-GM2 and comprises soybean meal, ground seeds, soybean flour, or soybean flakes.

49. A method for producing a soybean plant tolerant to glyphosate and/or isoxaflutole herbicides, comprising introducing into the genome of said soybean plant elite events EE-GM3 and EE-GM2 of claim 46, and selecting a progeny plant tolerant to glyphosate and/or isoxaflutole, wherein said progeny plant comprises elite events EE-GM3 and EE-GM2.

50. A method for controlling weeds in a field of the soybean plant of claim 46, comprising treating the field with an effective amount of an isoxaflutole-based herbicide, wherein said soybean plant is tolerant to said isoxaflutole-based herbicide.

51. A method for controlling weeds in a field of the soybean plants or seeds of claim 46, comprising treating a field with an HPPD inhibitor herbicide, before said soybean plants are planted or the seeds are sown, followed by planting or sowing of said soybeans in that same pre-treated field.

52. The method of claim 51, wherein glyphosate, or an HPPD inhibitor-glyphosate mixture, is applied as post-emergent herbicide over the top of said soybean plants once weeds tend to re-appear.

53. A method for controlling weeds in a field of the soybean seeds of claim 46, comprising treating a field in which said seeds were sown, with an HPPD inhibitor herbicide before the soybean plants emerge but after the seeds are sown.

54. The method of claim 53, wherein glyphosate, or an HPPD inhibitor-glyphosate mixture, is applied as post-emergent herbicide over the top of said soybean plants once weeds tend to re-appear.

55. A method for controlling weeds in a field of the soybean plants of claim 46, comprising treating said plants with an HPPD inhibitor herbicide over the top of the soybean plants, which application can be together with, followed by or preceded by a treatment with glyphosate as post-emergent herbicide over the top of the plants.

56. The soybean plant of claim 1(a), treated with any one of the following insecticides, herbicides or fungicides:
   (a) Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Isoxaflutole, or Glufosinate;
   (b) Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6 Chlorpyridin-3-yl)methyl](2,2-difluorethy)amino]furan-2(5H)-on, Spirotetramat, Spinodiclofen, Triflumuron, Flonicamid, Thiodicarb, or beta-Cyfluthrin;
   (c) Soybean Fungicides: Azoxystrobin, Cyproconazole, Epoxiconazole, Flutriafol, Pyraclostrobin, Tebuconazole, Trifloxystrobin, Prothioconazole, or Tetraconazole.

57. The soybean plant of claim 5(a), treated with any one of the following insecticides, herbicides or fungicides:
   (a) Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Isoxaflutole, or Glufosinate;
   (b) Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin -3-yl)methyl](2,2-difluorethy)amino]furan-2(5H)-on, Spirotetramat, Spinodiclofen, Triflumuron, Flonicamid, Thiodicarb, or beta-Cyfluthrin;
   (c) Soybean Fungicides: Azoxystrobin, Cyproconazole, Epoxiconazole, Flutriafol, Pyraclostrobin, Tebuconazole, Trifloxystrobin, Prothioconazole, or Tetraconazole.

58. The soybean plant of claim 36, treated with any one of the following insecticides, herbicides or fungicides:
   (a) Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Isoxaflutole, or Glufosinate;
   (b) Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin,β-Cyfluthrin, gamma and lambda Cyhalothrin, 4-[[(6-Chlorpyridin -3-yl)methyl](2,2-difluorethy)amino]furan-2(5H)-on, Spirotetramat, Spinodiclofen, Triflumuron, Flonicamid, Thiodicarb, or beta-Cyfluthrin;
   (c) Soybean Fungicides: Azoxystrobin, Cyproconazole, Epoxiconazole, Flutriafol, Pyraclostrobin, Tebuconazole, Trifloxystrobin, Prothioconazole, or Tetraconazole.

59. The soybean plant of claim 46, treated with any one of the following insecticides, herbicides or fungicides:
   (a) Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Isoxaflutole, or Glufosinate;
   (b) Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin -3-yl)methyl](2,2-difluorethyeamino]furan-2(5H)-on, Spirotetramat, Spinodiclofen, Triflumuron, Flonicamid, Thiodicarb, or beta-Cyfluthrin;
   (c) Soybean Fungicides: Azoxystrobin, Cyproconazole, Epoxiconazole, Flutriafol, Pyraclostrobin, Tebuconazole, Trifloxystrobin, Prothioconazole, or Tetraconazole.

60. The soybean plant, or cell, part, tissue, seed or progeny of claim 1(a).

61. The soybean plant, plant part, or seed, cell or tissue of claim 1(b).

62. The soybean seed of claim 1(c).

63. The soybean plant, plant part, cell, or tissue of claim 1(d).

64. The soybean plant, or cells, part, seed or progeny of claim 1(e).

65. The soybean plant, plant cell, tissue, or seed of claim 1(f).

* * * * *